United States Patent [19]
Suzuki et al.

[11] Patent Number: 5,207,947
[45] Date of Patent: May 4, 1993

[54] LIQUID CRYSTAL COMPOUND

[75] Inventors: Yoshiichi Suzuki; Noriko Yamakawa; Yoshihiko Aihara; Hiroyuki Mogamiya; Toru Ooide; Tadaaki Isozaki; Yuvraj Negi; Shigenori Sakuma, all of Tokyo, Japan

[73] Assignee: Showa Shell Sekiyu Kabushiki Kaisha, Tokyo, Japan

[21] Appl. No.: 713,143

[22] Filed: Jun. 11, 1991

Related U.S. Application Data

[63] Continuation-in-part of Ser. No. 592,683, Oct. 3, 1990, abandoned.

[30] Foreign Application Priority Data

| Oct. 6, 1989 | [JP] | Japan | 1-261804 |
| Nov. 21, 1989 | [JP] | Japan | 1-302569 |
| Nov. 29, 1989 | [JP] | Japan | 1-309709 |
| Dec. 12, 1989 | [JP] | Japan | 1-321829 |
| Dec. 27, 1989 | [JP] | Japan | 1-339482 |
| Jan. 22, 1990 | [JP] | Japan | 2-12005 |
| Jan. 22, 1990 | [JP] | Japan | 2-12006 |
| Jul. 9, 1990 | [JP] | Japan | 2-181186 |
| Nov. 20, 1990 | [JP] | Japan | 2-315142 |

[51] Int. Cl.⁵ .................... C09K 19/20; C09K 19/06; C07C 69/76
[52] U.S. Cl. .................. 252/299.67; 252/299.6; 560/56; 560/102; 560/65
[58] Field of Search ............. 560/65, 102, 56; 252/299.67, 299.6

[56] References Cited

U.S. PATENT DOCUMENTS

| 4,764,619 | 8/1988 | Gunjima et al. | 546/226 |
| 4,831,182 | 5/1989 | Higuchi et al. | 560/59 |
| 4,867,903 | 9/1989 | Nohira et al. | 252/299.61 |
| 4,911,861 | 3/1990 | Higuchi et al. | 252/299.65 |
| 4,918,213 | 4/1990 | Nohira et al. | 558/271 |
| 4,921,632 | 5/1990 | Nakamura et al. | 252/299.1 |
| 4,943,651 | 7/1990 | Nishiyama et al. | 560/56 |
| 4,952,335 | 8/1990 | Furukawa et al. | 252/299.61 |
| 4,973,738 | 11/1990 | Suzuki et al. | 560/80 |
| 5,046,823 | 9/1991 | Mori et al. | 359/56 |

FOREIGN PATENT DOCUMENTS

| 0327349 | 8/1989 | European Pat. Off. |
| 330491 | 8/1989 | European Pat. Off. |
| 332392 | 9/1989 | European Pat. Off. |
| 339987 | 11/1989 | European Pat. Off. |
| 8707890 | 12/1987 | World Int. Prop. O. |

OTHER PUBLICATIONS

Yamawaki et al., "Electro-Optical Properties of fluorine containing Ferroelectric Liquid Crystal Cells", Japan Dislay, 29 (1989).
J. Am. Chem. Soc. 1986, 108, 4736-4742.
Japanese Journal of Applied Physics, vol. 27, No. 5, May 1988, pp. L729-L732.
Liquid Crystals, 1988, vol. 3, No. 9, 1245-1254.

Primary Examiner—Robert L. Stoll
Assistant Examiner—C. Harris
Attorney, Agent, or Firm—Cushman, Darby & Cushman

[57] ABSTRACT

Liquid crystal compound of the formula

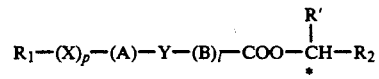

wherein $R_1$ and $R_2$ each is a $C_{1-18}$ alkyl group or an aralkyl group, R' is a haloalkyl group, X is —O—, —CO—, —COO— or direct bond, Y is —COO—, —OCO— or —CH$_2$O—, (A) and (B) each is

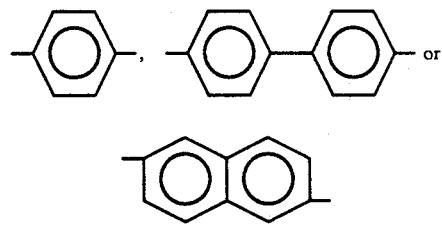

and p and l each is zero or one.

3 Claims, 44 Drawing Sheets

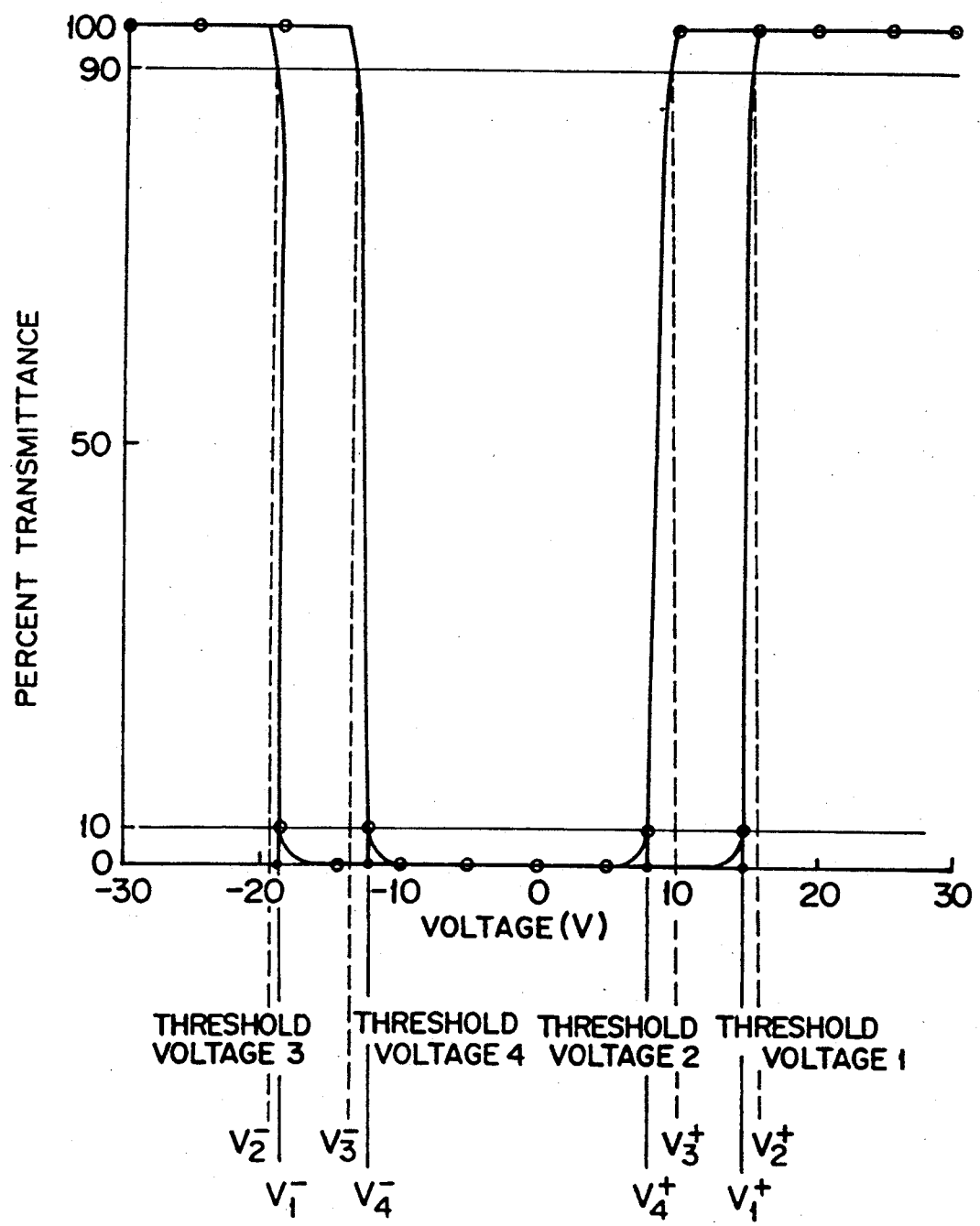

APPLIED TRIANGULAR WAVE VOLTAGE

OPTICAL RESPONSE OF CONVENTIONAL NEMATIC LIQUID CRYSTAL

OPTICAL RESPONSE OF CONVENTIONAL BISTABLE LIQUID CRYSTAL

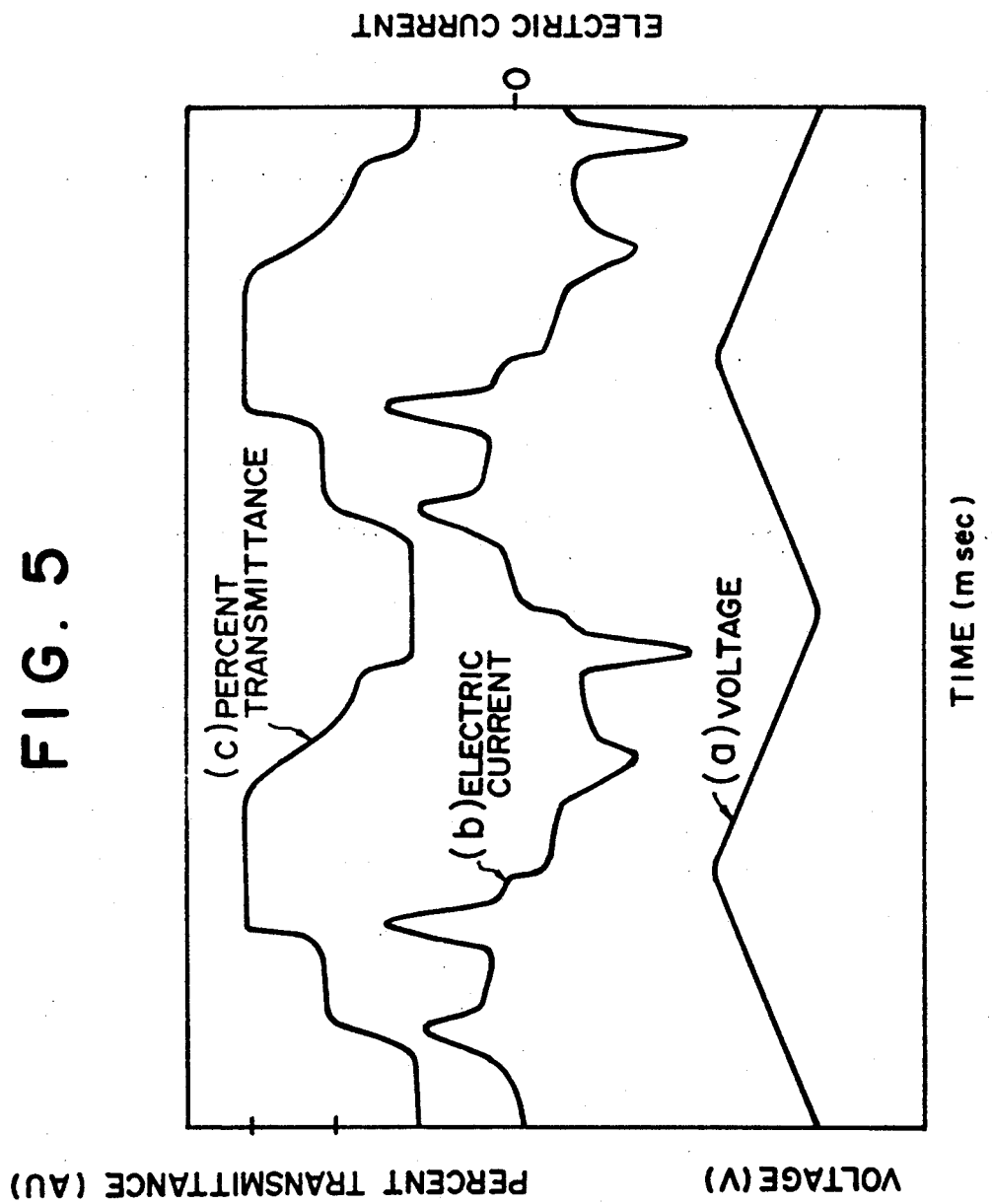

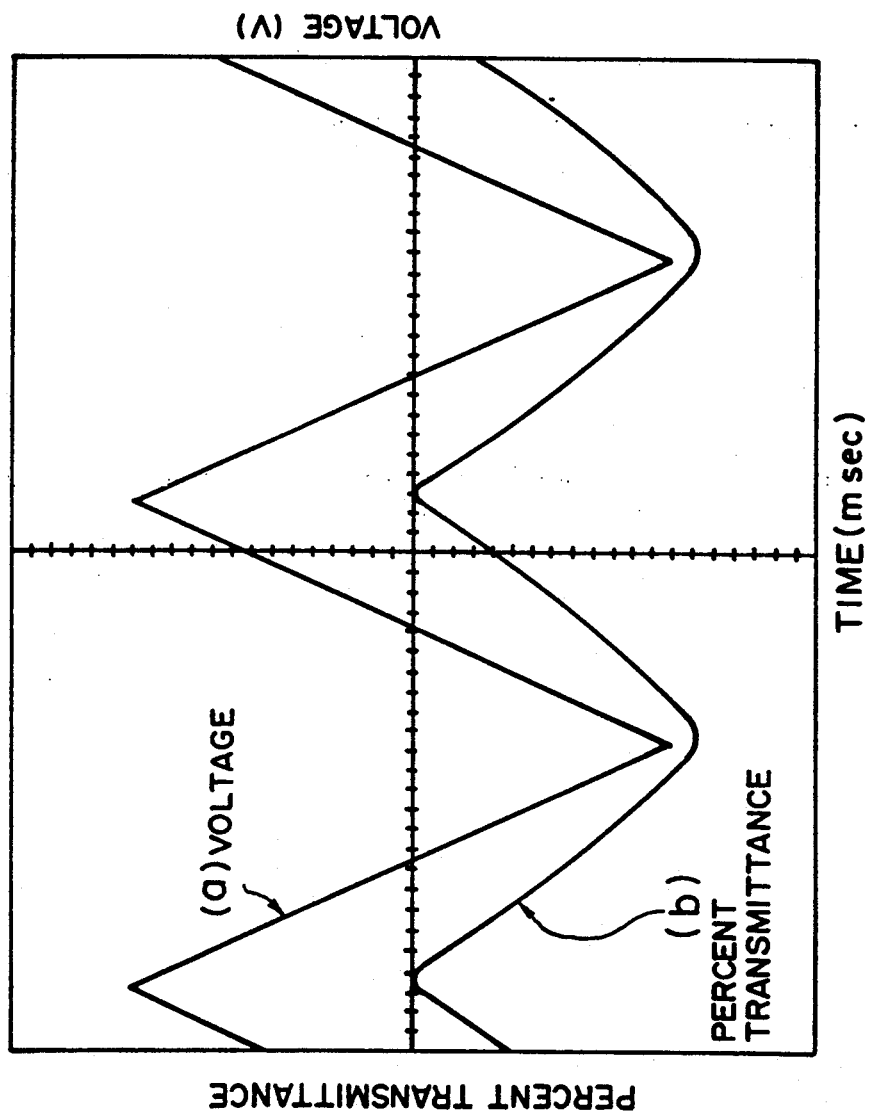

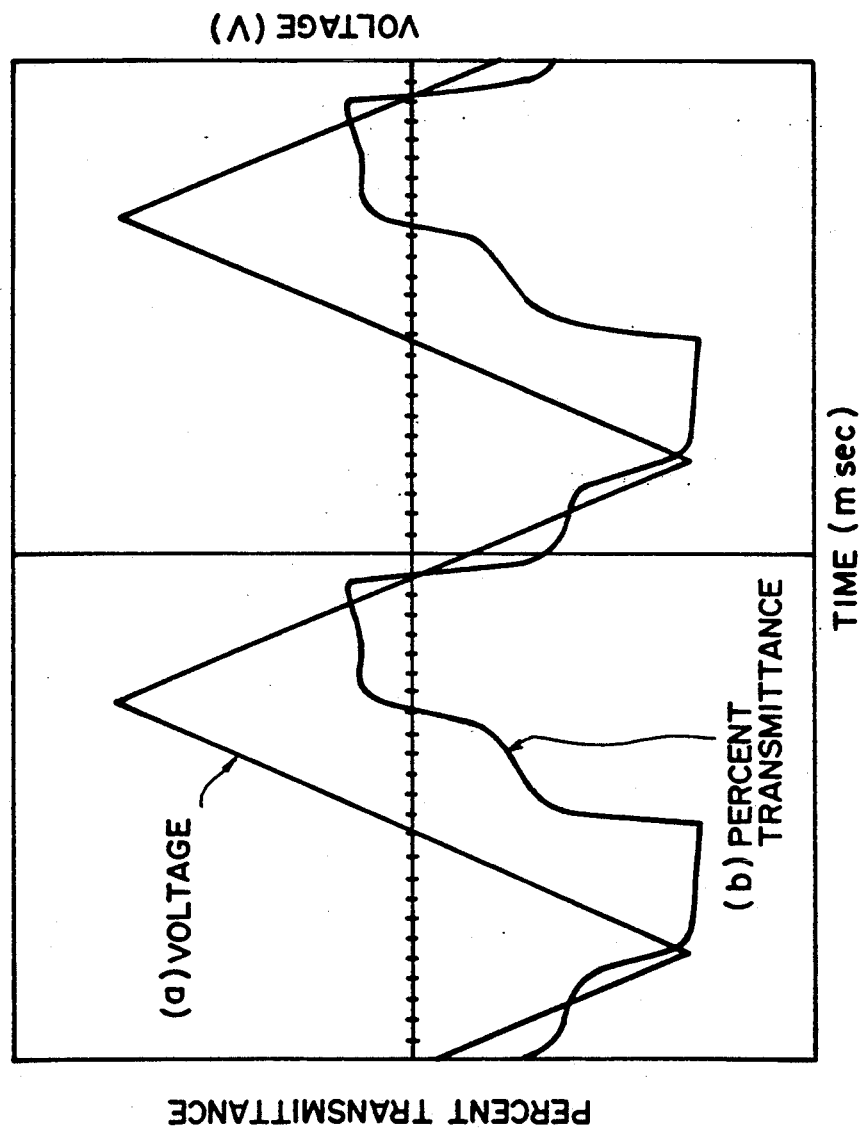

LIQUID CRYSTAL COMPOUND

This is a Continuation-in-Part of U.S. Ser. No. 07/592,683 filed Oct. 3, 1990, the disclosure of which is incorporated by reference.

The present invention relates to atom-containing liquid crystal compounds comprising esters or ethers of optically active alcohols. The present invention provides antiferroelectric liquid crystal compounds showing tristable states of molecular orientation and optical transmittance in $S^*(3)$ phase where triangular wave voltage is applied. The present invention also provides ferryelectric liquid crystal compounds showing tetrastable states of molecular orientation and optical transmittance in $S^*_{cy}$ phase ($S^*(4)$ phase) where triangular voltage is applied. The (S (4) phase) where triangular presnt liquid crystal compounds are useful for display devices or electro-optic devices.

Electrooptic devices utilzing liquid crystal compounds now available are those which employ nematic liquid crystals of DSM, TN, G-H or STN. Their wide range of usage is restricted, since their response speed is as small as a few $\mu$sec to some ten $\mu$sec. This is due to the fact that the torque for moving molecules, which depends on anisotropy of dielectric constant, is not so large. Therefore, ferroelectric liquid crystals having $S^*c$ phase are proposed which have response speed as large as 10 $\mu$sec to 100 $\mu$sec and have spontaneous polarization or Ps and large torque on the basis of Ps $\times$ E where E is an applied electric field (Meyer et al, Le Journal de Physique, 36, 1975, L-69). There are other liquid crystal compounds which show optically tristable states (JP 63-307837, 1-316367, 1-316339, 2-131450, 2-28128, 2-160748 and 2-213390).

So far as application of high speed electro-optical devices which employ ferroelectric liquid crystals are concerned, there is a device where a helical structure is released by wall forces and change is brought about in two molecular orientations which become parallel to the wall by use of polarity of applied fields (JP 56-107216). This is based on a premise that there is a compound having an ideal bistable states when triangular wave voltage is applied to as shown in FIG. 1. However, such a compound has not yet been found. Ferroelectric liquid crystals which have been actually synthesized have electric field response as shown in FIG. 2. Switching circuits for light which use such liquid crystal having electric field response as shown in FIG. 2 do not work well by only a change in applied electric voltage between "ON" and "OFF", since percent transmittance grandually changes as applied electric voltage changes from a $\ominus$ side to a $\oplus$ side. Another difficulty is that it is very difficult to synthesize liquid crystals which have the ideal bistable orientation everywhere in a large area. The ferroelectric liquid crystals actually available are difficult to form a monodomain structure, i.e., an ideal molecular orientation in $S^*c$ phase where no electric field is applied to but easily form disclination or twist or zigzag defect in molecular orientation. Another difficulty is decreasing contrast or narrowing a field of view when dynamic driving is applied, since threshold voltage where luminance varies at a given level is small. Furthermore, ferroelectric liquid crystals actually synthesized have no memory effect, since their hysteresis is not as in FIG. 1 but as in FIG. 2. So a large amount of energy is lost in order to have stable response at the $S^*c$ phase of liquid crystals maintained, since it is obliged to apply electric voltage of V3 in FIG. 2 throughout or to apply high frequency throughout.

Although high speed liquid crystal electro-optic devices are expected where strong interaction between applied electric fields and molecular orientation brought about from ferroelectric liquid crystals is employed, conventional devices using ferroelectiric liquid crystals leave many problems unsolved.

The present invention provides novel antiferroelectric liquid crystal compounds which are able to be used for liquid crystal electro-optic devices which make use of tristable states in $S^*(3)$ phase. $S^*(3)$ phase is far from conventional chiral smectic C phase ($S^3C$), where stable molecular orientation of clear hidden contrast is seen when no electric fields are applied to, sharp threshold characteristic and clear hysteresis as shown in FIG. 3A of tristable states and FIG. 3B of tetrastable state are revealed and dynamic addressing scheme is adopted with high speed response. One of the objects of the present invention is to provide antiferroelectric liquid crystals having $S^*(3)$ phase or antiferroelectric phase where antiferroelectric liquid crystal compounds show tristable states which is far from the known bistable states. Then the $S^*(3)$ phase is different from a chiral smectic C phase ($S^*c$ phase). Reference is made to FIG. 4 D with respect to the tristable states mentioned above. That is, when triangular wave voltage as in FIG. 4 A is applied to liquid crystal electro-optic devices where antiferroelectric liquid crystals are laid between the first electrode substrate plate and the second electrode substrate plate which is spaced at a given distance from the first one and electric voltage for electric field is applied to the both electrode substrate plates, the antiferroelectric liquid crystals nave molecular orientation of the first stable state as shown in FIG. 4 D, 2 where no electric field is applied, but upon application of electric field, molecular orientation of the second stable state as shown in FIG. 4 D, 1 which is different from the first stable state in one of electric field directions and molecular orientation of the third stable state as shown in FIG. 4 D, 3 which is also different from the first and second stable states in the other direction of electric field.

Liquid crystal electro-optic devices which utilize the tristable states are proposed (JP 2-40625, 2-153322, 2-173724 and 2-176723). Tristable state switching performance of the present invention is shown in FIG. 5 where change of transmittance and swtiching current peaks are shown when a triangular wave electric voltage is applied to the liquid crystal which shows tirstable states. Neither nematic liquid crystals available in the market nor bistable liquid crystals actually synthesized have $S^*(3)$ phase showing tristable states as shown in FIG. 4 8 and 4 C.

The present antiferroelectric liquid crystals showing tristable states exhibit epoch-making effects which are beyond expectation from the conventional menatic liquid crystals, when they are installed in liquid crystal displays. Conventional liquid crystal displays of active-matrix-driven require complex structures which result complex manufacturing processes. Large scale displays are hard to be prepared and owing to the high manufacturing cost. On the other hand, simple matrix displays are enough for the antiferroelectric liquid crystals showing tristable states in S (3) phase, so that manufacturing processes are simple and production of large scale displays is possible because of its low manufacturing cost.

Another object of the present invention is to provide liquid crystal compounds having a novel tetrastable state between the usual smectic C phase showing bistable states and the S*(3) phase showing tristable states.

FIG. 4 E represents the tetrastable states which differ from tristable states. That is, electric voltage is applied to the first and second electrode substrate plates mentioned below of liquid crystal electro-optic devices where liquid crystals are laid between the first electrode substrate plate and the second electrode substrate plate spaced at a given distance from the first one. When triangular wave voltage is applied as shown in FIG. 4 A, the antiferroelectric liquid crystals have molecular orientation of either the first or the second stable state as shown in FIG. 4 E, 2 or 3 where no electric field is applied, but, upon application of electric field, molecular orientation of the third stable state as shown in FIG. 4 E, 1, which is different from both the first and the second stable states, in one of the directions of electric field, and molecular orientation of the fourth stable state as shown in FIG. 4 E, 4, which is different from any of the first, second and third stable states, in the other direction of the electric field. FIG. 4 A–4 E and 8 show change of transmittance strength and switching current peaks when electric voltage of triangular wave is applied to liquid crystals in S*(3) phase showing tristable states and in S*$_{cy}$ phase showing tetrastable states, respectively. S*$_{cy}$ phase was represented as S*(4) phase bofore. Transmittance changes in four states, i.e., dark state, medium state 1, medium state 2 and clear state. There are corresponding three switching current peaks.

Nakamura et al (U.S. Pat. No. 4,921,632) and Nohira (U.S. Pat. No. 4,918,213) disclose various ferroelectric smectic liquid crystal compounds. But they disclose no S (3) phase where antiferroelectric liquid crystal compounds show tristable states, though they describe unidentified ferroelectric smectic phases as $S_1$, $S_3$ or $S_4$.

The present compounds have the following formula $$R_1-(X)_p-(A)-COO-(B)-COO-\overset{R_3}{\underset{*}{C}H}-R_2$$

wherein each of $R_1$ and $R_2$ is a $C_{1-18}$ alkyl group, $R_3$ is haloalkyl group such as $CH_2F$, $CHF_2$, $CF_3$, $C_2F_5$, $CClF_2$, $CCl_2F$, $CCl_3$, $CF_3CCl_2$ or $CF_2ClCF_2$, preferably $CF_3$, $CHF_2$, $CH_2F$ and $C_2F_5$, X is —O—, —CO— or —COO—, each of A and B is an aryl group where one to four of the hydrogen atoms therein may be substituted by a halogen atom, or one or two hydrogen atoms therein may be substituted by members selected from a chlorine atom and a trifluoromethyl group, p is zero or one, and * is an asymmetric carbon (the same hereinafter). The aryl group is

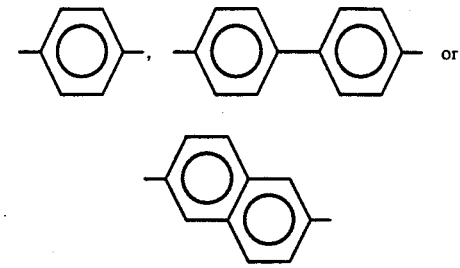 or where one to four of the hydrogen atoms may be substituted by a fluorine atom or one or two of the hydrogen atoms may be substituted by a member or members selected from a fluorine atom, a chlorine atom, a bromine atom and a trifluoromethyl group. Preferable aryl groups are

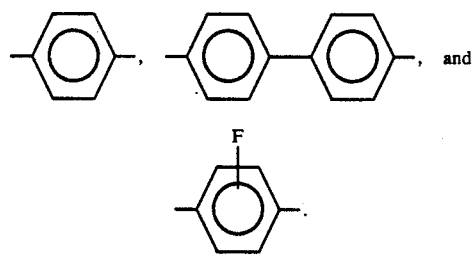

Appearance of the tristable states depends on the structure of the compounds as follows i) when the symbol X is esters, direction of the esters is the same, e.g., X is $$\underset{\underset{\displaystyle CO}{\|}}{\overset{O}{-}}-,$$

ii) either one of A and B is a biphenyl group and the other is a phenyl group, and iii) the most peference of $R_3$ bonded to the asymmetric carbon is a $CF_3$ group wherein the direction of esters i) is not so critical; a $C_2F_5$ group is the next preference.

Some examples of dependency of antiferroelectricity or tristable state upon skeletons is as follows:

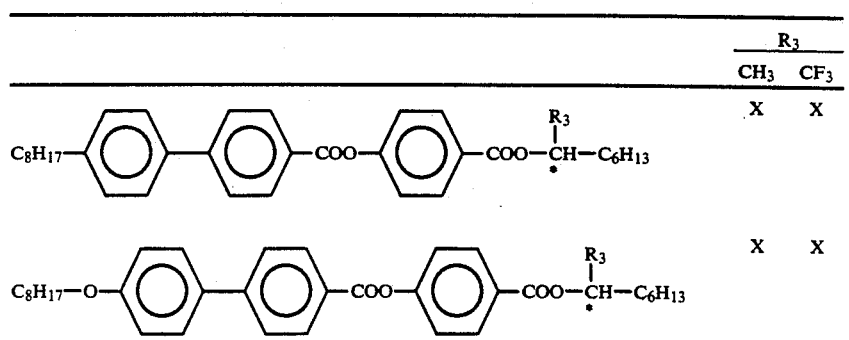

| | R₃ | |
|---|---|---|
| | CH₃ | CF₃ |
| C₈H₁₇—CO—⟨⟩—⟨⟩—COO—⟨⟩—COO—CH(R₃)*—C₆H₁₃ | X | X |
| C₈H₁₇—COO—⟨⟩—⟨⟩—COO—⟨⟩—COO—CH(R₃)*—C₆H₁₃ | X | X |
| C₈H₁₇—OCO—⟨⟩—⟨⟩—COO—⟨⟩—COO—CH(R₃)*—C₆H₁₃ | — | X |
| C₈H₁₇—O—⟨⟩—COO—⟨⟩—⟨⟩—COO—CH(R₃)*—C₆H₁₃ | — | X |
| C₈H₁₇—⟨⟩—COO—⟨⟩—⟨⟩—COO—CH(R₃)*—C₆H₁₃ | — | X |
| C₈H₁₇—O—⟨⟩—OCO—⟨⟩—⟨⟩—COO—CH(R₃)*—C₆H₁₃ | — | X |
| C₈H₁₇—O—⟨⟩—⟨⟩—OCO—⟨⟩—COO—CH(R₃)*—C₆H₁₃ | — | — |

X: tristable states
—: no tristable states

The present liquid crystal compounds belong to six groups as follows.

Group 1

The compounds belonging to the group have the formula

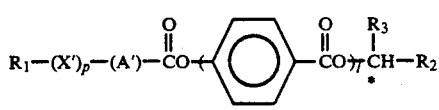

wherein $R_1$, $R_2$, $R_3$ and p are as defined above, X' is —O—, (A') is

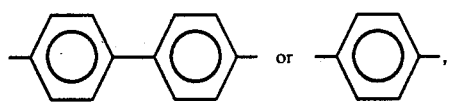

and l is zero or one. They include, for instance,
4-(1,1,1-trifluoro-2-octyloxycarbonyl)phenyl 4-alkyloxybiphenyl-4'-carboxylate,
4-(1,1,1-trifluoro-2-octyloxycarbonyl)phenyl 4-alkyl-biphenyl-4'-carboxylate,
4-(1,1,1,2,2-pentafluoro-3-undecyloxycarbonyl) phenyl 4-alkyloxybiphenyl-4'-carboxylate, and
4-(1-chloro-1,1-difluoro-4-phenyl-2-butyloxycarbonyl)phenyl 4-alkyloxybiphenyl-4'-carboxylate.

There are (R)-isomers and (S)-isomers in the optically active compounds and derivatives thereof. It is desired that their optical purities are higher, but their optical purity is not critical.

One of processes for preparing the compounds is that 4-benzyloxybenzoic acid is allowed to react with chlorinating agents such as thionyl chloride in order to convert the benzoic acid to the acid chloride form which is allowed to react with (R)-(+)- or (S)-(—)-trifluoro-2-alkanols until esters are formed. The esters are subjected to de-benzyl reaction to produce phenol compounds which are allowed to react with 4-alkyloxy-4'-biphenylcarboxylic acid chloride.

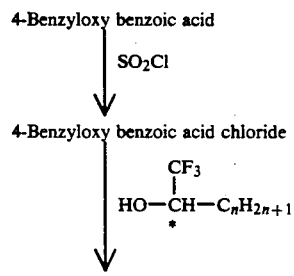

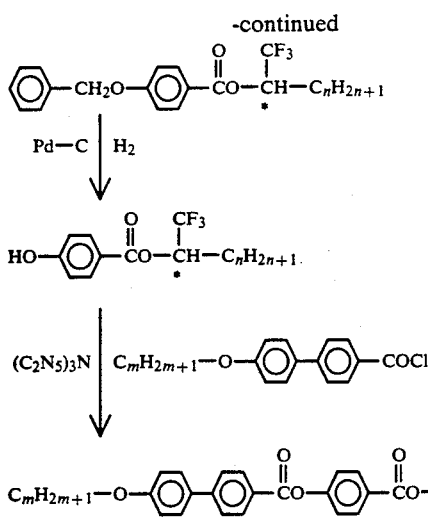

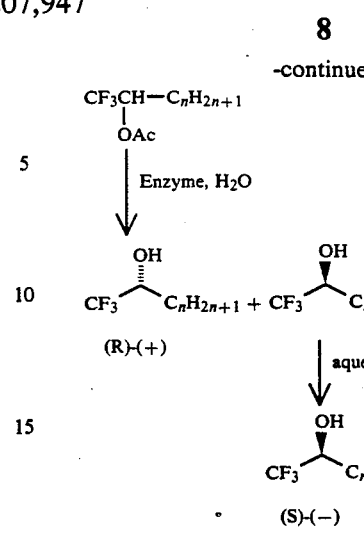

The optically active haloalkanols mentioned above have the formula $$HO-\underset{*}{CH}-R_1$$
$$\quad\quad | $$
$$\quad R_3$$

wherein $R_1$ and $R_3$ are as defined above.

Examples of the optically active haloalcohols are, 1,1,1-trifluoro-2-hexanol, 1,1,1-trifluoro-2-heptanol, 1,1,1-trifluoro-2-octanol, 1,1,1-trifluoro-2-nonal, 1,1,1-trifluoro-2-decanol, 1,1,1-trifluoro-2-undecanol, 1,1,1-trifluoro-2-dodecanol, 1,1,1-trifluoro-2-tridecanol, 1,1,1-trifluoro-2-tetradecanol, 1,1,1-trifluoro-2-pentadecanol, 1,1,1-trifluoro-2-hexadecanol, 1,1,1-trifluoro-2-heptadecanol, and 1,1,1-trifluoro-2-octadecanol. The trifluoromethyl group may be replaced by a monofluoromethyl group, difluoromethyl group, a pentafluoroethyl group or a dichloromonofluoromethyl group.

The alcohols are obtained by asymmetric synthesis or optical resolution. The alcohols having high optical purity are produced by use of enzymes, yeasts or bacteria. One of processes is allowing ethyl/trifluoroacetate to react with Grignard reagent of alkylbromide to produce trifluoroalkyl ketone, reducing the ketone with sodium borohydride to produce 1-trifluoro-2-alkanol, deriving into acetate, and stereoselectively hydrolyzing with yeasts or bacteria to obtain (R)- or (S)- optically active 1-trifluoro-2-alkanol.

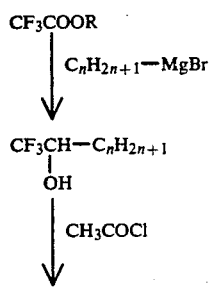

The corresponding optically active 1-haloalkyl-2-alkanols are obtained by use of ethyl monofluoroacetate, ethyl difluoroacetate, ethyl pentafluoroacetate and ethyl trichloroacetate in place of the ethyl trifluoroacetate.

Group 2

The compounds belonging to the group have the formula

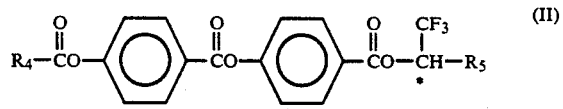

wherein $R_4$ is a $C_{8-18}$ alkyl group, preferably a straight chain alkyl group, more preferably a $C_{9-10}$ straight chain alkyl group, and $R_5$ is a $C_{6-16}$ alkyl group, preferably a straight chain alkyl group, more preferably, a $C_{6-8}$ straight chain alkyl group. The compounds are featured in that they are at the tristable state at a temperature below zero degree.

They are used alone but may be a mixture thereof, a mixture with the other liquid crystals or a mixture with liquid crystals having the similar structure thereto, in order to control specific properties of the liquid crystals.

Appearance of tristable state depends on the structure of the compounds as follows:

i) $CF_3$ bonded to the asymmetric carbon is critical; it is rather difficult for tristable states to appear when the $CF_3$ is replaced by $CH_3$, and ii) directions of the esters are the same as that of $$\underset{\|}{-\text{C}\text{O}-}$$
$$\;\;\;\text{O}$$

bonded to the asymmetric carbon.

One of processes for preparing the compounds is that 4-benzyloxybenzoic acid chloride is allowed to react with optically active 1,1,1-trifluoro-2-alkanol in order to obtain 1,1,1-trifluoro-2-alkyl-4-benzyloxybenzoate which is then subjected to hydrogenation to produce 1,1,1-trifluoro-2-alkyl 4-hydroxy-benzoate. The benzoate obtained is allowed to react with 4-n-alkylcarbonyloxyphenylcarboxylic acid in the presence of dichlorohexylcarbodiimide until the desired optically active 4-(1,1,1-trifluoro-2-alkyloxycarbonyl)phenyl 4-n-alkylcarbonyloxybenzoate.

Group 3

The compounds belonging to the group have the formula

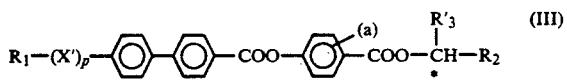

wherein $R_1$, $R_2$, $X'$ and p are so as defined above, (a) is a group selected from F, Cl, Br and $CF_3$, and the phenylene group has one to four substituents when (a) is F and has one to two substituents when (a) is a group excluding F and $R'_3$ is $CF_3$ or $C_2F_5$. They show tristable and tetrastable states when in $S^*(3)$ phase or $S^*_{cy}$ phase, repectively.

They include, for example,
3-fluoro-4-(1,1,1-trifluoro-2-hexyloxycarbonyl) phenyl 4-alkyloxybiphenyl-4'-carboxylate,
3-fluoro-4-(1,1,1-trifluoro-2-heptyloxycarbonyl) phenyl 4-alkyloxybiphenyl-4'-carboxylate,
3-fluoro-4-(1,1,1-trifluoro-2-octyloxycarbonyl) phenyl 4 alkyloxybiphenyl-4'-carboxylate,
3-fluoro-4-(1,1,1-trifluoro-2-nonyloxycarbonyl) phenyl 4-alkyloxybiphenyl-4'-carboxylate,
3-fluoro-4-(1,1,1-trifluoro-2-decyloxycarbonyl) phenyl 4-alkyloxybiphenyl-4'-carboxylate,
3-fluoro-4-(1,1,1-trifluoro-2-undecyloxycarbonyl) phenyl 4-alkyloxybiphenyl-4'-carboxylate,
3-fluoro-4-(1,1,1-trifluoro-2-dodecyloxycarbonyl) phenyl 4-alkyloxybiphenyl-4'-carboxylate,
3-fluoro-4-(1,1,1-trifluoro-2-tridecyloxycarbonyl) phenyl 4-alkyloxybiphenyl-4'-carboxylate,
3-fluoro-4-(1,1,1-trifluoro-2-tetradecyloxycarbonyl)-phenyl 4-alkyloxybiphenyl - 4'-carboxylate,
3-fluoro-4-(1,1,1-trifluoro-2-tetradecyloxycarbonyl)-phenyl 4-alkyloxybiphenyl - 4'-carboxylate,
3-fluoro-4-(1,1,1-trifluoro-2-pentadecyloxycarbonyl)-phenyl 4-alkyloxybiphenyl-4'-carboxylate,
3-fluoro-4-(1,1,1-trifluoro-2-hexadecyloxycarbonyl)-phenyl 4-alkyloxybiphenyl-4'-carboxylate,
3-fluoro-4-(1,1,1-trifluoro-2-heptadecyloxycarbonyl)-phenyl 4-alkyloxybiphenyl-4'-carboxylate, and
3-fluoro-4-(1,1,1-trifluoro-2-octadecyloxycarbonyl)-phenyl 4-alkyloxybiphenyl-4'-carboxylate.

The trifluoromethyl group may be replaced by a monofluoromethyl group, a difluoromethyl group, or a pentafluoroethyl group. There are (R)-isomers and (S)-isomers in the optically active compounds and derivatives thereof. It is desired that optical purity is higher but is not critical.

The compounds are synthesized in the same manner as in those of group 1. That is, fluoro-4-benzyloxybenzoic acid is allowed to react with chlorination agents such as thionyl chloride to obtain acid chloride of the benzoic acid which is allowed to react with (R)- or (S)-trifluoro-2-alkanols to obtain esters. The esters are subjected to hydrolysis and then the phenolic compounds thus obtained are allowed to react with 4-alkyloxy-4'-biphenyl carboxylic acid chloride.

Fluoro-4-benzyloxybenzoic acid

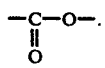

-continued
Fluoro-4-benzyloxybenzoic acid chloride

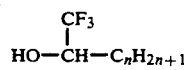

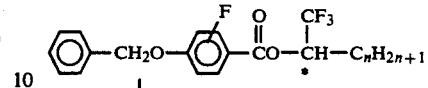

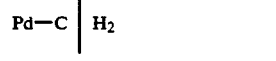

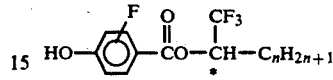

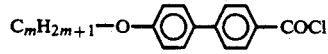

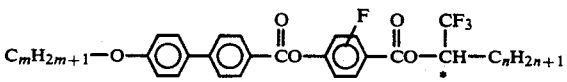

Alternatively, the compounds may be prepared by dehydration condensation between 4-alkyloxy-4'-biphenylcarboxylic acid and phenol derivatives of (R)- or (S)-trifluoro-2-alkanols in the presence of condensating agents such as dicyclohexylcarbodiimide.

Group 4

Compounds belonging to this group have the formula (IV) or (V):

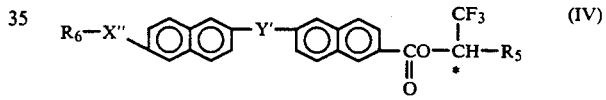

wherein $R_6$ is a $C_{5-18}$ alkyl group, $R_5$ is a defined above; $X'''$ is —O—,

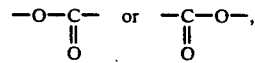

$Y'$ is

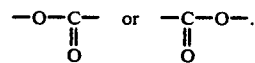

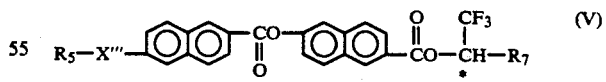

where $R_5$ is as defined above, $R_7$ is a $C_{6-16}$ alkyl group and $X'''$ is —O— or $$-\underset{\underset{O}{\|}}{C}-O-.$$

They are used for liquid crystals which utilize tristable states as well as those which utilize bistable One of processes for preparing the compounds of the formula (IV) or (V) is that 2-hydroxy-6-carboxynaphthalene is allowed to react with optically active 1-trifluoromethylalkyl alcohol in ethylene chloride in the presence of sulfuric acid to obtain 1,1,1-trifluoro-2-alkyl 6-hydroxynaphthalene-2-carboxylate.

Separately, alkyl bromide is allowed to react with 2-hydroxy-6-carboxynaphthalene in a solvent such as dimethylformamide in the presence of potassium carbonate, and the reaction product is hydrolyzed in aqueous sodium hydroxide solution. The hydrolyzed product is allowed to react with the 1,1,1-trifluoro-2-alkyl 6-hydroxynaphthalene-2-carboxylate in the presence of dicyclohexyl carbodiimide to obtain 6-(1,1,1-trifluoro-2-alkyloxycarbonyl)naphthalene-2-ester of 6-alkyloxynaphthalene-2-carboxylic acid.

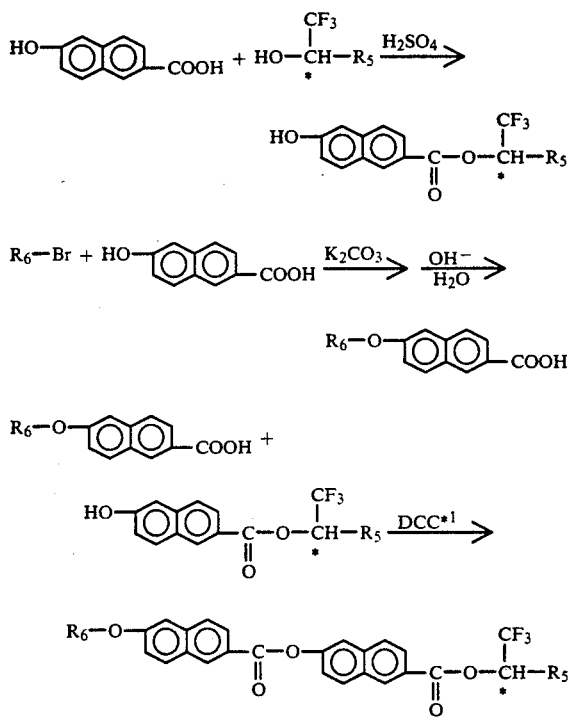

Another process is that fatty acid chloride is allowed to react with 2-hydroxy-6-carboxynaphthalene to obtain 2-alkylcarbonyloxynaphthalene-6-carboxylic acid, followed by a reaction with 1-trifluoromethylalkyl 6-hydroxynaphthalene-2-carboxylate in the presence of dicyclohexylcarbodiimide to obtain 6-(1,1,1-trifluoro-2-alkyloxycarbonyl)napohthalene-2-ester of 6-alkylcarbonyloxynaphthalene-2-carboxylic acid.

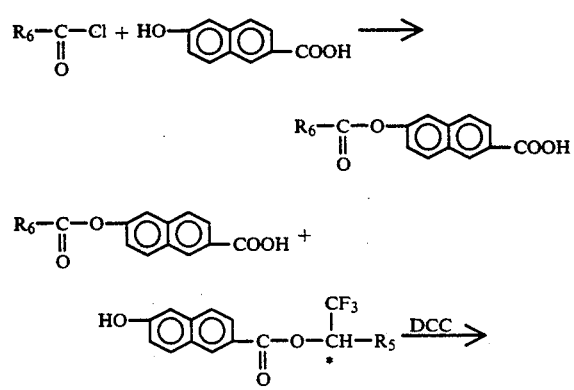

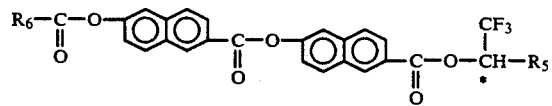

The other process is that alkyl alcohol is allowed to react with naphthalene 2,6-dicarboxylic acid dichloride to produce 6-(alkyloxycarbonyl)naphthalene-2-carboxylic acid chloride, followed by a reaction with 1,1,1-trifluoro-2-alkyl-6-hydroxy-naphthalene-2-carboxylate to produce 6-(1,1,1-trifluoro-2-alkyloxycarbonyl)naphthalene - 2-ester of 6-(alkyloxycarbonyl)naphthalene-2-carboxylic acid.

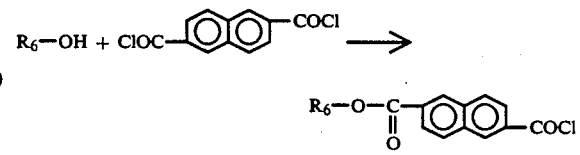

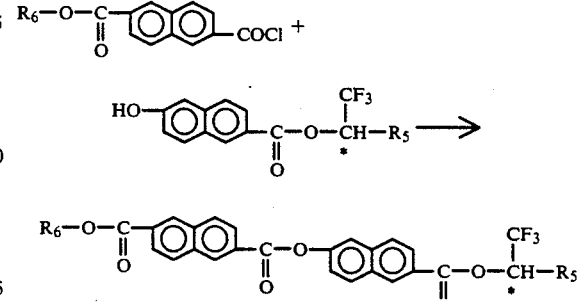

Group 5

Compounds belonging to this group have the formula (VI), (VII) or (VIII):

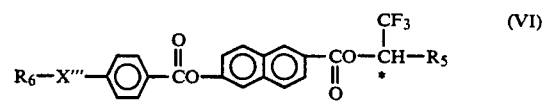
(VI)

where $R_6$, $R_5$ and $X''''$ are as defined above,

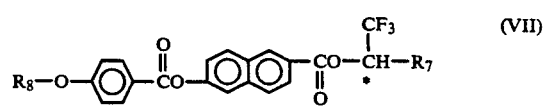
(VII)

wherein $R_8$ is a $C_{10-16}$ alkyl group and $R_7$ is as defined above,

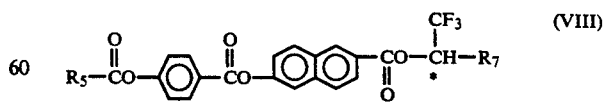
(VIII)

where $R_5$ and $R_7$ are as defined above.

The present compounds are usable as liquid crystals which employ optically tristable states or optically tetrastable states as well as conventional bistable states.

One of the processes for preparing the same is that 2-hydroxy-6-carboxynaphthalene is allowed to react with optically active 1,1,1-trifluoroalkyl-2-alcohol in ethylene chloride in the presence of sulfuric acid to obtain 1,1,1-trifluoro-2-alkyl 6-hydroxynaphthalene-2-carboxylate. Separately, alkyl bromide is allowed to react with 4-hydroxybenzoic acid in a solvent such as dimethylformamide in the presence of potassium carbonate, and the product is hydrolyzed with aqueous sodium hydroxide solution to obtain 4-alkyloxybenzoic acid which is further allowed to react with the 1,1,1-trifluoro-2-alkyl 6-hydroxynaphthalene-2-carboxylate to obtain 1,1,1-trifluoro-2-alkyl 6-(4-alkyloxyphenylcarbonyloxy)naphthalene-2-carboxylate.

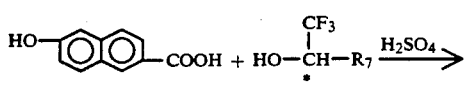

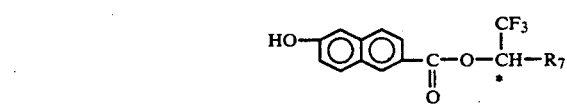

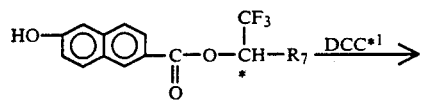

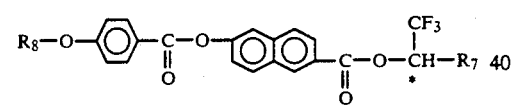

Another process is that fatty acid chloride is allowed to react with 4-hydroxybenzoic acid to obtain 4-alkylcarbonyloxybenzoic acid which is then allowed to react with 1,1,1-trifluoro-2-alkyl 6-hydroxynaphthalene-2-carboxylate in the presence of dicyclohexylcarbodiimide to produce 1,1,1-trifluoro-2-alkyl 6-(4-alkylcarbonyl-oxyphenylcarbonyloxy)naphthalene-2-carboxylate.

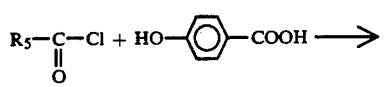

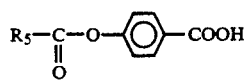

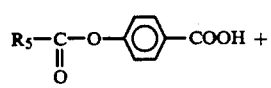

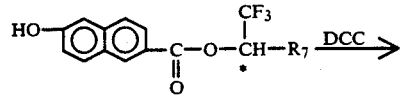

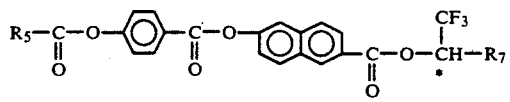

Group 6

Compounds belonging to this group have the formula (IX)

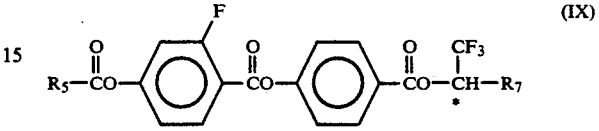

wherein $R_5$ and $R_7$ are as defined above.

They are featured in that they are in tristable state, particularly, at a temperature below in ice point.

Group 7

Compounds belonging to this group have the formula

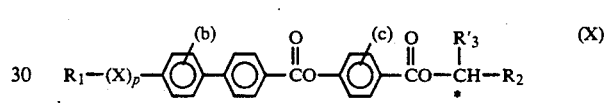

wherein $R_1$, $R_2$, $R'_3$, X and p are as defined above, (b) and (c) each is selected from F, Cl and Br and the biphenyl and phenylene rings have one to four substituents when (b) or (c) is F and have one to two substituents when (b) or (c) is the other atoms than the F. The compounds have optically tristable states.

Group 8

Compounds belonging to this group have the formula

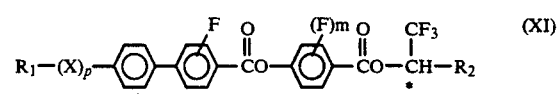

wherein $R_1$, $R_2$ X and p are as defined above and m is zero or one.

Examples belonging to the groups 7 and 8 are as follows:

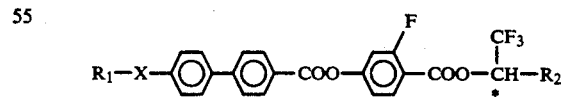

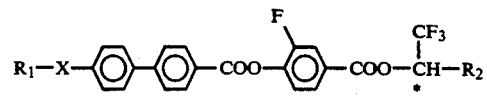

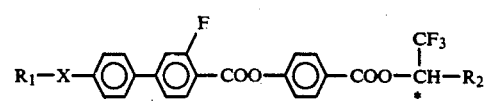

-continued $$R_1-X-\phenyl(F)-\phenyl-COO-\phenyl-COO-CH(CF_3)^*-R_2$$

$$R_1-X-\phenyl(F)-\phenyl-COO-\phenyl-COO-CH(CF_3)^*-R_2$$

$$R_1-X-\phenyl(F)-\phenyl-COO-\phenyl-COO-CH(CF_3)^*-R_2$$

$$R_1-X-\phenyl-\phenyl-COO-\phenyl(F,F)-COO-CH(CF_3)^*-R_2$$

$$R_1-X-\phenyl-\phenyl-COO-\phenyl(F,F)-COO-CH(CF_3)^*-R_2$$

$$R_1-X-\phenyl-\phenyl(F)-COO-\phenyl(F)-COO-CH(CF_3)^*-R_2$$

$$R_1-X-\phenyl(F)-\phenyl-COO-\phenyl(F)-COO-CH(CF_3)^*-R_2$$

$$R_1-X-\phenyl-\phenyl(F)-COO-\phenyl(F,F)-COO-CH(CF_3)^*-R_2$$

$$R_1-X-\phenyl(F)-\phenyl-COO-\phenyl(F)-COO-CH(CF_3)^*-R_2$$

$$R_1-X-\phenyl-\phenyl-COO-\phenyl(F,F,F)-COO-CH(CF_3)^*-R_2$$

$$R_1-X-\phenyl-\phenyl(F)-COO-\phenyl(F)-COO-CH(CF_3)^*-R_2$$

$$R_1-X-\phenyl-\phenyl(F)-COO-\phenyl(F)-COO-CH(CF_3)^*-R_2$$

$$R_1-X-\phenyl-\phenyl(F)-COO-\phenyl(F)-COO-CH(CF_3)^*-R_2$$

$$R_1-X-\phenyl-\phenyl(F)-COO-\phenyl(F)-COO-CH(CF_3)^*-R_2$$

-continued $$R_1-X-\phenyl-\phenyl(F,F)-COO-\phenyl-COO-CH(CF_3)^*-R_2$$

$$R_1-X-\phenyl(F,F)-\phenyl-COO-\phenyl-COO-CH(CF_3)^*-R_2$$

$$R_1-X-\phenyl(F)-\phenyl(F)-COO-\phenyl-COO-CH(CF_3)^*-R_2$$

$$R_1-X-\phenyl(F)-\phenyl(F)-COO-\phenyl-COO-CH(CF_3)^*-R_2$$

$$R_1-X-\phenyl-\phenyl(F,F)-COO-\phenyl-COO-CH(CF_3)^*-R_2$$

$$R_1-X-\phenyl(F)-\phenyl-COO-\phenyl(F,F)-COO-CH(CF_3)^*-R_2$$

$$R_1-X-\phenyl(F)-\phenyl-COO-\phenyl(F,F)-COO-CH(CF_3)^*-R_2$$

$$R_1-X-\phenyl(F)-\phenyl-COO-\phenyl(F,F)-COO-CH(CF_3)^*-R_2$$

$$R_1-X-\phenyl(F)-\phenyl-COO-\phenyl(F,F)-COO-CH(CF_3)^*-R_2$$

$$R_1-X-\phenyl-\phenyl(F)-COO-\phenyl(F,F,F)-COO-CH(CF_3)^*-R_2$$

$$R_1-X-\phenyl(F)-\phenyl-COO-\phenyl(F,F,F)-COO-CH(CF_3)^*-R_2$$

$$R_1-X-\phenyl(F)-\phenyl(F)-COO-\phenyl(F,F)-COO-CH(CF_3)^*-R_2$$

-continued $R_1-X-\bigcirc-\bigcirc(F,F)-COO-\bigcirc(F,F)-COO-\overset{CF_3}{\underset{*}{C}H}-R_2$ $R_1-X-\bigcirc-\bigcirc(F,F)-COO-\bigcirc(F)-COO-\overset{CF_3}{\underset{*}{C}H}-R_2$ $R_1-X-\bigcirc-\bigcirc(F,F)-COO-\bigcirc(F)-COO-\overset{CF_3}{\underset{*}{C}H}-R_2$ $R_1-X-\bigcirc-\bigcirc(F,F)-COO-\bigcirc(F)-COO-\overset{CF_3}{\underset{*}{C}H}-R_2$ $R_1-X-\bigcirc-\bigcirc(F,F)-COO-\bigcirc(F)-COO-\overset{CF_3}{\underset{*}{C}H}-R_2$ $R_1-X-\bigcirc-\bigcirc(F,F)-COO-\bigcirc(F)-COO-\overset{CF_3}{\underset{*}{C}H}-R_2$ $R_1-X-\bigcirc-\bigcirc(F,F)-COO-\bigcirc(F)-COO-\overset{CF_3}{\underset{*}{C}H}-R_2$ $R_1-X-\bigcirc(F,F)-\bigcirc-COO-\bigcirc(F)-COO-\overset{CF_3}{\underset{*}{C}H}-R_2$ $R_1-X-\bigcirc-\bigcirc(F)-COO-\bigcirc(F,F)-COO-\overset{CF_3}{\underset{*}{C}H}-R_2$ $R_1-X-\bigcirc-\bigcirc(F)-COO-\bigcirc(F,F)-COO-\overset{CF_3}{\underset{*}{C}H}-R_2$ $R_1-X-\bigcirc(F)-\bigcirc-COO-\bigcirc(F,F)-COO-\overset{CF_3}{\underset{*}{C}H}-R_2$ $R_1-X-\bigcirc(F)-\bigcirc-COO-\bigcirc(F,F)-COO-\overset{CF_3}{\underset{*}{C}H}-R_2$ $R_1-X-\bigcirc(F,F)-\bigcirc-COO-\bigcirc(F)-COO-\overset{CF_3}{\underset{*}{C}H}-R_2$ -continued $R_1-X-\bigcirc-\bigcirc(F,F)-COO-\bigcirc(F)-COO-\overset{CF_3}{\underset{*}{C}H}-R_2$ $R_1-X-\bigcirc-\bigcirc(F,F)-COO-\bigcirc(F)-COO-\overset{CF_3}{\underset{*}{C}H}-R_2$ $R_1-X-\bigcirc-\bigcirc(F,F)-COO-\bigcirc(F)-COO-\overset{CF_3}{\underset{*}{C}H}-R_2$ $R_1-X-\bigcirc-\bigcirc(F,F)-COO-\bigcirc(F)-COO-\overset{CF_3}{\underset{*}{C}H}-R_2$ $R_1-X-\bigcirc-\bigcirc(F,F)-COO-\bigcirc(F)-COO-\overset{CF_3}{\underset{*}{C}H}-R_2$ $R_1-X-\bigcirc(F,F)-\bigcirc-COO-\bigcirc(F)-COO-\overset{CF_3}{\underset{*}{C}H}-R_2$ $R_1-X-\bigcirc-\bigcirc-COO-\bigcirc(F,F,F,F)-COO-\overset{CF_3}{\underset{*}{C}H}-R_2$ $R_1-X-\bigcirc-\bigcirc-COO-\bigcirc(Br)-COO-\overset{CF_3}{\underset{*}{C}H}-R_2$ $R_1-X-\bigcirc-\bigcirc-COO-\bigcirc(Br)-COO-\overset{CF_3}{\underset{*}{C}H}-R_2$ $R_1-X-\bigcirc-\bigcirc(Br)-COO-\bigcirc-COO-\overset{CF_3}{\underset{*}{C}H}-R_2$ $R_1-X-\bigcirc-\bigcirc(Br)-COO-\bigcirc-COO-\overset{CF_3}{\underset{*}{C}H}-R_2$ $R_1-X-\bigcirc(Br)-\bigcirc-COO-\bigcirc-COO-\overset{CF_3}{\underset{*}{C}H}-R_2$ $R_1-X-\bigcirc(Br)-\bigcirc-COO-\bigcirc-COO-\overset{CF_3}{\underset{*}{C}H}-R_2$ $R_1-X-\bigcirc(Br)-\bigcirc(Br)-COO-\bigcirc-COO-\overset{CF_3}{\underset{*}{C}H}-R_2$

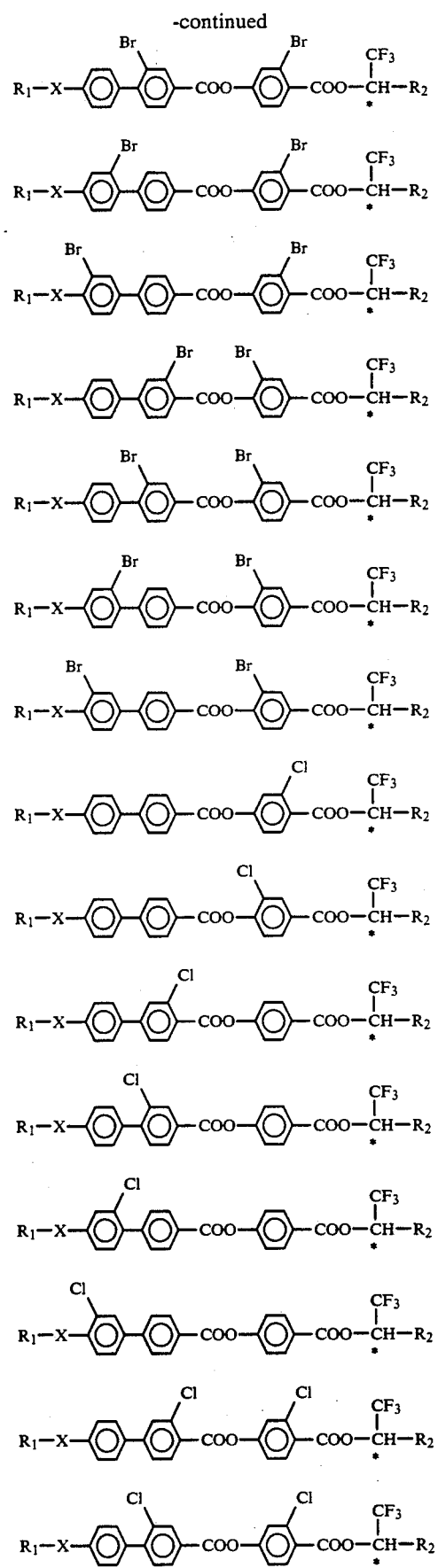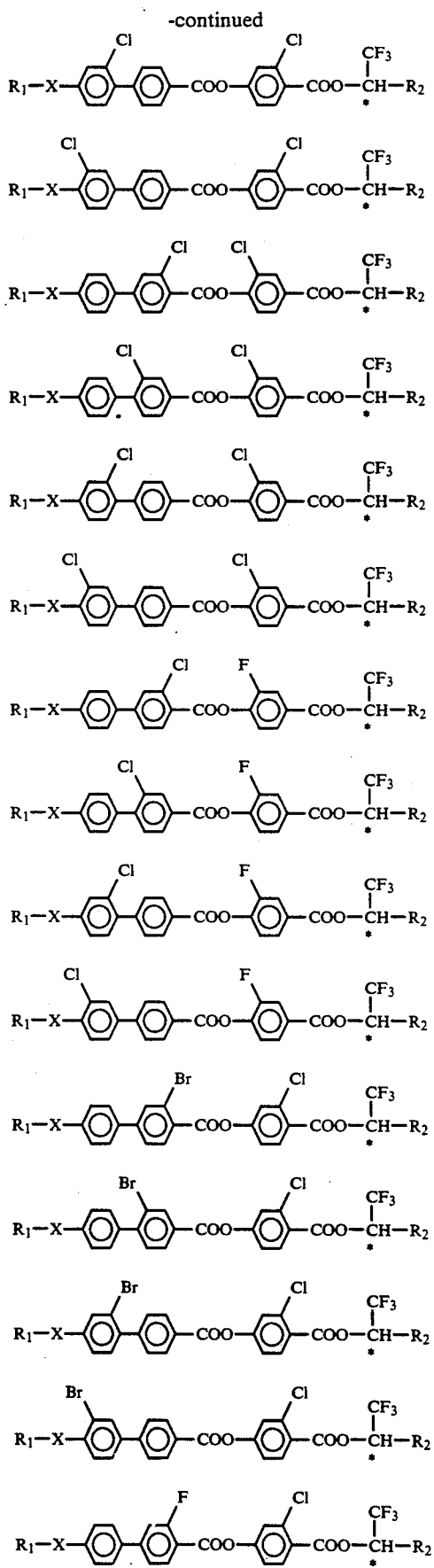

21
-continued

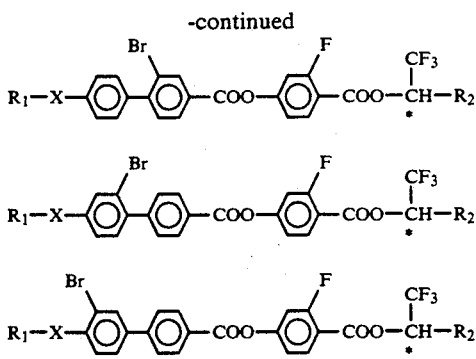

wherein $R_1$, $R_2$ and X are as defined above.

They may be used alone or a mixture thereof or a mixture with the other liquid crystal compounds having the similar structures thereto or not, thereby controlling properties of liquid crystals, obtained.

Appearance of tristable state depends on structures of compounds as follows:

a) $CF_3$ bonded to the asymmetric carbon is most critical; no appearance of tristable state when $CF_3$ is replaced by $CH_3$, and b) direction of esters is the same as that of

bonded to the asymmetric carbon.

One of processes for preparing the compounds is that 4-benzyloxybenzoic acid chloride is allowed to react with optically active 1,1,1-trifluoro-2-alkanols to prepare 1,1,1-trifluoro-2-alkyl 4-benzyloxybenzoate which is further hydrogenated to obtain 1,1,1-trifluoro-2-alkyl 4-hydroxybenzoate. The benzoate obtained is allowed to react with 2-fluoro-4-n-alkylcarbonyloxybenzoic acid in the presence of dicyclohexylcarbodiimide to prepare the desired optically active 4-(1,1,1-trifluoro-2-alkyloxycarbonyl)phenyl 2-fluoro-4-n-alkylcarbonyloxybenzoate.

In the accompanying drawings,

FIGS. 3-1 and 3-2 are hysteresises of liquid crystals showing a tristable state and a tetrastable state, respectively.

FIGS. 5 to 13 and 41-42 are electric responses of the present liquid crystals in an $S_A$ phase or a tristable state.

22

EXAMPLES

Example 1

Figure 1:
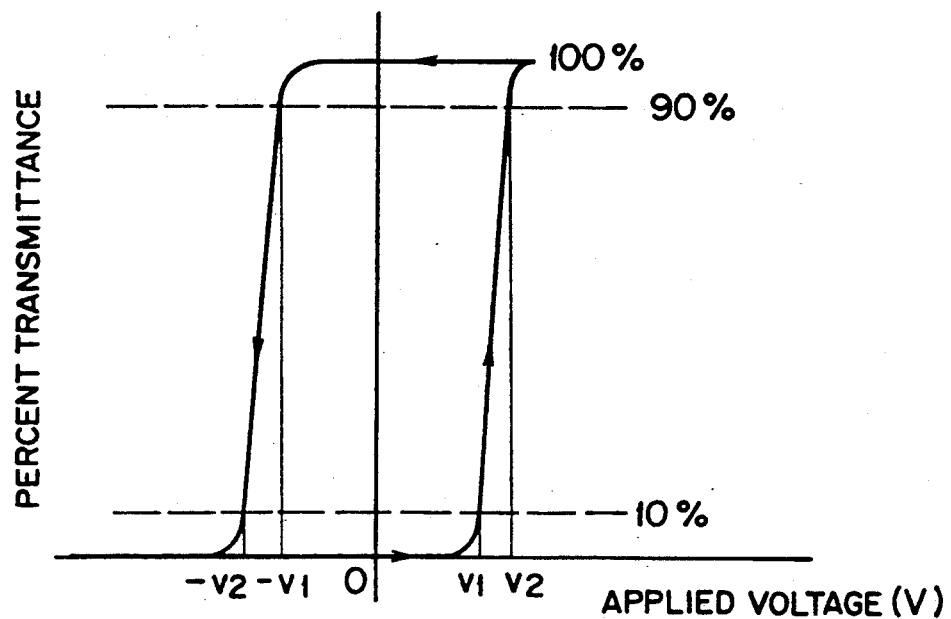
FIG. 1 is response wave to the electric field of liquid crystal showing an ideal bistable state.
Figure 2:
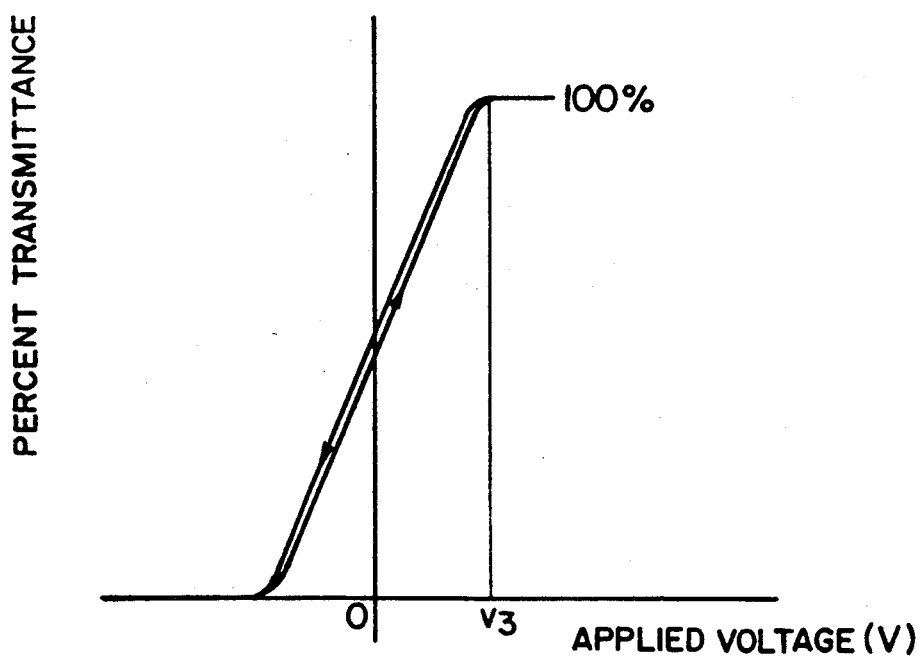
FIG. 2 is response wave to the electric field of liquid crystal conventionally obtained.
Figure 3B:
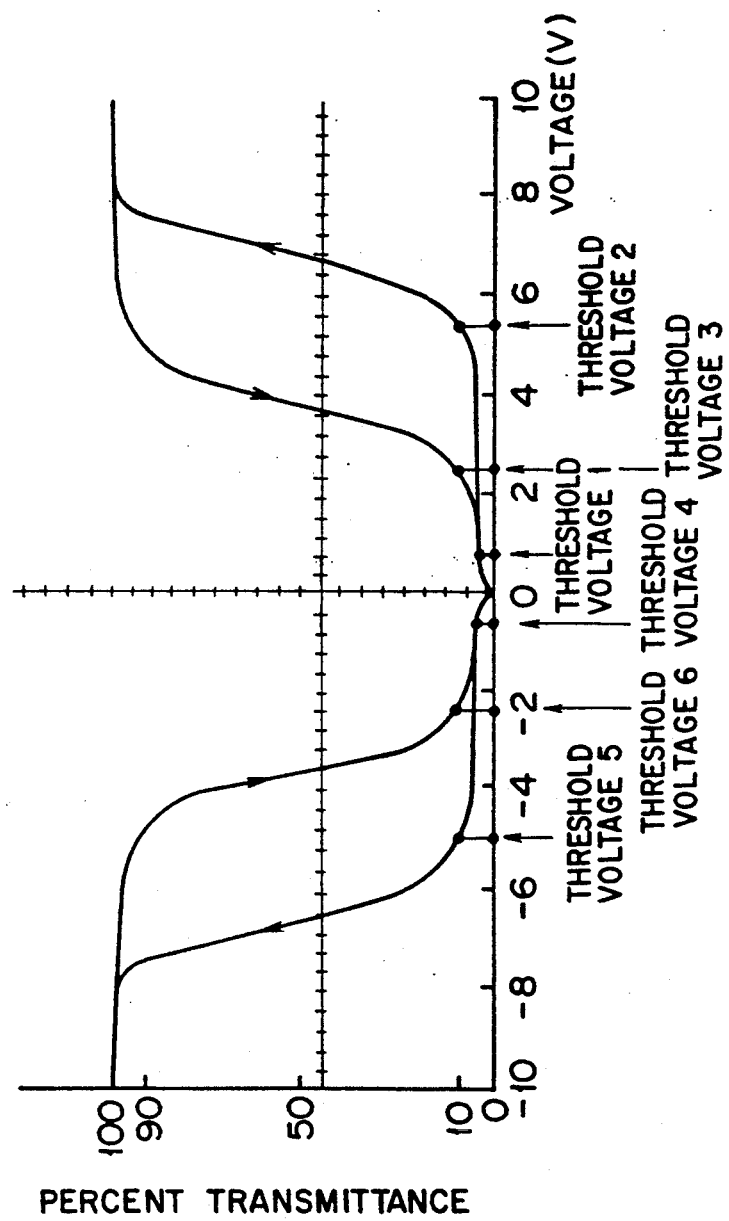
Figure 3C:
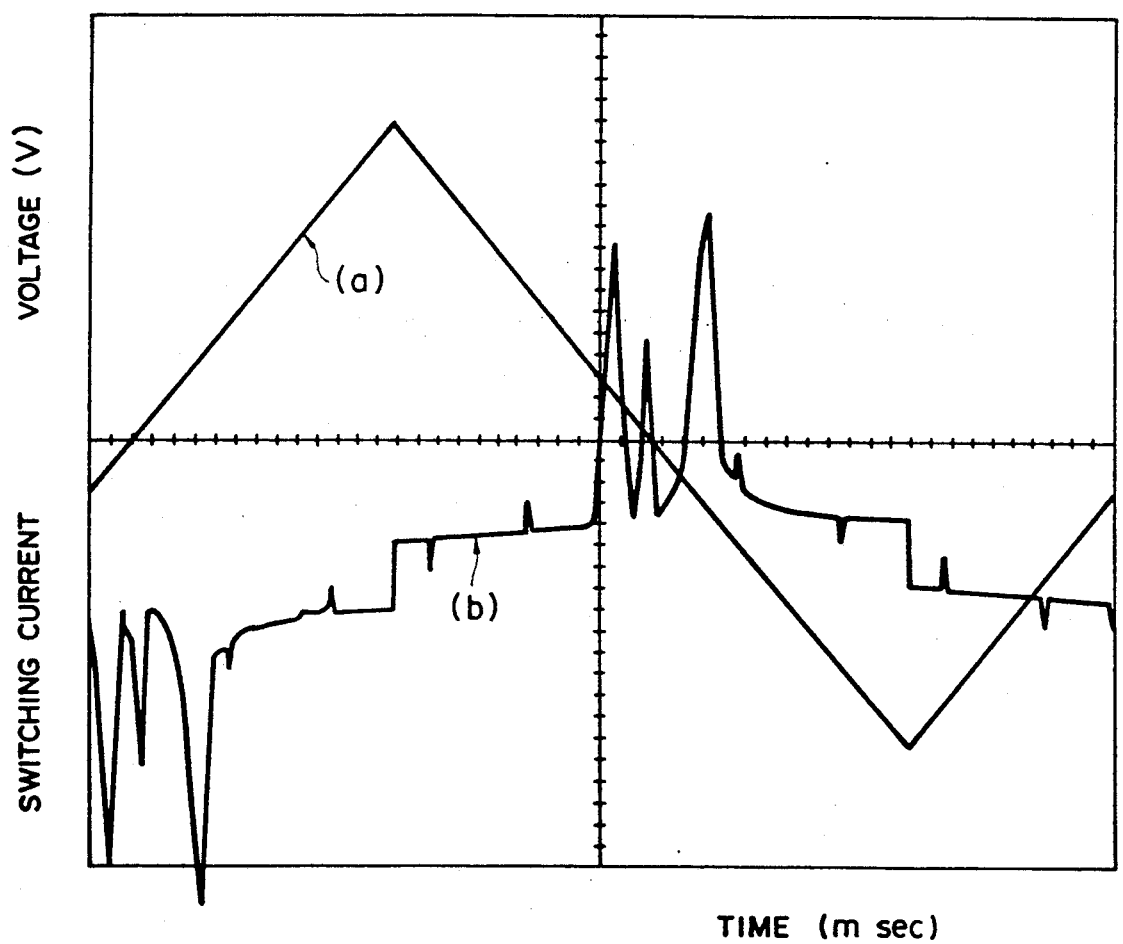
Figure 4A:
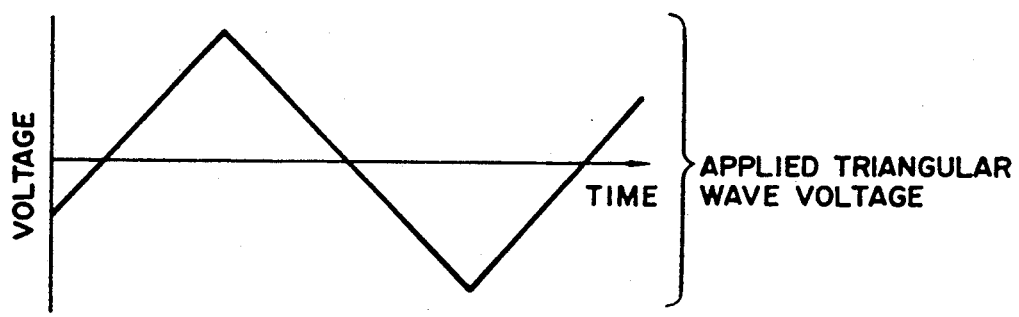
FIGS. 4A-4E are response waves to the electric field of liquid crystals showing bistable, tristable and tetrastable states, respectively.
Figure 4B:
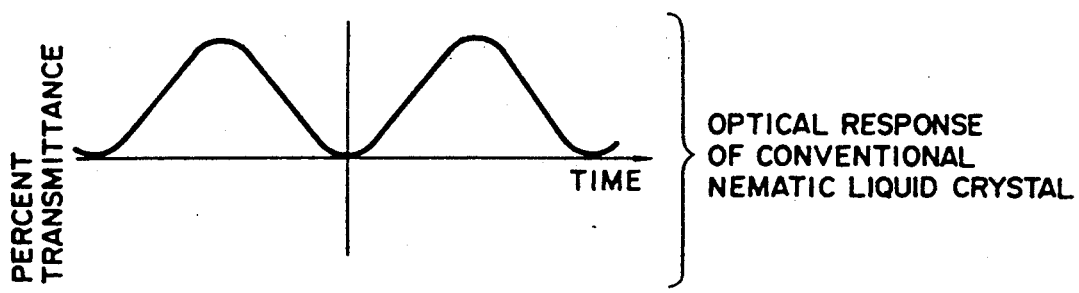
Figure 4C:
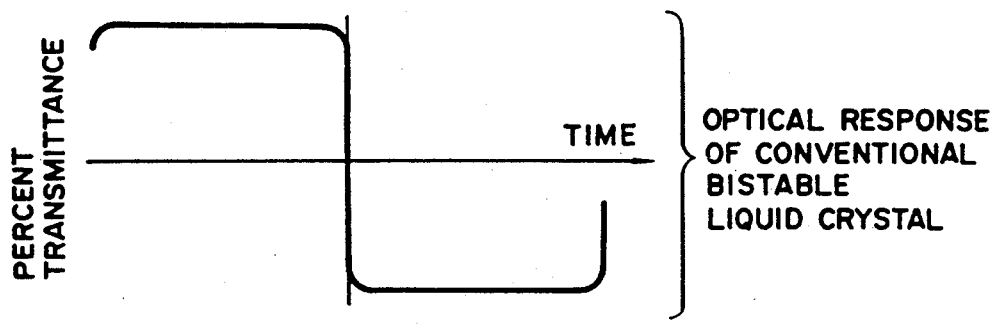
Figure 4D:
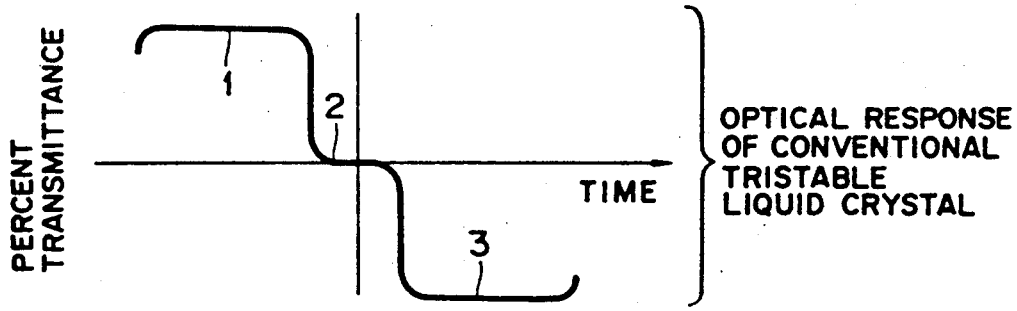
Figure 4E:
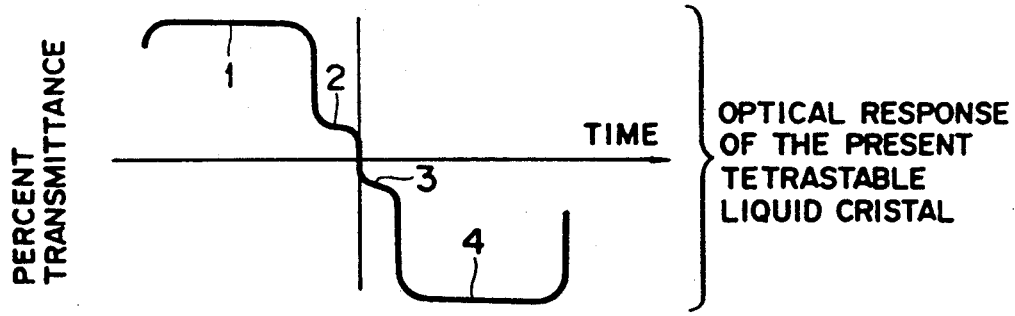

Synthesis of 4-(1,1,1-trifluoro-2-octyloxycarbonyl)phenyl 4-n-octyloxybiphenylcarboxylate (1) 1,1,1-Trifluoro-2-octyl-4-hydroxybenzoate To a solution of 4-benzyloxybenzoic acid chloride (1.1 g) in methylene chloride (20 ml) was slowly added under ice cooling a solution of optically active 1,1,1-trifluoro-2-octanol (0.74 g, $[\alpha]_D^{20} = +25.2$) and triethylamine (0.4 g) in methylene chloride (10 ml). After the solution was left to stand to reach room temperature, it was stirred for 12 hours. The solution was poured in ice water and was extracted with methylene chloride. The extracted layer was washed with dilute aqueous hydrochloric acid solution, water, 1N aqueous sodium carbonate solution and water, in the order, and dehydrated over anhydrous magnesium sulfate. The solution was distilled under reduced pressure to remove the solvent until a crude product was obtained. The product was subjected to silica-gel column chromatography to obtain 1,1,1-trifluoro-2-octyl 4-benzyloxybenzoate (0.73 g).

The benzoate and 10 % palladium carried on carbon (0.1 g) were added to ethanol and the mixture was subjected to de-benzyl reaction under a hydrogen atmosphere until the titled compound (0.53 g) was obtained.

(2) 4-(1,1,1-Trifluoro-2-octyloxycarbonyl)phenyl 4-n-octyloxybiphenyl-4'-carboxylate To a mixture of the 1,1,1-trifluoro-2-octyl 4-hydroxybenzoate prepared above (0.53 g) and triethylamine (0.18 g) in methylene chloride (10 ml) was slowly added c under ice cooling a solution of 4-n-octyloxybiphenyl-4'-carboxylic acid chloride (0.73 g) in methylene chloride (10 ml). After the mixture was left to stand until it reached room temperature, it was stirred overnight. The mixture was poured in water and extracted with methylene chloride. The extracted layer was washed with dilute aqueous hydrochloric acid solution, water, 1N aqueous sodium carbonate solution and water, in this order, and dehydrated over anhydrous magnesium sulfate. After the solution was distilled under reduced pressure to remove the solvent, the residue was purified by silica-gel column chromatography to obtain the titled compound (0.4 g, $[\alpha]_D^{20} = +32.2$).

The product showed mesomorphism and had phase transition temperatures (° C) which were observed under a polyrization microscope using a hot stage as follows:

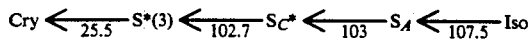

$S^*(3)$ = an antiferroelectric phase of tristable state

Figure 14:
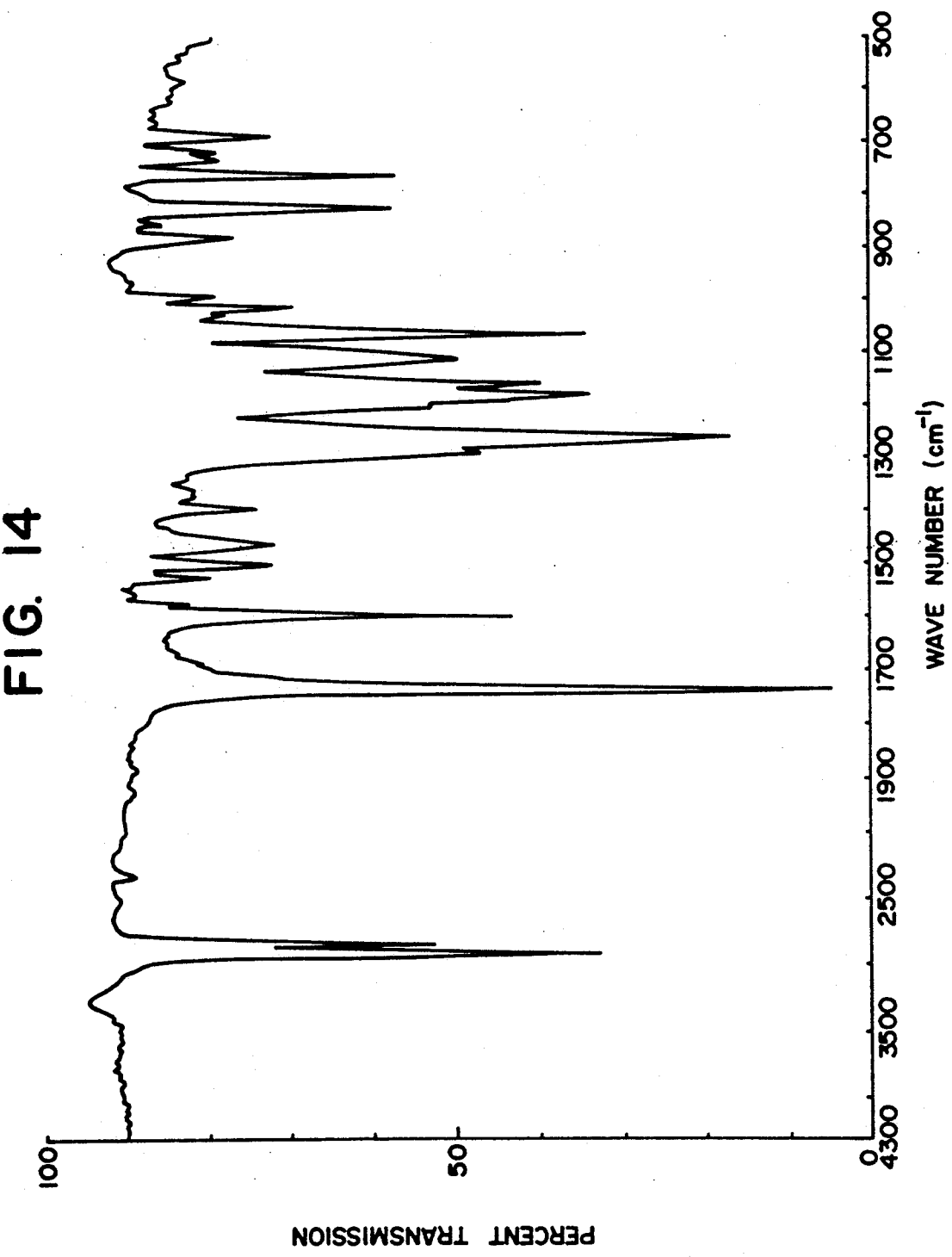
FIGS. 14-40 are IR spectrums of the present liquid crystals.

FIG. 14 is an 1 R spectrum (KBr) of the titled compound.

Example 2

Synthesis of 4-(1-monofluoro-2-octyloxycarbonyl)phenyl 4-octylbiphenyl-4'-carboxylate

(1) 1-Monofluoro-2-decyl 4-hydroxybenzoate

To a solution of 4-benzyloxybenzoic acid chloride (1.3 g) in methylene chloride (25 ml) was slowly added under ice cooling a solution of optically active 1-monofluoro-2-decanol (1.0 g) and triethylamine (0.5 g) in methylene chloride (25 ml). The mixture was left to stand until it reached room temperature. After the mixture was stirred for 12 hours, it was poured in ice water. The mixture was extracted with methylene chloride and the extracted layer was washed with dilute aqueous hydrochloric acid solution, water, 1N aqueous sodium carbonate solution and water, in this order. The solution was dehydrated over anhydrous magnesium sulfate. The solution was distilled under reduced pressure to remove the solvent until a crude product was obtained.

The product was subjected to silica-gel column chromatography to obtain 1-monofluoro-2-decyl 4-benzyloxybenzoate (0.78 g).

The benzoate and 10 % palladium carried on carbon (0.13 g) were added to ethanol and the mixture was subjected to de-benzylation under a hydrogen atmosphere until the titled compound (0.6 g) was obtained.

(2) 4-(1-Monofluoro-2-decyloxycarbonyl)phenyl 4-n-octylbiphenyl-4'-carboxylate A mixture of the benzoate prepared in (1) above (0.6 g) and triethylamine (0.2 g) in methylene chloride (25 ml) was slowly added under ice cooling to a solution of 4-n-octyl-4'-biphenylcarboxylic acid chloride (0.76 g) in methylene chloride (25 ml).

The mixture was left to stand until it reached room temperature and was stirred overnight. The mixture was poured in water and extracted with methylene chloride. The extracted layer was washed with dilute aqueous hydrochloric acid solution, water, 1N aqueous sodium carbonate solution and water, in the order. The mixture was dehydrated over anhydrous magnesium sulfate and was distilled under reduced pressure to remove the solvent. The residue was purified by silica-gel column chromatography to obtain the titled compound (0.8 g, $[\alpha]_D^{20} = -20.0°$ ).

The compound showed mesomorphism and had phase transition temperatures (° C.) which were observed under a polarization microscope using a hot stage as follows:

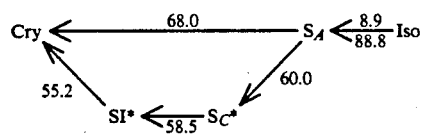

Figure 15:
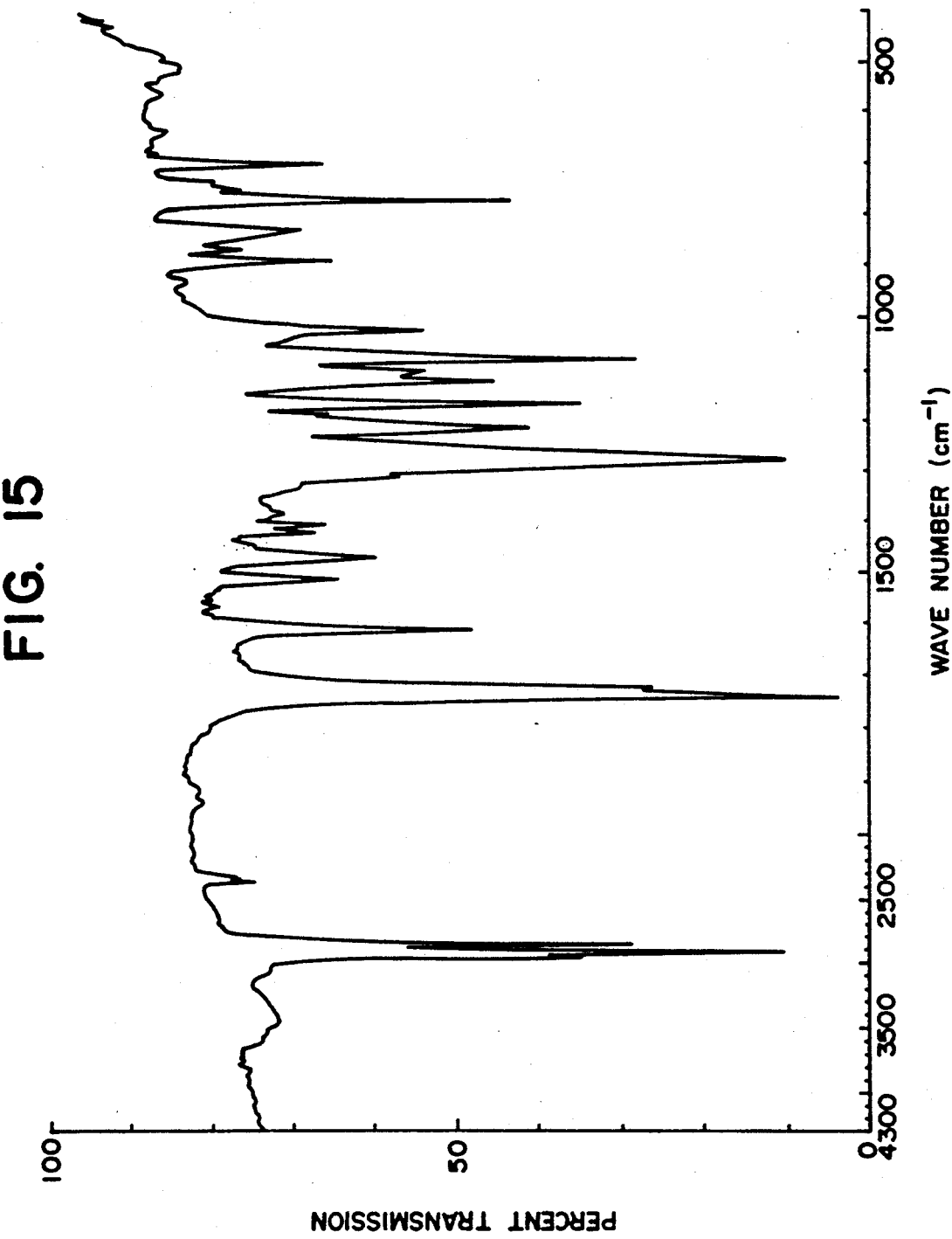

FIG. 15 is an IR spectrum (KBr) of the titled product.

Example 3

Synthesis of 4-(1-difluoro-2-octyloxycarbonyl)phenyl 4-octylbiphenyl-4'-carboxylate Example 2 was repeated except that 1,1-difluoro-2-decyl alcohol was used in place of the 1-monofluoro-2-decanol to obtain the titled compound having $[\alpha]_D^{20} = +15.3°$ .

The product compound showed mesomorphism and had phase transition temperatures (° C) which were observed under a polarization microscope using a hot stage as

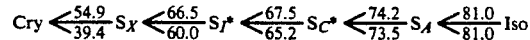

$S_X$: higher state having field response

Figure 16:
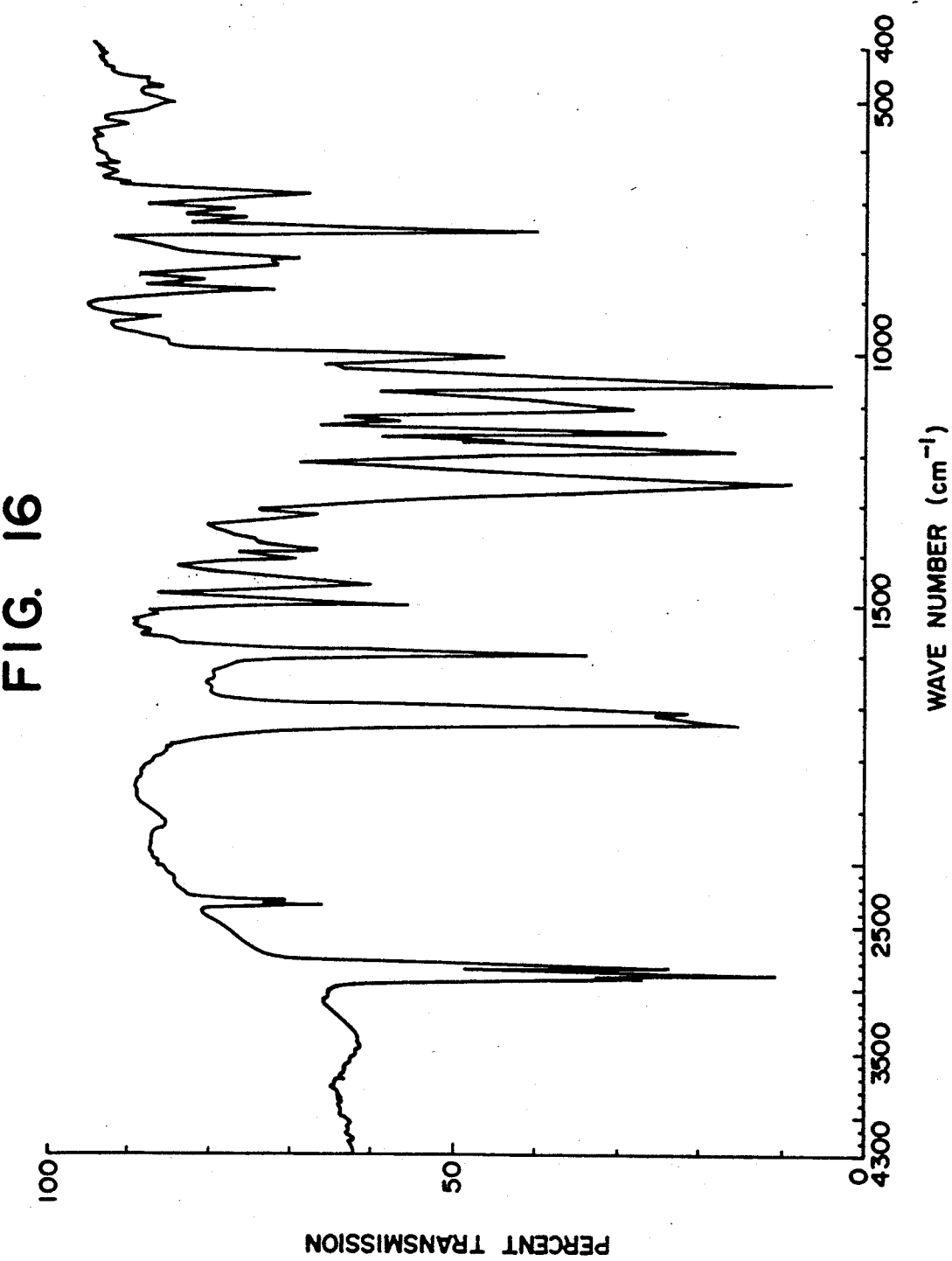

FIG. 16 is an IR spectrum (KBr) of the titled product.

Example 4

Synthesis of 4-(1-monofluoro-2-decyloxycarbonyl)phenyl 4-octyloxybiphenyl-4'-carboxylate

(1) 1-monofluoro-2-decyl 4-hydroxybenzoate

To a solution of 4-benzyloxybenzoic acid chloride (1.3 g) in methylene chloride (25 ml) was slowly added under ice cooling a solution of optically active 1-monofluoro-2-decanol (1.0g, $[\alpha]_D^{20} = -7.2$) and triethylamine (0.5 g) in methylene chloride (25 ml). The mixture was left to stand until it reached room temperature and stirred for 12 hours. The mixture was poured in ice water and extracted with methylene chloride. The extracted layer was washed with dilute aqueous hydrochloric acid solution, water, 1N aqueous sodium carbonate solution and water, in this order, and dehydrated over anhydrous magnesium sulfate. The solution was distilled under reduced pressure to remove the solvent until a crude product was obtained. The product was subjected to silica-gel column chromatography to obtain 1-monofluoro-2-decyl 4-benzyloxybenzoate (0.78 g). The benzoate and 10% palladium carried on carbon (0.13 g) were added to ethanol and then subjected to de-benzylation under a hydrogen atmosphere to obtain 1-monofluoro-2-decyl-4-hydroxybenzoate (0.6 g).

(2) 4-(1-Monofluoro-2-decyloxycarbonyl)phenyl 4-n-octyloxybiphenyl-4'-carboxylate The hydroxybenzoate obtained in (1) (0.6 g) and triethylamine (0.2 g) were added to methylene chloride (25 ml). To the mixture was slowly added under ice cooling a solution of 4-n-octyloxybiphenyl-4'-carboxylic acid chloride (0.8 g) in methylane chloride (25 ml). The mixture was left to stand until it reached room temperature and stirred overnight. The mixture was poured in water and extracted with methylane chloride. The extracted layer was washed with dilute aqueous hydrochloric acid solution, water, 1N aqueous sodium carbonate solution and water, in this order, and dehydrated over anhydrous magnesium sulfate. After the solution was distilled under reduced pressure to remove the solvent, purification was made by silica-gel column chromatography to obtain the titled compound (0.9 g, $[\alpha]_D^{20} = -18.8$).

The product showed mesomorphism and had phase transition temperatures (° C.) which was observed under a polarization microscope using a hot stage as follows:

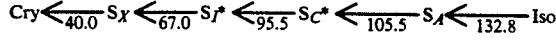

Figure 17:
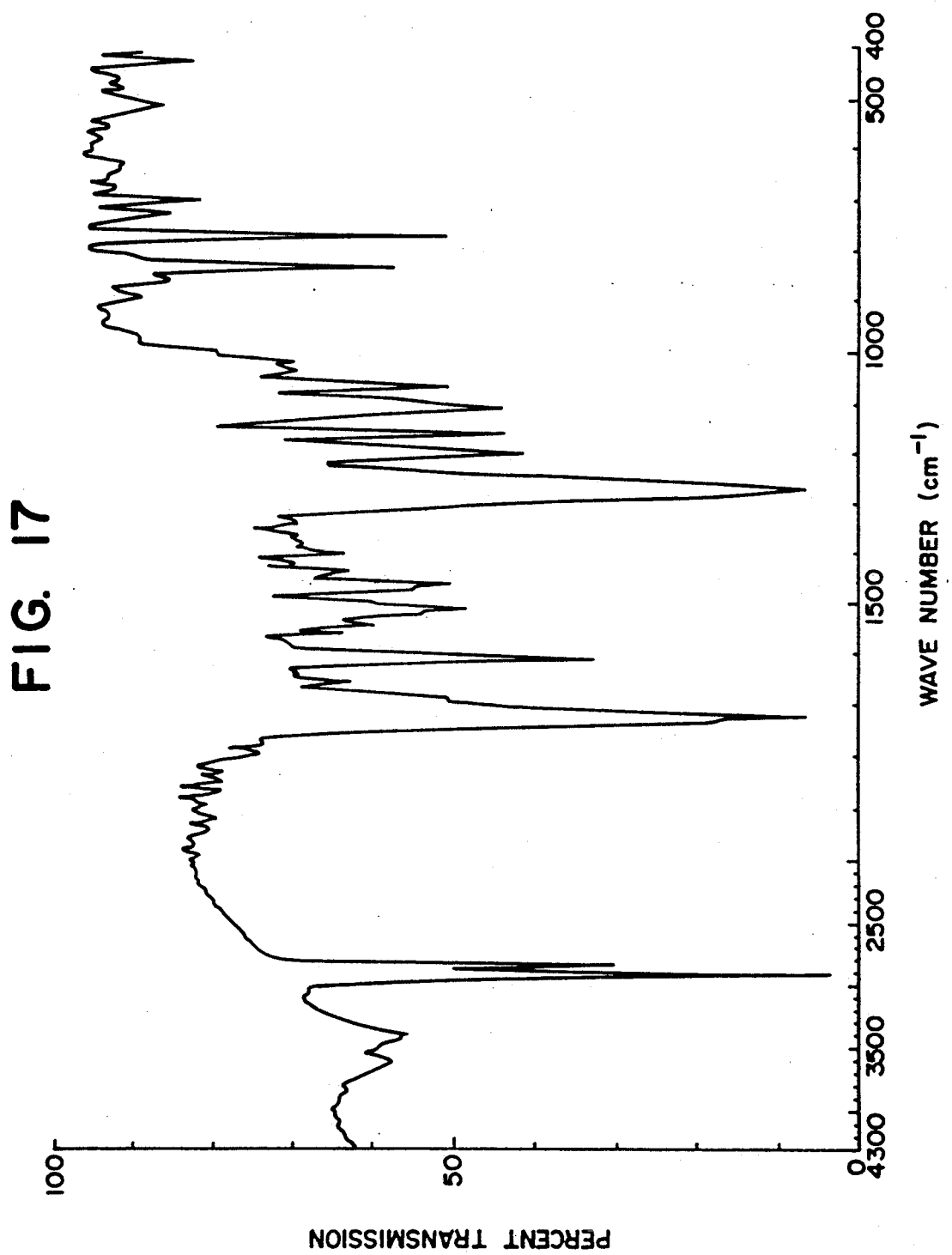

FIG. 17 shows an IR spectrum (KBr) of the titled compound.

Example 5

Synthesis of 4-(1,1-difluoro-2-decyloxycarbonyl)phenyl 4-octyloxybiphenyl-4'-carboxylate Example 4 was repeated except 1,1-difluoro-2-decyl alcohol was used in place of the 1-monofluoro-2-decanol to obtain the titled compound ($[\alpha]_D^{25} = +8.3$).

The compound showed mesomorphism and had phase transition temperatures (° C.) which were observed under a polarization microscope using a hot stage as follows:

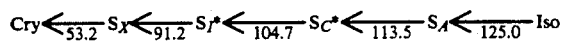

Figure 18:
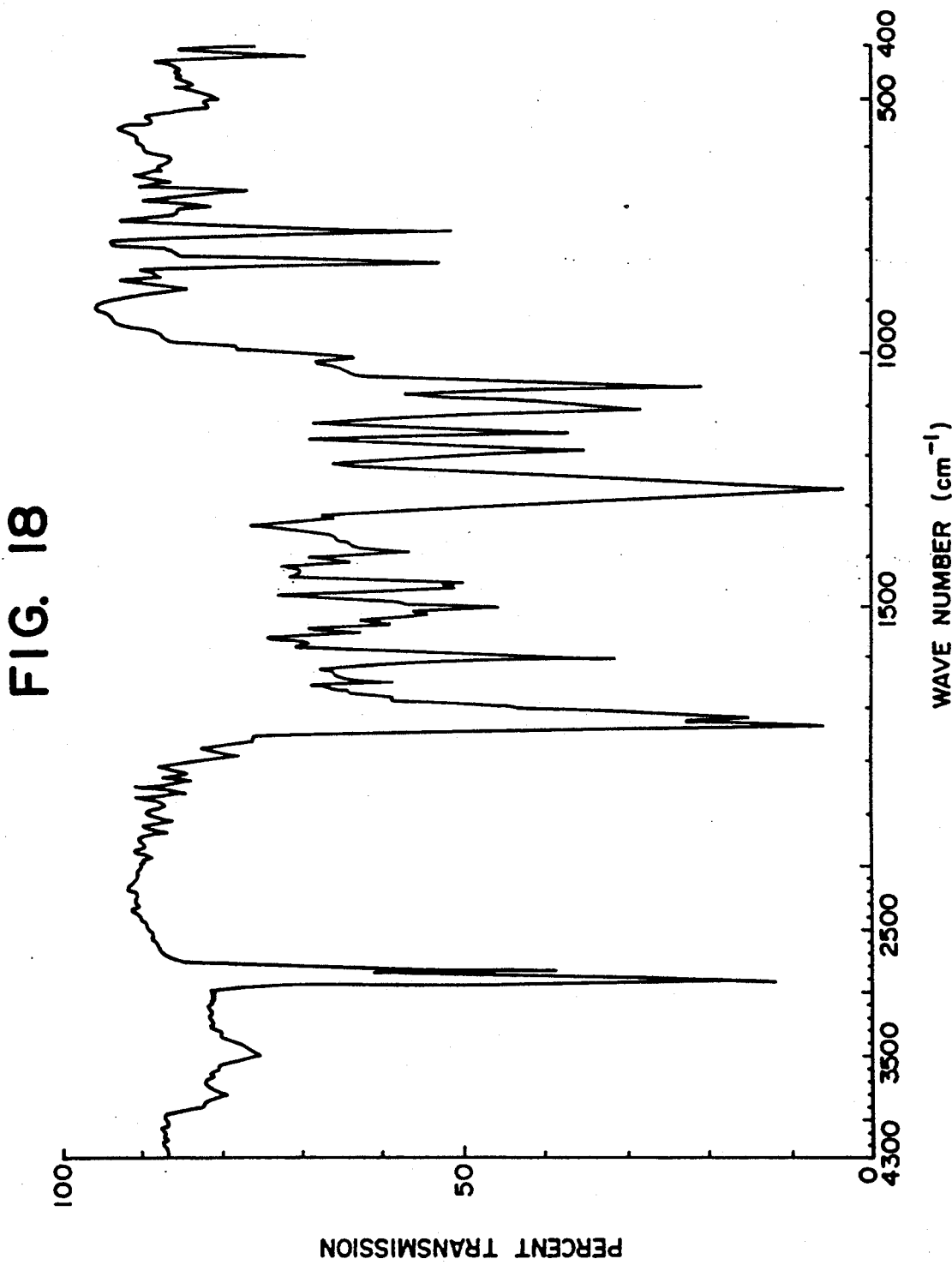

FIG. 18 is an IR spectrum (KBr) of the titled compound.

Example 6

Synthesis of 1-monofluoro-2-decyl 4-octyloxybiphenyl-4'-carboxylate

To a solution of optically active 1-monofluoro-2-decyl alcohol (0.1 g) and triethylamine (0.06 g) in methylene chloride (10 ml) was slowly added under ice cooling a solution of 4-n-octyloxybiphenyl-4'-carboxylic acid chloride (0.22 g) in methylene chloride (10 ml). The mixture was left to stand until it reached room temperature and stirred overnight. The mixture was poured in water and extracted with methylene chloride. The solution extracted layer was washed with dilute aqueous hydrochloric acid solution, water, 1N aqueous sodium carbonate solution and water, in this order, and dehydrated over anhydrous magnesium sulfate. After the solution was distilled under reduced pressure to remove the solvent, purification was made by silica-gel column chromatography to obtain the titled compound (0.16 g).

Figure 19:
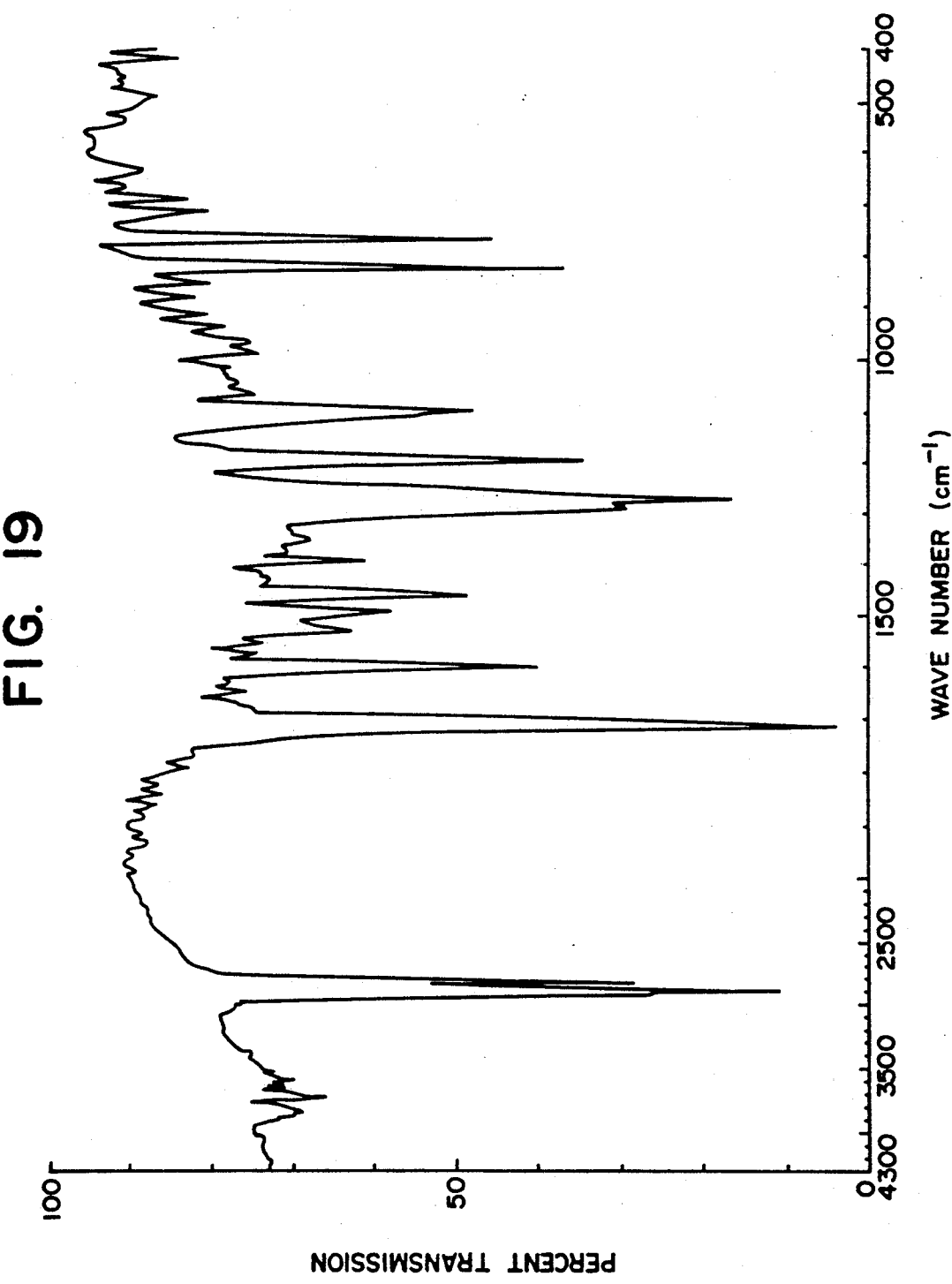

The compound showed isotropic phase until 34.4° C. which was observed under a polarization microscope using a hot stage. FIG. 19 is an IR spectrum of the titled compound.

Example 7

Synthesis of 1,1-difluoro-2-decyl-4-octyloxybiphenyl-4'-carboxylate

Example 6 was repeated except that optically active 1,1-difluoro-2-decyl alcohol was used in place of the 1-monofluoro-2-decyl alcohol.

Figure 20:
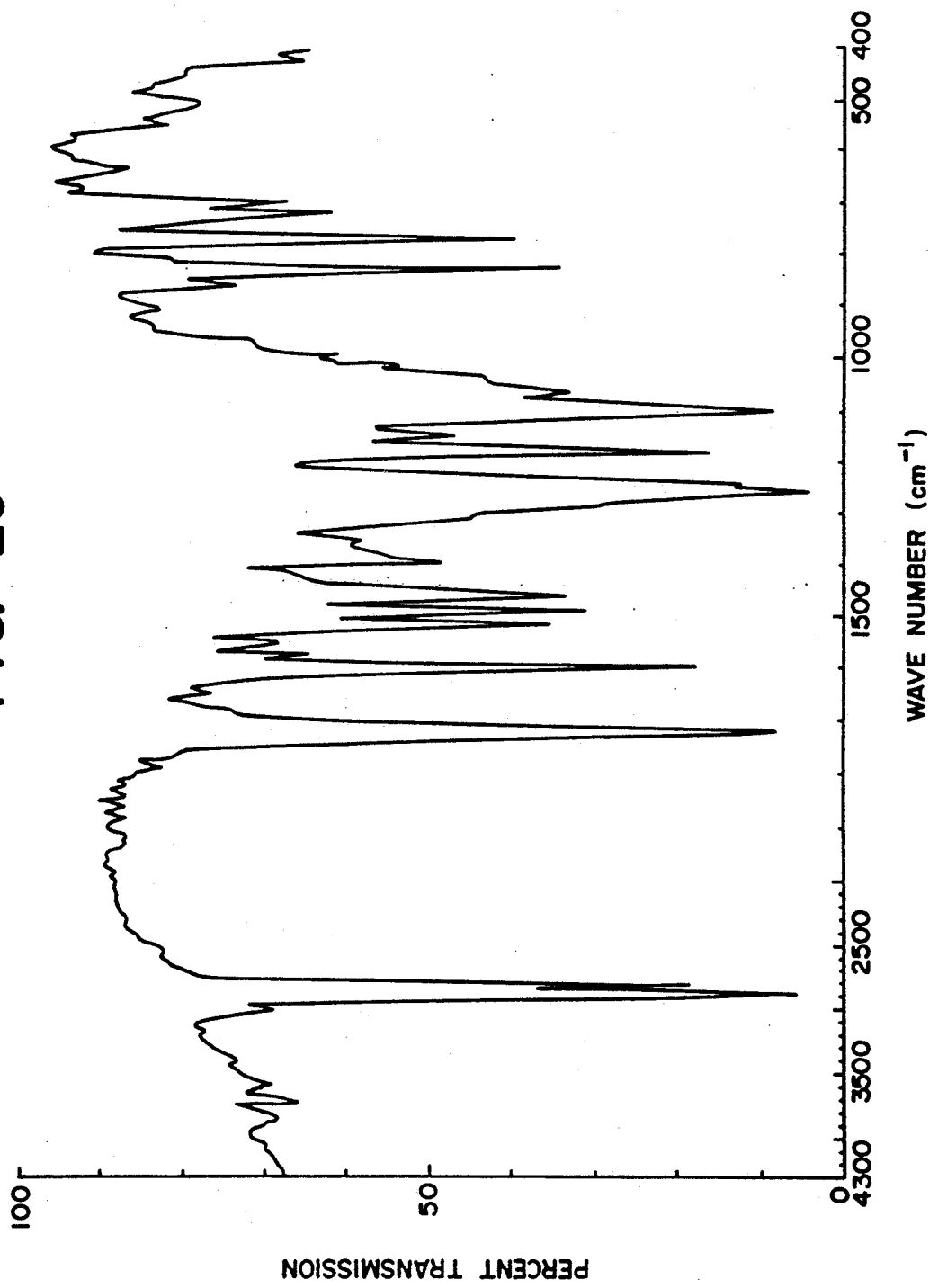

The compound obtained showed isotropic phase 30 until -30° C. which was observed under a polarization microscope with a hot stage. FIG. 20 is an IR spectrum (KBr) of the titled compound.

Example 8

Synthesis of 4-(1-monofluoro-2-decyloxycarbonyl)phenyl 4-octyloxybenzoate (1) 1-Monofluoro-2-decyl 4-hydroxybenzoate To a solution of 4-benzyloxybenzoic acid chloride (0.19 g) in methylene chloride (10 ml) was slowly added under ice cooling a solution of optically active 1-monofluoro-2-decanol (0.14 g) and triethylamine (0.07 g) in methylene chloride (10 ml). The mixture was left to stand until it reached room temperature and stirred for 12 hours. The mixture was poured in ice water and extracted with methylene chloride. The extracted layer was washed with dilute aqueous hydrochloric acid solution, water, 1 N aqueous sodium carbonate solution and water, in this order, and dehydrated over anhydrous magnesium sulfate. The solution was distilled under reduced pressure to remove the solvent until a crude product was obtained. The product was subjected to silica-gel column chromatography to obtain 1-monofluoro-2-decyl-4-benzyloxybenzoate (0.13 g).

The benzoate and 10 % palladium carried on carbon (0.015 g) were added to ethanol and the mixture was subjected to de-benzylation in a hydrogen atmosphere to obtain 1-monofluoro-2-decyl 4-hydroxybenzoate (0.1 g).

(2) 4-(1-Monofluoro-2-decyloxycarbonyl)phenyl 4-octyloxybenzoate

To a solution of the 1-monofluoro-2-decyl 4-hydroxybenzoate prepared in (1) (0.1 g) and triethylamine (0.04 g) in methylene chloride (10 ml) was slowly added under ice cooling a solution of 4-n-octyloxybenzoic acid chloride (0.1 g) in methylene chloride (10 ml). The mixture was left to stand until it reached room temperature and stirred overnight. The mixture was poured in water and extracted with methylene chloride. The extracted layer was washed with dilute aqueous hydrochloric acid solution, water, 1N aqueous sodium carbonate solution and water, in this order, and dehydrated over anhydrous magnesium sulfate. After the solution was distilled under reduced pressure to remove the solvent, the product was purified by silica-gel column chromatography to obtain the titled compound (0.13 g).

Figure 21:
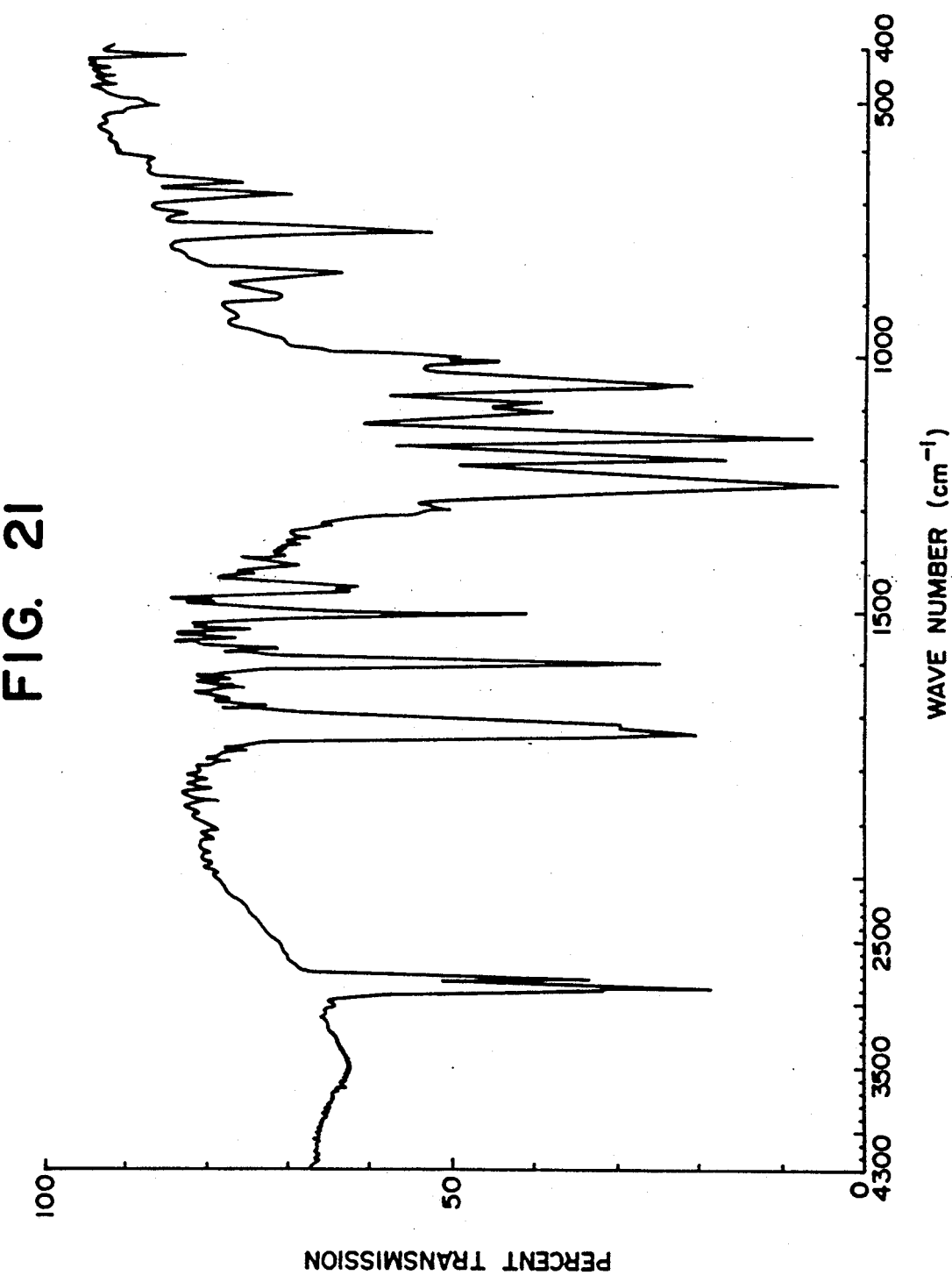

The product showed isotropic phase until 30° C. which was observed under a polarization microscope with a hot stage. FIG. 21 is an IR spectrum (KBr) of the titled compound.

Example 9

Synthesis of 4-(1,1-difluoro-2-decyloxycarbonyl)phenyl 4-octyloxybenzoate

Example 8 was repeated except that optically active 1,1-difluoro-2-decyl alcohol was used in place of the 1-monofluoro-2-decanol to prepare the titled compound.

Figure 22:
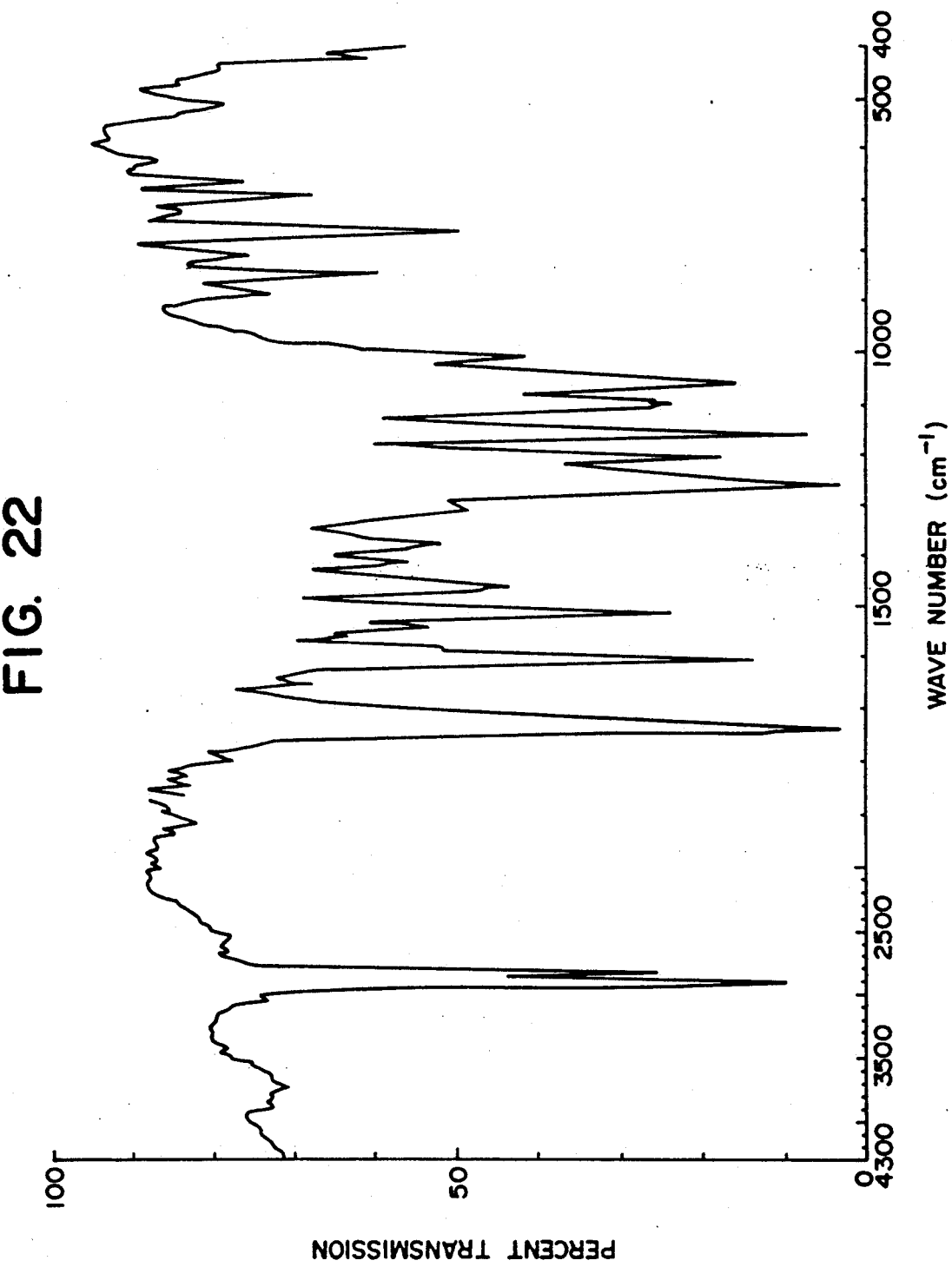

The compound showed mesomorphism until -30° C. which was observed under a polarization microscope using a hot stage. FIG. 22 is an IR spectrum (KBr) of the titled compound.

Example 10

Synthesis of 4-(1,1,1,2,2-pentafluoro-3-undecyloxycarbonyl)phenyl 4-octyloxybiphenyl-4'-carboxylate Example 4 was repeated except optically active 1,1,1,2,2-pentafluoro-3-undecyl alcohol was used in place of the 1-monofluoro-2-decanol to obtain the titled compound.

The compound showed mesomorphism and had phase transition temperatures (° C.) which were observed under a polarization microscope using a hot stage as follows:

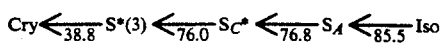

Figure 23:
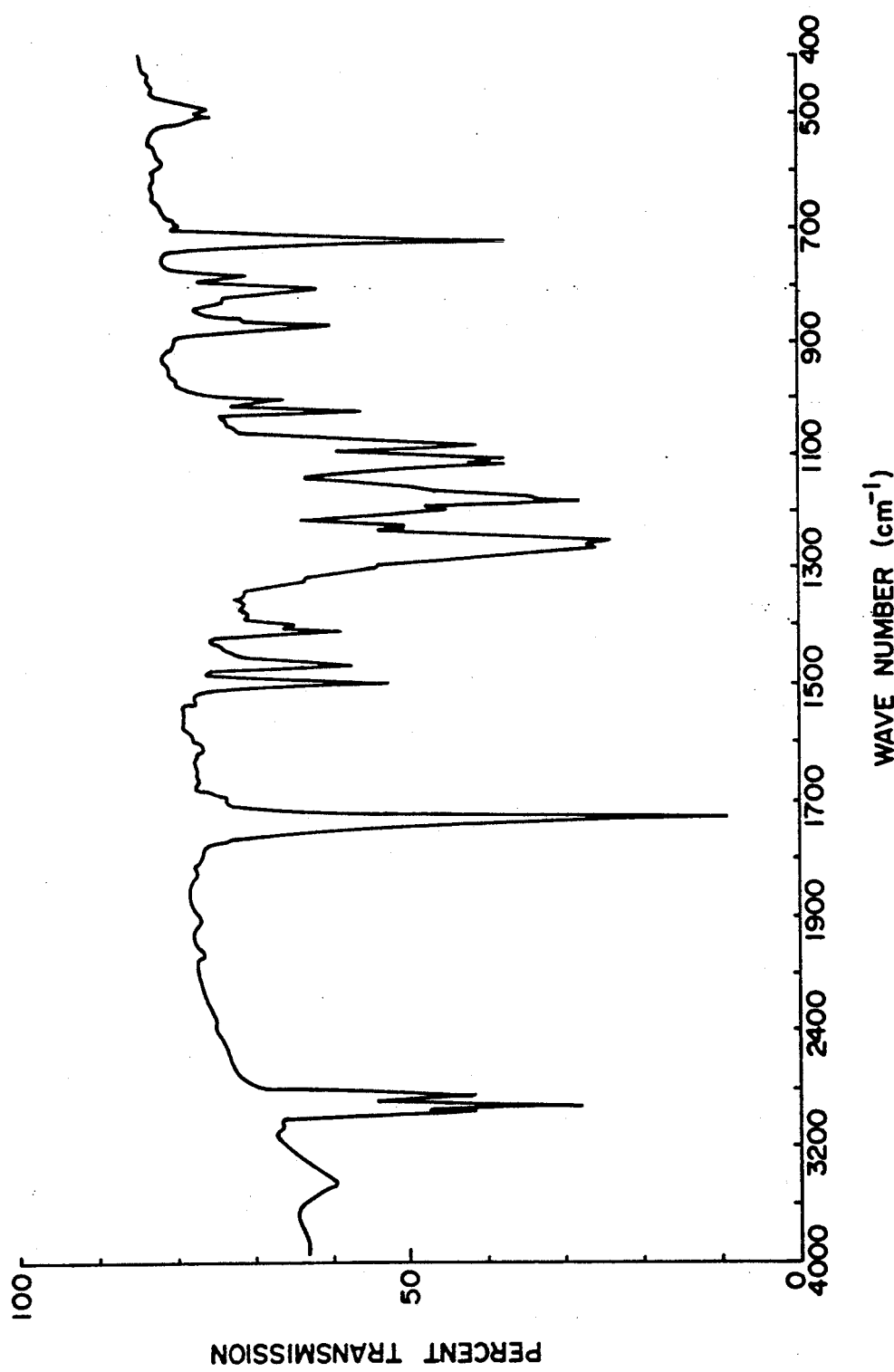

FIG. 23 is an IR spectrum (KBr) of the titled compound.

Example 11

Synthesis of
4-(1-chloro-1,1-difluoro-4-phenyl-2-butyloxycarbonyl)-
phenyl 4-n-octyloxybiphenyl-4'-carboxylate Example 10 was repeated except that optically active 1-chloro-1,1-difluoro-4-phenyl-2-butanol was used in place of the 1,1,1,2,2-pentafluoro-3-undecanol to prepare the titled compound.

The compound showed mesomorphism and had phase transition temperatures (° C.) which were observed under a polarization microscope using a hot stage as follows:

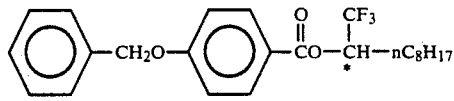

Figure 24:
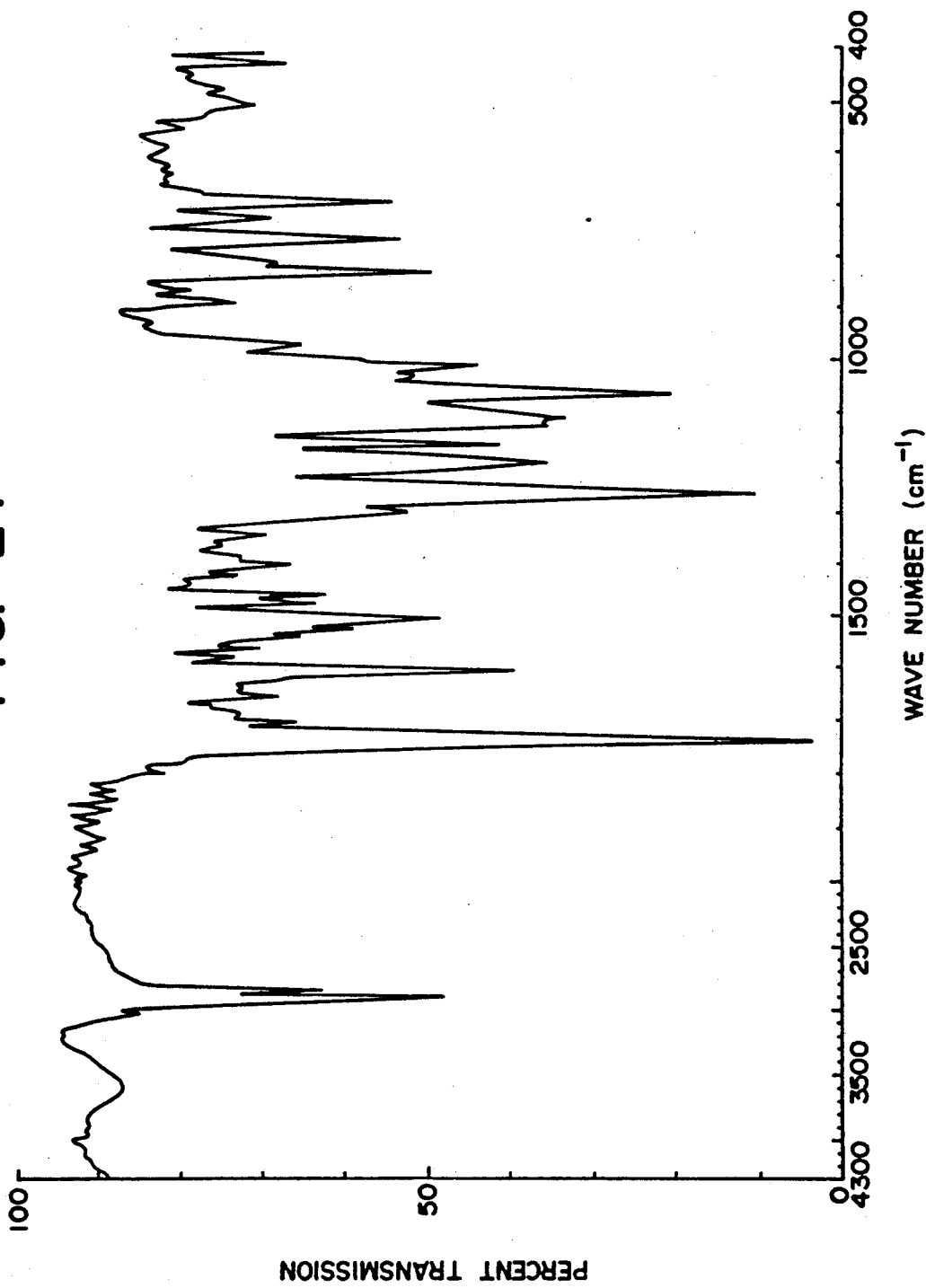

FIG. 24 is an IR spectrum (KBr) of the titled compound.

Example 12

(1) Synthesis of 1,1,1-trifluoro-2-decyl 4-benzyloxybenzoate

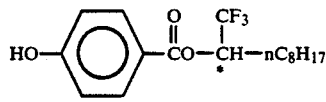

To a solution of 4-benzyloxybenzoic acid chloride (1.23 g) in methylene chloride (10 ml) was slowly added under ice cooling a solution of optically active 1,1,1-trifluoro-2-decanol (0.96 g), dimethylaminopyridine (0.55 g) and triethylamine (0.48 g) in methylane chloride (20 ml). The mixture was left to stand until it reached room temperature and allowed to react overnight. The mixture was poured in ice water and extracted with methylene chloride. The extracted layer was washed with dilute aqueous hydrochloric acid solution, water, 1N aqueous sodium carbonate solution and water in this order, and was dried over anhydrous magnesium sulfate. After the solution was distilled to remove the solvent, the crude product thus obtained was purified by toluene-silica-gel column chromatography and recrystallized from ethanol to obtain the titled compound (1.84 g).

(2) Synthesis of 1,1,1-trifluoro-2-decyl 4-hydroxybenzoate

To a solution of the compound obtained in (1) above in ethanol (15 ml) was added 10% Pd carried on carbon (0.36 g), and the mixture was hydrogenated under a hydrogen atmosphere to obtain the titled compound (1.43 g).

(3) Synthesis of 4-n-decanoyloxybenzoic acid

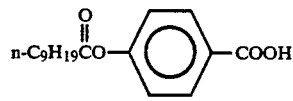

To a solution of p-hydroxybenzoic acid (3 g) and triethylamine (2.4 g) in dichloromethane (30 ml) were added decanoyl chloride (4.3 g) and dimethylaminopyridine (0.2 g). The mixture was stirred at room temperature for about 20 hours. After dilute aqueous hydrochloric acid solution was added to the mixture, an organic layer was separated by a funnel. After the solution was distilled to remove the solvent, the residue was washed with n-hexane and dried to obtain the titled compound (about 5 g).

(4) Synthesis of
4-(1,1,1-trifluoro-2-decyloxycarbonyl)phenyl
4-n-decanoyloxybenzoate

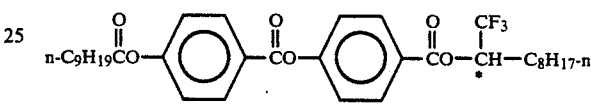

Figure 25:
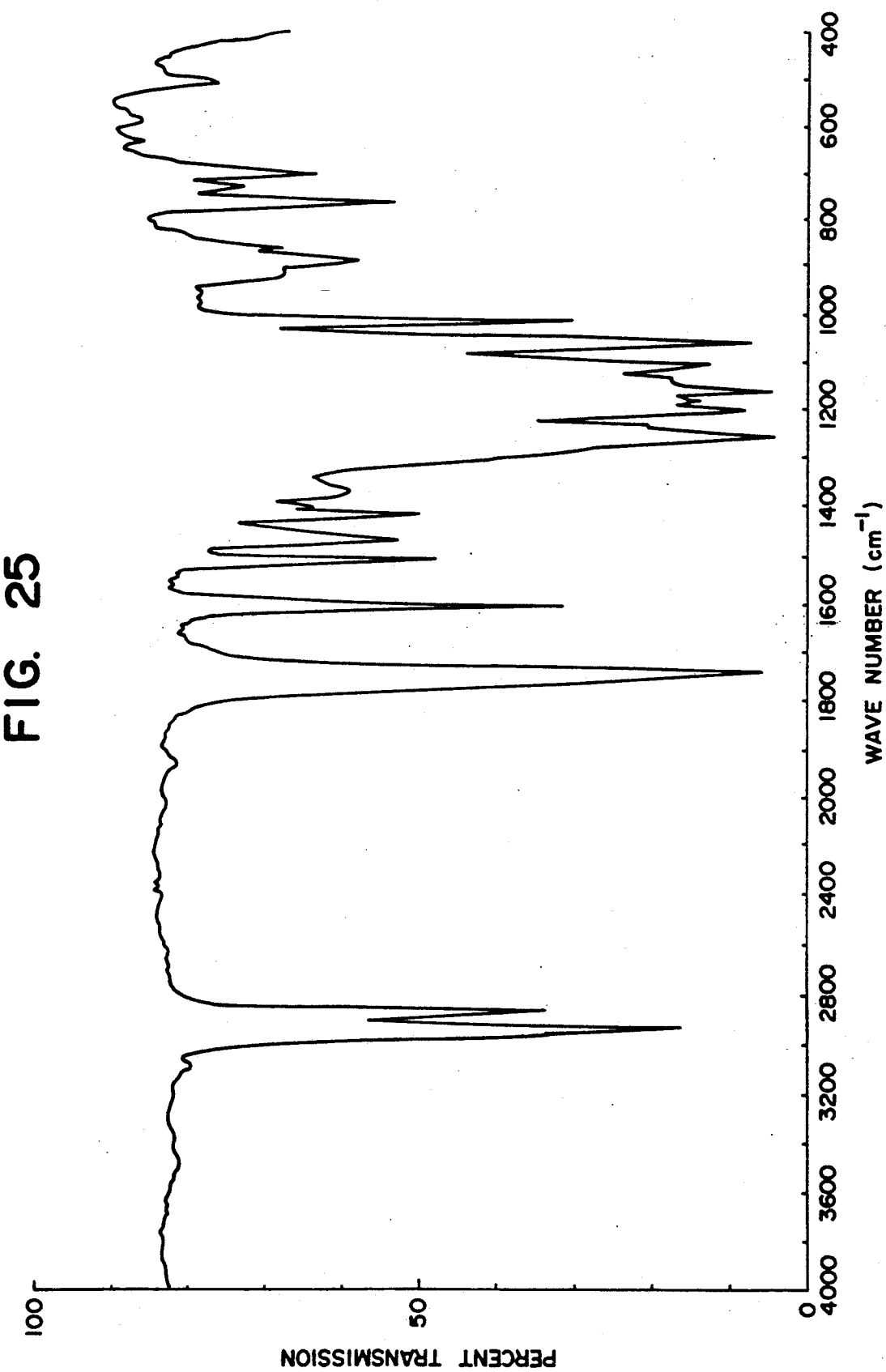

To a solution of the 4-n-decanoyloxybenzoic acid (0.4 g) obtained in (3) and the 1,1,1-trifluoro-2-decyl 4-hydroxybenzoate (0.4 g) obtained in (2) in tetrahydrofuran (about 30 ml) were added dicyclohexylcarbodiimide (0.32 g) and dimethylaminopyridine (0.01 g). The mixture was stirred at room temperature for about 20 hours and was distilled to remove the solvent. The residue was dissolved in dichloromethane and washed with water. The organic layer was dried over anhydrous magnesium sulfate and was distilled to remove the solvent. The residue was purified by silica-gel column chromatography (a developer : hexane/ethyl acetate=20/1) to obtain the titled compound (0.15 g). Phase transition temperatures (° C.) were observed under a polarization microscope using a hot stage as follows:

$$Cry \xleftarrow{-40} S_X \xleftarrow{-18} S^*(3) \xleftarrow{-10} S_C^* \xleftarrow{-9.9} Iso$$

where
S*(3) : ternary tristable state
$S_X$ : higher state having field response
FIG. 25 is an IR spectrum of the titled compound.

Example 13

Synthesis of 1,1,1-trifluoro-2-octyl 4-benzyloxybenzoate

To a solution of 4-benzyloxybenzoic acid chloride (4.3 g) in methylene chloride (50 ml) was slowly added under ice cooling a solution of optically active 1,1,1-trifluoro-2-octanol (2.9 g), dimethylaminopyridine (0.6 g) and triethylamine (1.7 g) in methylene chloride (50 ml). The mixture was left to stand until it reached room temperature and allowed to react overnight. The mixture was poured in ice water and extracted with methylene chloride. The extracted layer was washed with dilute aqueous hydrochloric acid solution, water, 1N aqueous sodium carbonate solution and water, in this order, and dried over anhydrous magesium sulfate. After the solution was distilled to remove the solvent, the crude product obtained was purified by silica-gel column chromatography and recrystallized from ethanol to obtain the titled compound (3.8 g).

(2) Synthesis of 1,1,1-trifluoro-2-octyl 4-hydroxybenzoate

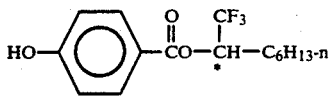

To a solution of the compound obtained in (1) above in methanol (100 ml) was added 10% Pd carried on carbon (0.4 g). The mixture was hydrogenated under a hydrogen atmosphere to obtain the titled compound (2.8 g).

(3) Synthesis of 4-(1,1,1-trifluoro-2-octyloxycarbonyl)phenyl 4-n-decanoyloxybenzoate

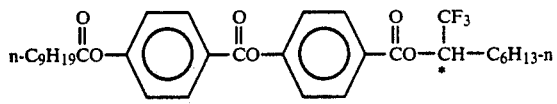

To a solution of the 4-n-decanoyloxybenzoic acid (0.43 g) obtained in Example 12, (3) and the 1,1,1-trifluoro-2-octyl 4-hydroxybenzoate (0.4 g) obtained in (2) above in tetrahydrofuran (about 30 ml) were added dicyclohexylcarbodiimide (0.32 g) and dimethylamonopyridine (0.01 g). The mixture was stirred at room temperature for about 20 hours and was distilled to remove the solvent. The residue was dissolved in dichloromethane and washed with water. The organic layer was dried over anhydrous magnesium sulfate and was distilled to remove the solvent. The residue was purified by silica-gel column chromatography (developer : hexane/ ethyl acetate=20/1) to obtain the titled compound (0.20 g).

Figure 26:
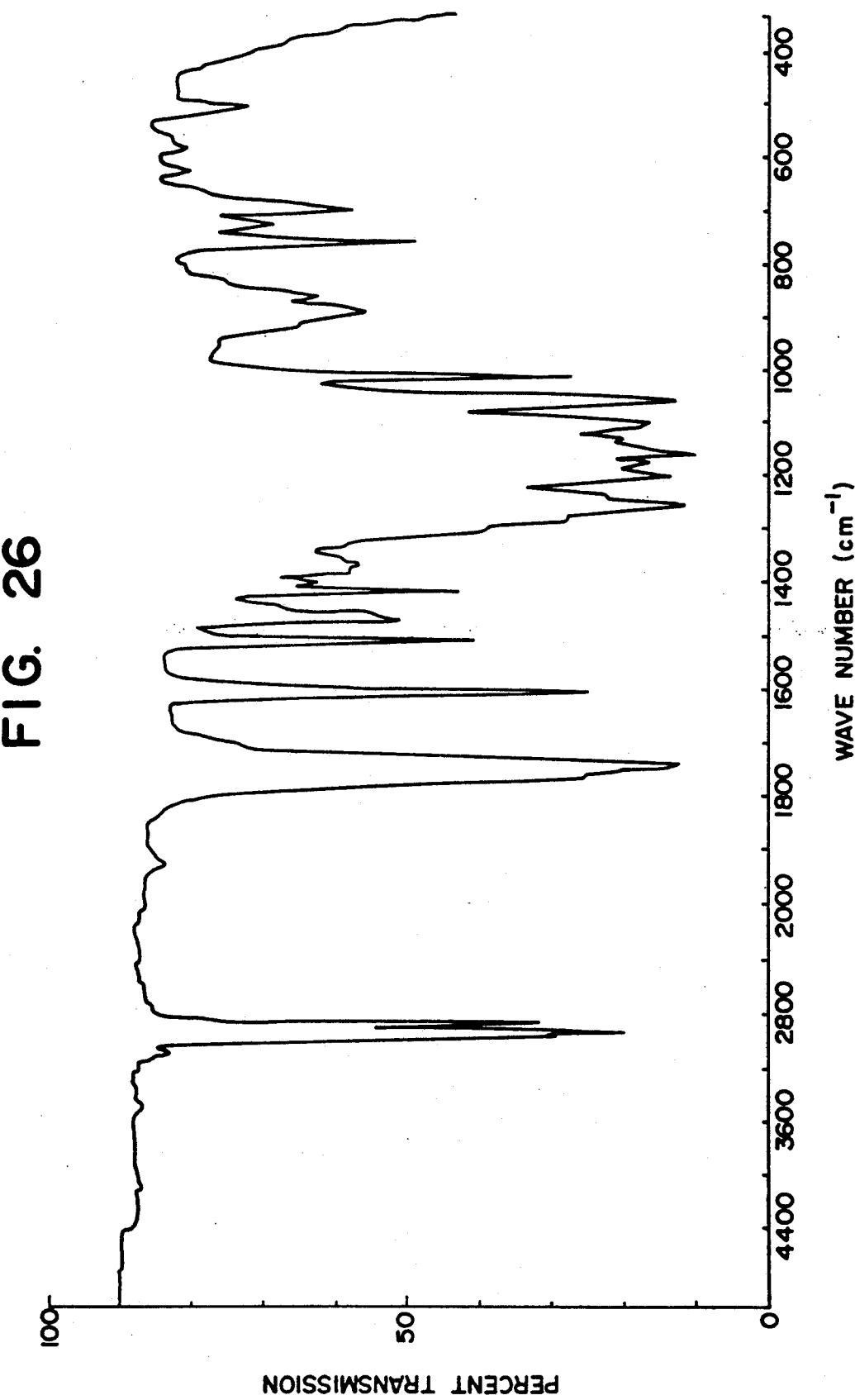

Phase transition temperatures (° C.) of the product observed under a polarization microscope using a hot stage were as follows:

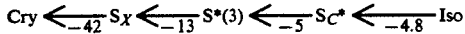

where
S*(3) : ternary tristable state
S$_X$ : higher state having field response.
FIG. 26 is an IR spectrum of the titled compound.

Example 14

Synthesis of 4-n-undecanoyloxybenzoic acid

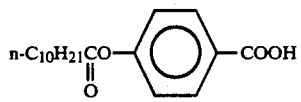

To a solution of p-hydroxybenzoic acid (3 g) and triethylamine (2.4 g) in dichloromethane (30 ml) were added undecanoyl chloride (4.5 g) and dimethylaminopyridine (0.2 g). The mixture was stirred at room temperature for about 20 hours. After dilute aqueous hydrochloric acid solution was added, an organic layer was separated by a funnel. After the solution was distilled to remove the solvent, the residue was washed with n-hexane and dried to obtain the titled compound (about 5 g).

(2) Synthesis of 4-(1,1,1-trifluoro-2-decyloxycarbonyl)phenyl 4-n-undecanoyloxybenzoate

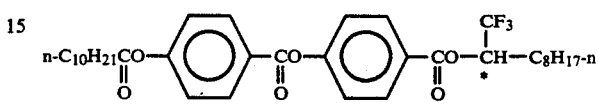

To a solution of the 4-undecanoyloxybenzoic acid )0.3 g) obtained in (1) above and the 1,1,1-trifluoro-2-decyl-4-hydroxybenzoate (0.3 g) obtained in Example 12, (2) in tetrahydrofuran (about 30 ml) were added dicyclohexylcarbodiimide (0.25 g) and dimethylaminopyridine (0.01 g). The mixture was stirred at room temperature for about 20 hours. The solution was distilled to remove the solvent and the residue was dissolved in dichloromethane and washed with water. The organic layer was dried over anhydrous magnesium sulfate and was distilled to remove the solvent. The residue was purified by silica-gel column chromatography (developer : hexane/ethyl acetate=20/1) to obtain the titled compound (0.21 g).

Figure 27:
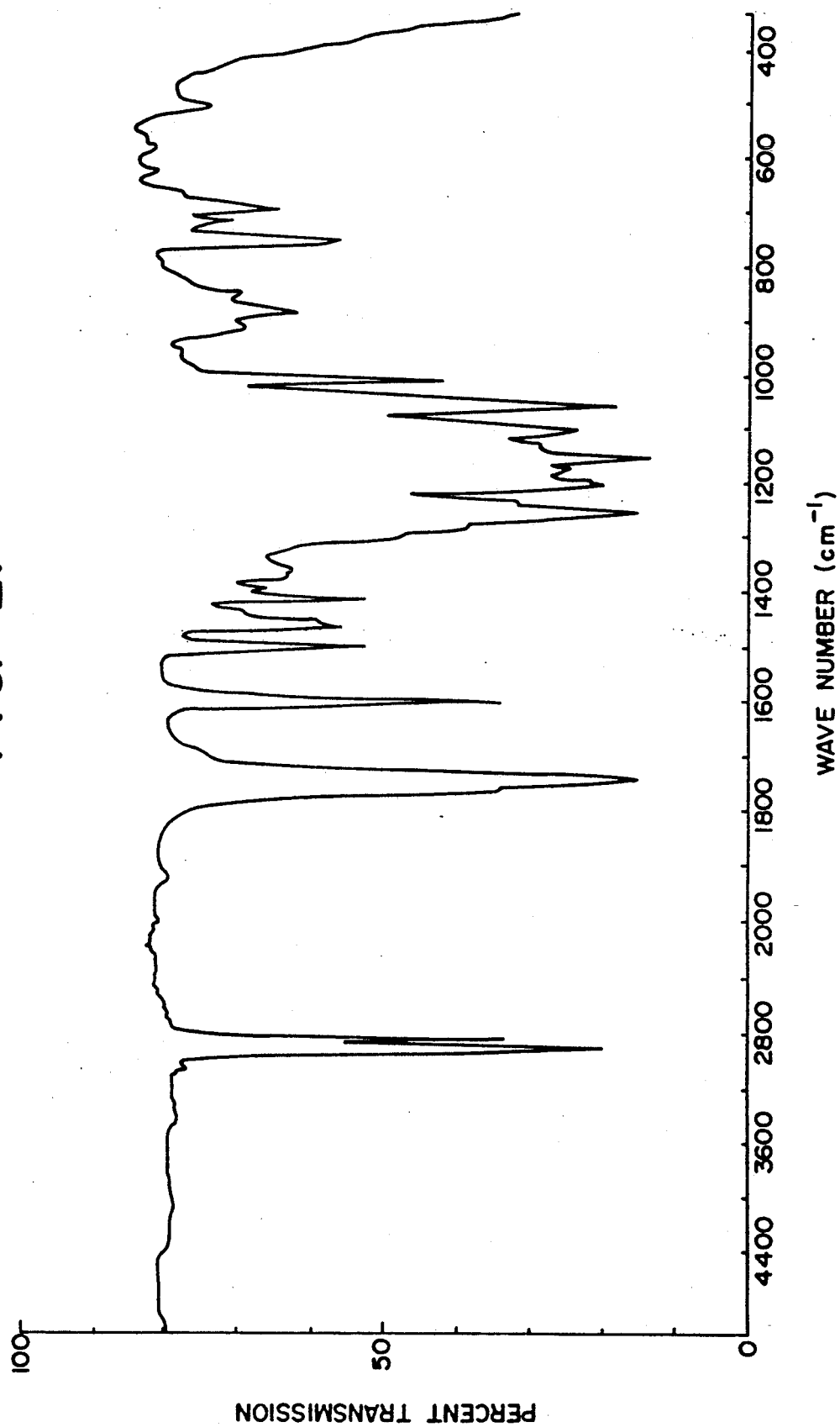

Phase transition temperatures (° C) observed under a polarization microscope using a hot stage were as follows:

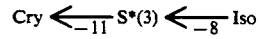

where
S*(3) : ternary tristable state.
FIG. 27 is an IR spectrum of the titled compound.

Example 15

Synthesis of 3-fluoro-4-(1,1,1-trifluoro-2-octyloxycarbonyl)phenyl 4-octyloxybiphenyl-4'-carboxylate (1) 1,1,1-Trifluoro-2-octyl 2-fluoro-4-hydroxybenzoate To a solution of 2-fluoro-4-benzyloxybenzoic acid chloride (1.4 g) in methylene chloride (10 ml) was slowly added under ice cooling a solution of optically active 1,1,1-trifluoro-2-octanol (1.2 g), triethylamine (0.6 g) and dimethylaminopyridine (0.7 g) in methylene chloride (10 ml). The mixture was left to stand until it reached room temperature and was stirred for 12 hours. The mixture was poured in ice water and extracted with methylene chloride. The extracted layer was washed with dilute aqueous hydrochloric acid solution, water, 1N aqueous sodium carbonate solution and water, in the order, and dried over anhydrous magnesium sulfate. The solution was distilled to remove the solvent until a crude product was obtained. The product was further purified by silica-gel column chromatography to obtain 1,1,1-trifluoro-2-octyl-2-fluoro 4-benzyloxybenzoate (2 g). The benzoate above and 10% Pd carried on carbon (0.2 g) were added to ethanol and the mixture was subjected to de-benzylation under a hydrogen atmosphere to obtain 1,1,1-trifluoro-2-octyl 3-fluoro-4-hydroxybenzoate

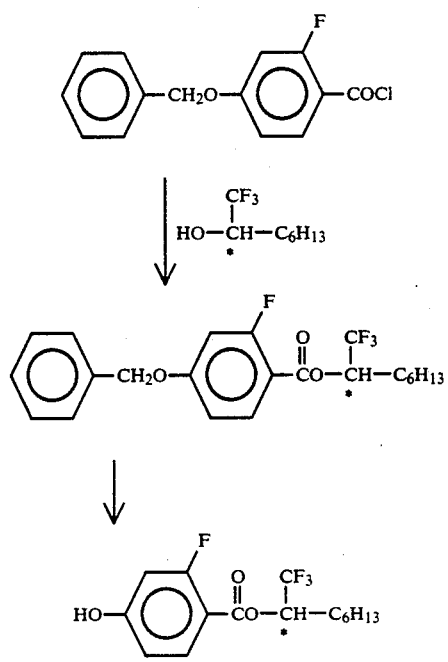

(2)
3-Fluoro-4-(1,1,1-trifluoro-2-octyloxycarbonyl)phenyl 4-octyloxybiphenyl-4'-carboxylate To a solution of the benzoate (1.6 g) obtained in (1) above, triethylamine (0.5 g) and dimethylaminopyridine (0.5 g) in methylene chloride (10 ml) was slowly added under cooling a solution of 4-n-octyloxybiphenyl-4'-carboxylic acid chloride (1.7 g) in methylene chloride (10 ml). The mixture was left to stand until it reached room temperature and stirred overnight. The mixture was poured in water and extracted with methylene chloride. The extracted layer was washed with dilute aqueous hydrochloric acid solution, water, 1N aqueous sodium carbonate solution and water, in this order, and dehydrated over anhydrous magnesium sulfate. After the solution was distilled under reduced pressure to remove the solvent, the residue was purified by silica-gel column chromatography and recrystallized from anhydrous ethanol to obtain the titled compound (0.8 g, $[\alpha]_D^{20} = +25.6°$).

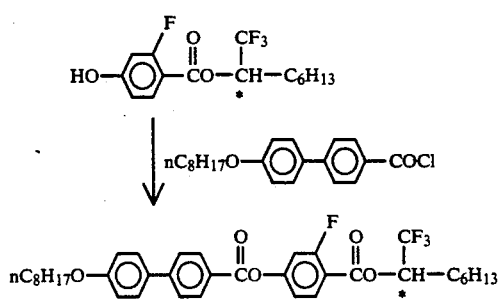

The compound showed mesomorphism and had phase transition temperatures (° C) which were observed under a polarization microscope using a hot stage as follows

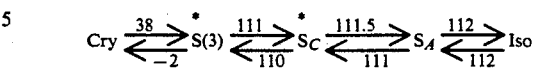

where

S*(3) : tristable state.

Figure 28:
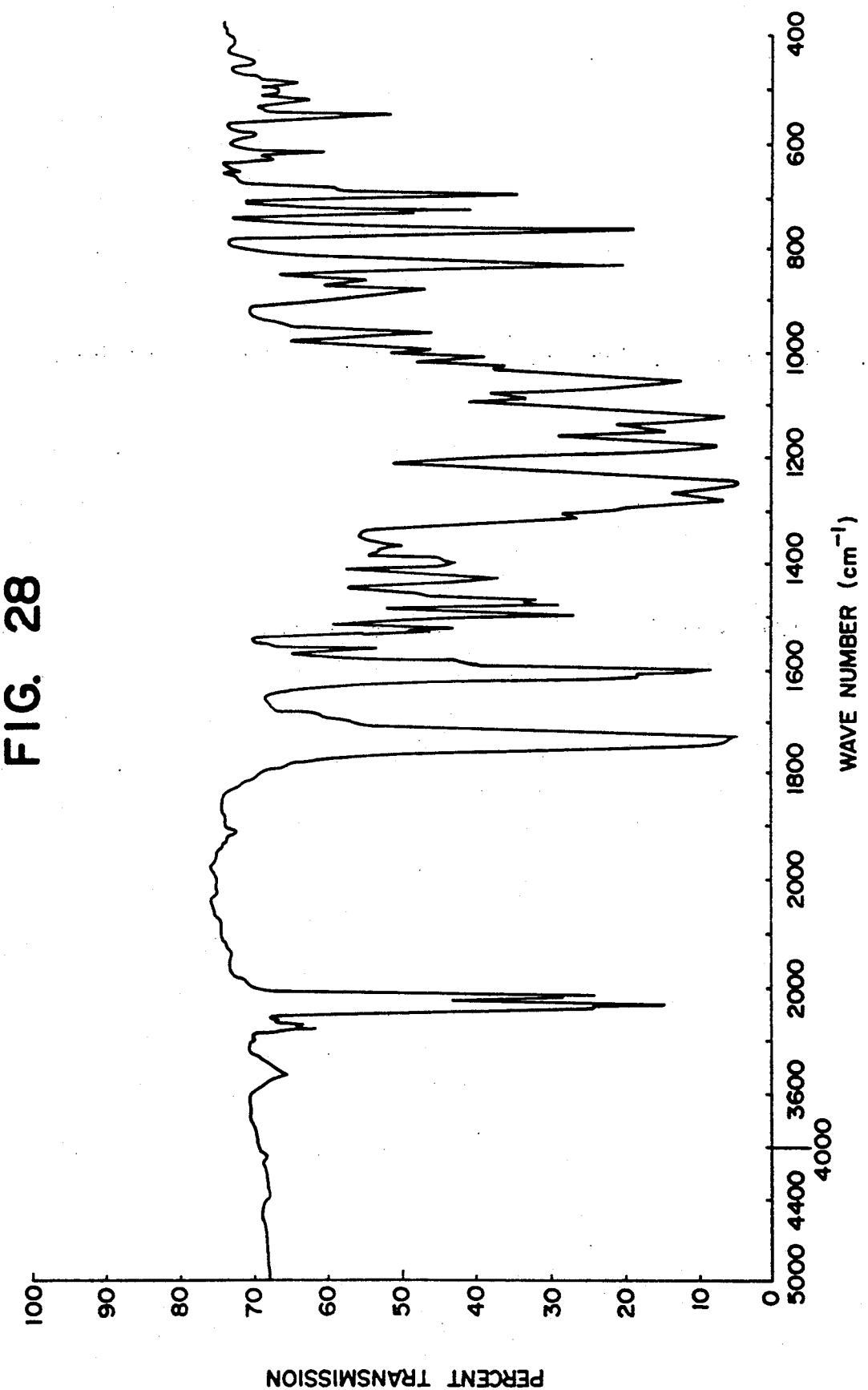

FIG. 28 is an IR spectrum (KBr) of the titled compound.

Example 16

Synthesis of
3-fluoro-4-(1,1,1-trifluoro-2-decyloxycarbonyl)phenyl 4-octyloxybiphenyl-4'-carboxylate

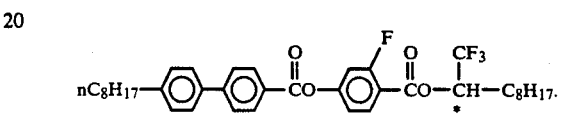

Example 15 was repeated except that 1,1,1-trifluoro-2-decanol was used in place of the 1,1,1-trifluoro-2-octanol to produce the titled compound ($[\alpha]_D^{20} = +29.0°$). The compound showed mesomorphism and had phase transition temperatures (° C.) which were observed a polarization microscope using a hot stage as follows:

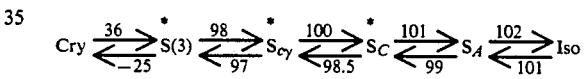

where S*(3) and S*$c_\gamma$ : tristable state and tetrastable state, respectively.

Figure 29:
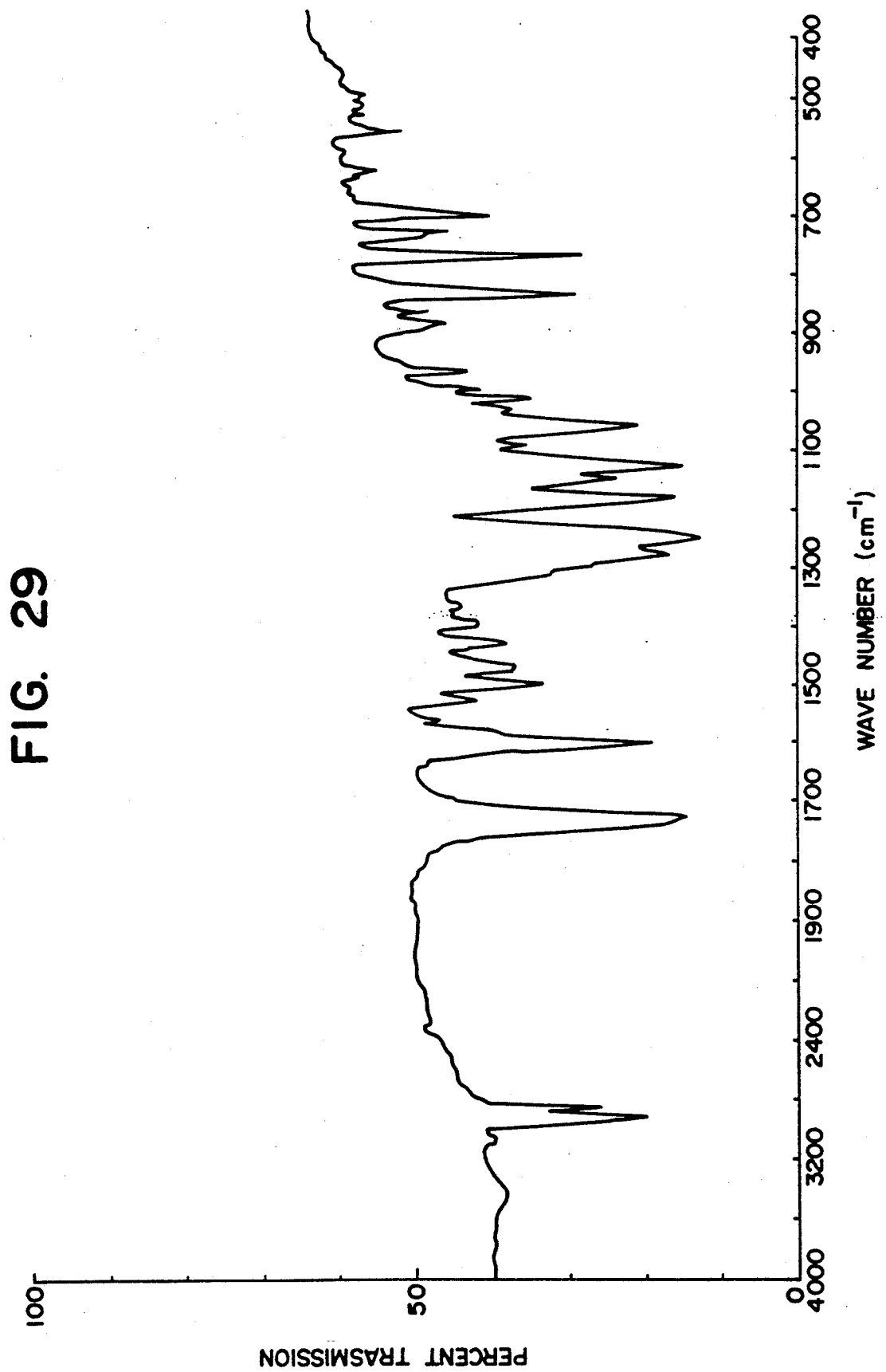

FIG. 29 is an IR spectrum (KBr) of the titled compound.

Example 17

Synthesis of
3-fluoro-4-(1,1,1-trifluoro-2-octyloxycarbonyl)phenyl 4-decylbiphenyl-4'-carboxylate

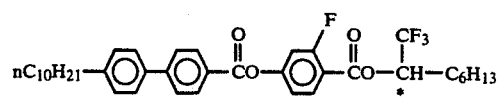

Example 15 was repeated except that 4-decylbiphenyl-4'-carboxylic acid was used in place of the 4-octyloxybiphenyl-4'-carboxylic acid to produce the titled compound ($[\alpha]_D^{20} = +28.7°$).

Phase transition temperatures (° C.)

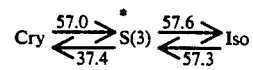

Figure 30:
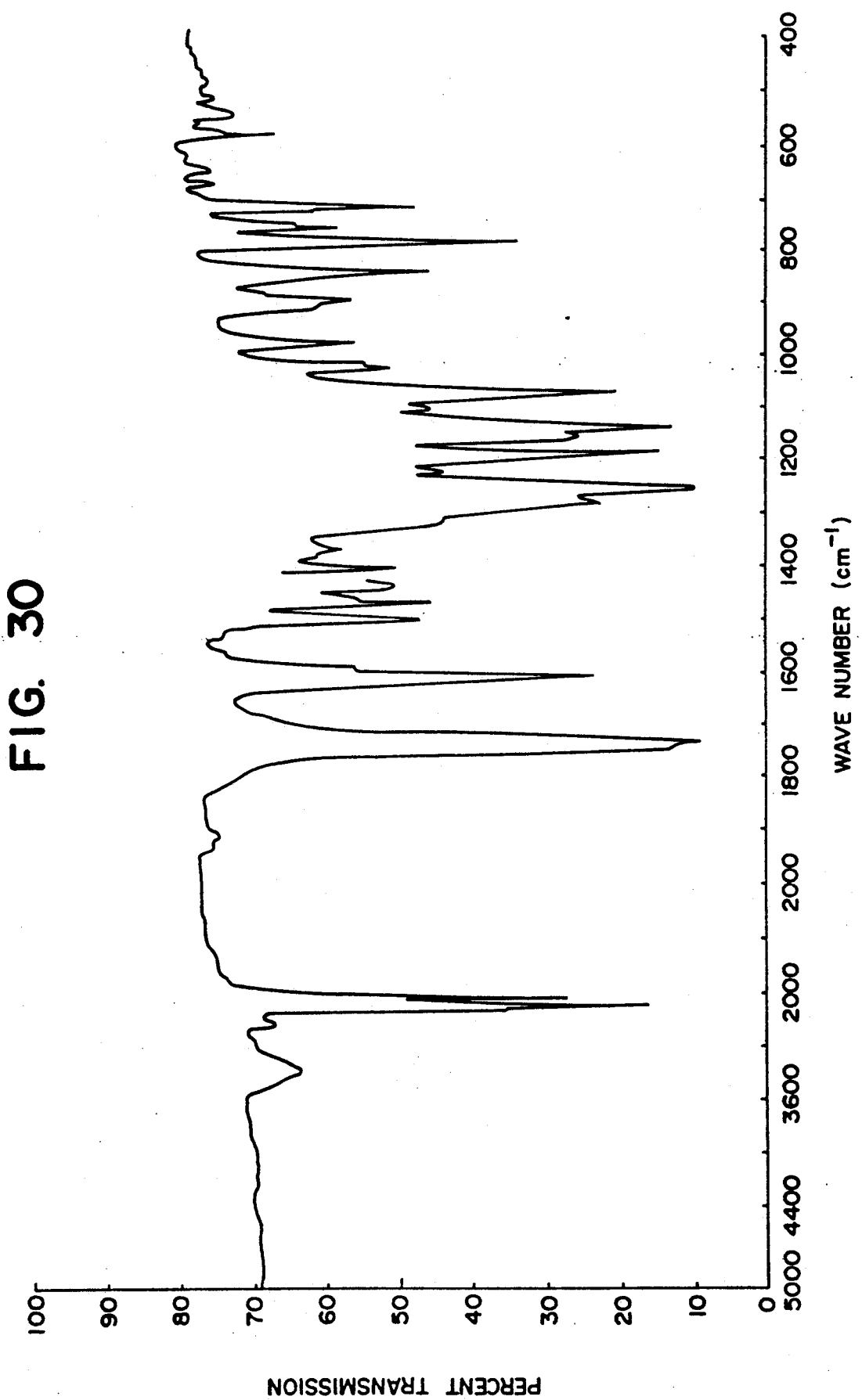

FIG. 30 is an IR spectrum (KBr) of the titled compound.

Example 18

Synthesis of 3-fluoro-4-(1,1,1-trifluoro-2-octyloxycarbonyl)phenyl 3-fluoro-4-decyloxybiphenyl-4'-carboxylate

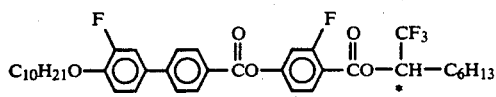

Example 15 was repeated except that 3-fluoro-4-decylbiphenyl-4'-carboxylic acid was used in place of the 4-octyloxybiphenyl-4'-carboxylic acid and that 4-n-octyl-biphenl-4'-carboxylic acid chloride was used in place of 4-n-octyloxybiphenyl-4'-carboxylic acid chloride, to obtain the titled compound ($[\alpha]_D^{20} = +27.6°$).

The compound showed mesomorphism and had phase transition temperatures (° C.) which were observed under a polarization microscope using a hot stage as follows:

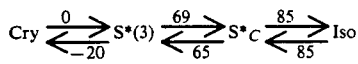

Figure 31:
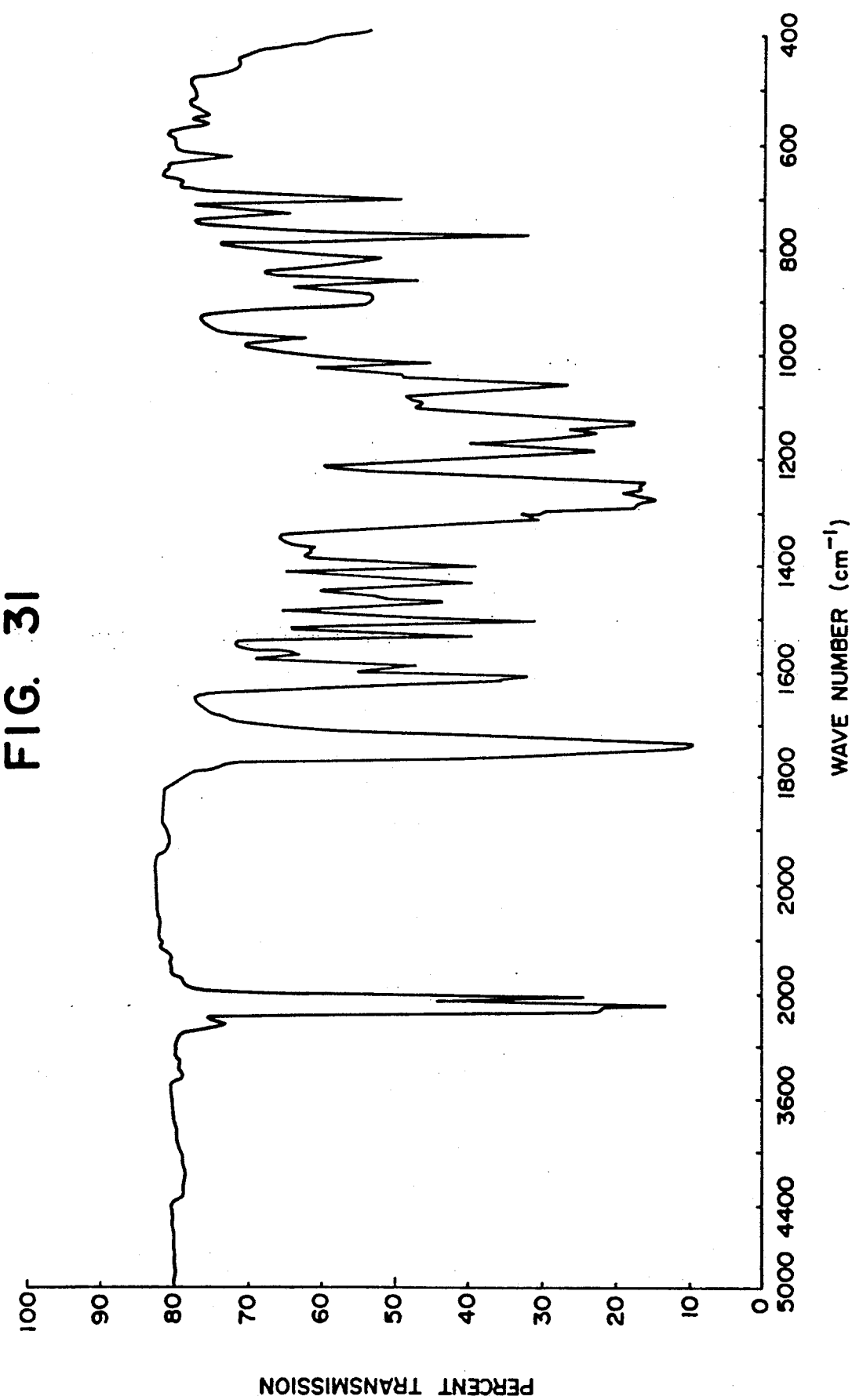

FIG. 31 is an IR spectrum (KBr) of the titled compound.

Example 19

Synthesis of 1,1,1-trifluorooctyl-4-(3-fluoro-4-decyloxybiphenyl-4'-methyleneoxy)-benzoate

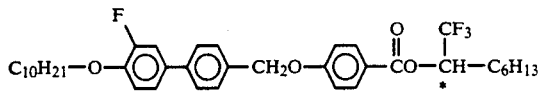

To a solution of sodium hydride (0.05 g) in anhydrous tetrahydrofuran (10 ml) were slowly added under ice cooling a solution of 1,1,1-trifluoro-2-octyl 4-hydroxybenzoate (0.5 g) prepared by the same procedure as in Example 15, (1) in anhydrous tetrahydrofuran (5 ml) and then slowly added a solution of 3-fluoro-4-decyloxy-4'-bromomethylbiphenyl (0.73 g) in dimethylsulfoxide (10 ml) in order to allow a reaction to proceed for 12 hours. The product was made acidic with 1N aqueous hydrochloric acid solution and extracted with methylene chloride. The extracted layer was washed with 1N aqueous sodium carbonate solution, water, aqueous sodium chloride solution (saturated) and water, in this order, until it was neutralized. The product was dried over anhydrous magnesium sulfate and subjected to distillation under reduced pressure in order to remove the solvent. Solid product obtained was purified by silica-gel column chromatography until the titled compound (0.62 g) was obtained.

The product showed mesomorphism and had phase transition temperatures (° C.) which were observed under a polarization microscope using a hot stage as follows:

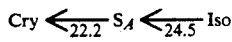

Example 20

Synthesis of 1,1,1trifluoro-2-octyl 4-(2-fluoro-4-decyloxyphenyloxycarbonyl)biphenyl-4'-carboxylate

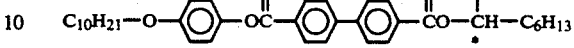

Into methylene chloride (20 ml) were added 4,4'-biphenyldicarboxylic acid chloride (0.5 g), (R)-(+)-1,1,1-trifluoro-2-octanol (0.15 g), triethylamine (0.09 g) and dimethylaminopyridine (0.03 g) and the mixture was left to stand for 8 hours in order to allow a reaction to proceed. Thereto were added 2-fluoro-4-decyloxyphenol (0.22 g) and triethylamine (0.09 g), and the mixture was left to stand for 8 hours in order to allow a reaction to proceed. The product was made acidic with 1N hydrochloric acid and extracted with methylene chloride. The extracted layer was washed with 1N aqueous sodium carbonate solution, water, aqueous sodium chloride solution (saturated) and water, in this order, until it was neutralized. After the product was dried over anhydrous magnesium sulfate, it was distilled under reduced pressure to remove the solvent. A solid product thus obtained was purified by silica-gel column chromatography until the titled compound (0.48 g) was obtained.

The product showed mesomorphism and had phase transition temperatures (° C.) which were observed under a polarization microscope using a hot stage as follows:

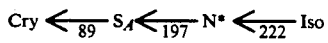

Example 21

Synthesis of 4-(1,1,1-trifluoro-2-octyloxycarbonyl)-2,3,5,6-tetrafluorophenyl 4-decyloxybiphenyl-4'-carboxylate

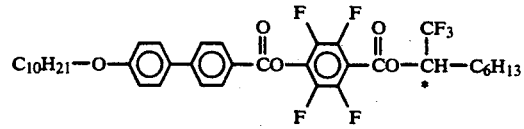

Example 15 was repeated except that 2,3,5,6-tetrafluoro-4-benzyloxybenzoic acid chloride was used in place of the 4-benzyloxybenzoic acid chloride to obtain the titled compound.

The compound showed mesomorphism and had phase transition temperatures (° C.) which were observed under a polarization microscope using a hot stage as follows:

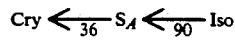

Example 22

Synthesis of 1,1,1-trifluoro-2-decyl 4-(4'-decylbiphenyl-4-oxycarbonyl)-2,3,5,6-tetrafluorobenzoate

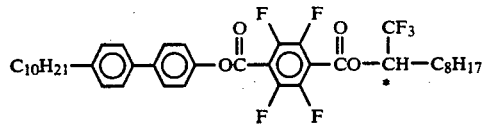

To methylene chloride (20 ml) were added 2,3,5,6-tetrafluoroterephthalic acid chloride (0.27 g), (R)-(+)-1,1,1-trifluoro-2-decanol (0.1 g), triethylamine (0.05 g) and dimethylaminopyridine (0.02 g). After the mixture was left to stand for 8 hours in order to allow a reaction to proceed, 4-decyl-4'-hydroxybiphenyl (0.15 g) and triethylamine (0.05 g) were added thereto. The mixture was left for about 8 hours in order to allow a reaction to proceed, made acidic with 1N aqueous hydrochloric acid solution and extracted with methylene chloride. The extracted layer was washed with 1N aqueous sodium carbonate solution, water, aqueous sodium chloride solution (saturated) and water, in this order, to make it neutral. The layer was dried over anhydrous magnesium sulfate and distilled under reduced pressure in order to remove the solvent. The solid product obtained was purified by silica-gel column chromatography to obtain the titled compound (0.14 g).

The product showed mesomorphism and had phase transition temperatures (° C.) which were observed under a polarization microscope using a hot stage as follows:

$$Cry \underset{13}{\rightleftarrows} S_A \underset{51}{\rightleftarrows} Iso$$

Example 23

Synthesis of 1,1,1-trifluoro-2-octyl 4-(4'-decyloxybiphenyl-4-oxycarbonyl)-2,3,5,6-tetrafluorobenzoate

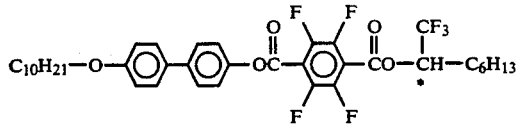

Example 22 was repeated except that 4-dodecyloxy-4'-hydroxybiphenyl and (R)-(+)-1,1,1-trifluorononanol were used in place of the 4-decyl-4'-hydroxybiphenyl and the (R)-(+)-1,1,1-trifluoro-2-decanol, respectively, to obtain the titled compound.

The compound showed mesomorphism and had phase transition temperatures (° C.) which were observed under a polarization microscope using a hot stage as follows:

$$Cry \underset{61}{\rightleftarrows} S_A \underset{86}{\rightleftarrows} Iso$$

Example 24

Synthesis of 1,1,1-trifluoro-2-octyl 4-(4'-decyloxycarbonylbiphenyl-4-oxycarbonyl)-2,3,5,6-tetrafluorobenzoate

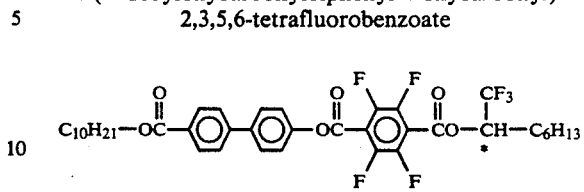

Example 22 was repeated except that 4-decyloxycarbonyl-4'-hydroxybiphenyl and (R)-(+)-1,1,1-trifluoro-2-octanol were used in place of the 4-decyl-4'-hydroxybiphenyl and the (R)-(+)-1,1,1-trifluoro-2-decanol, respectively, to obtain the titled compound.

The compound showed mesomorphism and had phase transition temperatures (° C.) which were observed under a polarization microscope using a hot stage as follows:

$$Cry \underset{20}{\rightleftarrows} S_A \underset{34}{\rightleftarrows} Iso$$

Example 25

(1) Synthesis of 1,1,1-trifluoro-2-octyl 6-hydroxynaphthalene-2-carboxylate

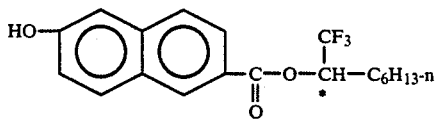

To a solution of 2-hydroxy-6-carboxynaphthalene (1 g) and optically active 1,1,1-trifluoro-2-octanol (1.1 g) in methylene chloride (50 ml) was added a few drops of conc. sulfuric acid and the mixture was refluxed under stirring for about two days.

The reaction mixture was poured in water to collect the organic layer. The layer was washed with aqueous sodium hydroxide solution and water, in this order, and dried over anhydrous magnesium sulfate. After the solution was distilled to remove the solvent, the residue was purified by silica-gel column chromatography (developer : chloroform) to obtain the titled compound (0.57 g).

(2) Synthesis of 2-n-decyloxy-6-carboxynaphthalene

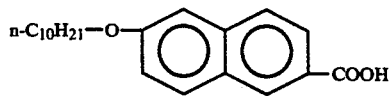

After a solution of decylmonobromide (7 g), 2-hydroxy-6-carboxynaphthalene (2 g) and anhydrous potassium carbonate (4 g) in dimethylformamide (100 ml) was stirred at 130° C. for two hours, it was poured in water. Dilute aqueous hydrochloric acid solution was added thereto until the solution was neutral. To the solution was added diethylether in order to effect extraction. The extracted layer was distilled to remove the solvent. The residue was added to a solution of sodium hydroxide (3.3 g) in water (10 ml) and ethanol (50 ml).

The mixture was refluxed for about one day. Thereto was added dilute aqueous hydrochloric acid solution until the solution was neutral. The solution was distilled to remove the solvent and concentrated. Solid precipitate was collected and recrystallized from water-ethanol mixture to obtain the titled compound (2.4 g).

(3) Synthesis of
6-(1,1,1-trifluoro-2-octyloxycarbonyl)naphthalene-(2)
6-n-decyloxynaphthalene-2-carboxylate

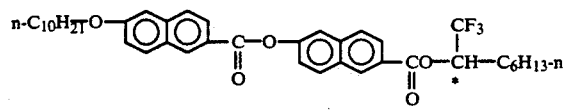

To a solution of the compound (0.55 g) obtained in (1) above and the compound (0.6 g) obtained in (2) above in tetrahydrofuran (40 ml) were added dicyclohexylcarbodiimide (0.45 g) and dimethylaminopyridine (0.05 g). After the mixture was stirred at room temperature overnight, it was distilled to remove the solvent. The residue was dissolved in dichloromethane (50 ml) and washed with dilute aqueous hydrochloric acid solution and water in this order. The organic layer was collected and dried over anhydrous magnesium sulfate. After the layer was distilled to remove the solvent, the residue was purified by silica-gel column chromatography (developer : hexane/ethyl acetate =20/1) to obtain the titled compound (0.42 g). Specific rotation $[\alpha]_D^{20} = +44°$.

The compound had phase transition temperatures (° C.) which were observed under a polarization microscope using a hot stage were as follows:

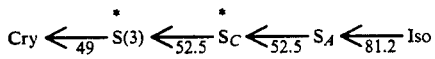

where S*(3) =tristable state.

Figure 32:
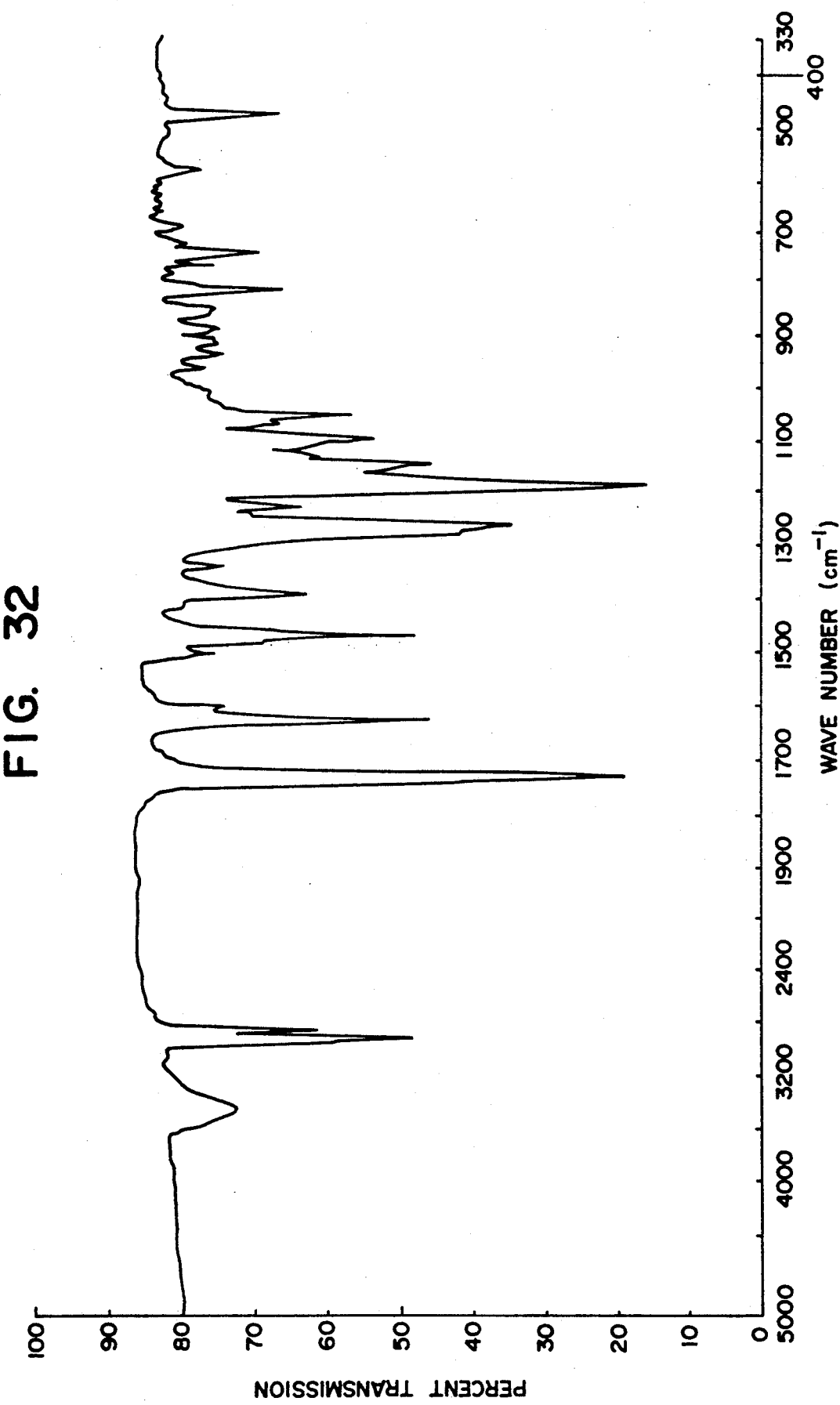

FIG. 32 is an IR spectrum (KBr) of the titled compound.

Example 26.

(1) Synthesis of
2-n-octylcarbonyloxy-6-carboxynaphthalene

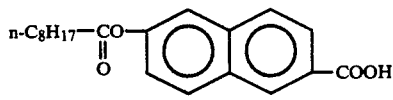

After a solution of 2-hydroxy-6-carboxynaphthalene (1 g), triethylamine (0.6 g) and nonylic acid chloride (2 g) and dimethylaminopyridine (0.05 g) in methylene chloride (50 ml) was stirred at room temperature for 24 hours, the solution was poured in water. Dilute aqueous hydrochloric acid solution was added thereto until the solution was neutral. The solution was extracted with dimethylether. After the extracted layer was dehydrated over anhydrous magnesium sulfate, it was distilled to remove the solvent. The residue was washed with enough hexane to obtain the titled compound (0.9 g).

(2) Synthesis of
6-(1,1,1-trifluoro-2-octyloxycarbonyl)naphthalene-(2)
6-n-octylcarbonyloxynaphthalene-2-carboxylate

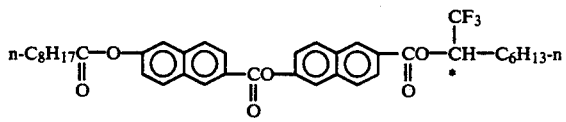

To a solution of the naphthalene compound (0.4 g) obtained in (1) and the 1,1,1-trifluoro-2-octyl-6-hydroxynaphthalene-2-carboxylate (0.55 g) obtained in Example 25, (1) in tetrahydrofuran (40 ml) were added dicyclohexylcarbodiimide (0.4 g) and dimethylaminopyridine (0.05 g). After the mixture was stirred overnight, it was distilled to remove the solvent. The residue was dissolved in dichloromethane (40 ml) and washed with dilute aqueous hydrochloric acid solution and water, in this order. After the solution was dehydrated over anhydrous magnesium sulfate, it was distilled to remove the solvent. The residue was purified by silica-gel column chromatography (developer : hexane/acetic acid = 20/1) to obtain the titled compound (0.05 g) having specific rotation, $[\alpha]_D^{20} = +45.5°$.

Figure 33:
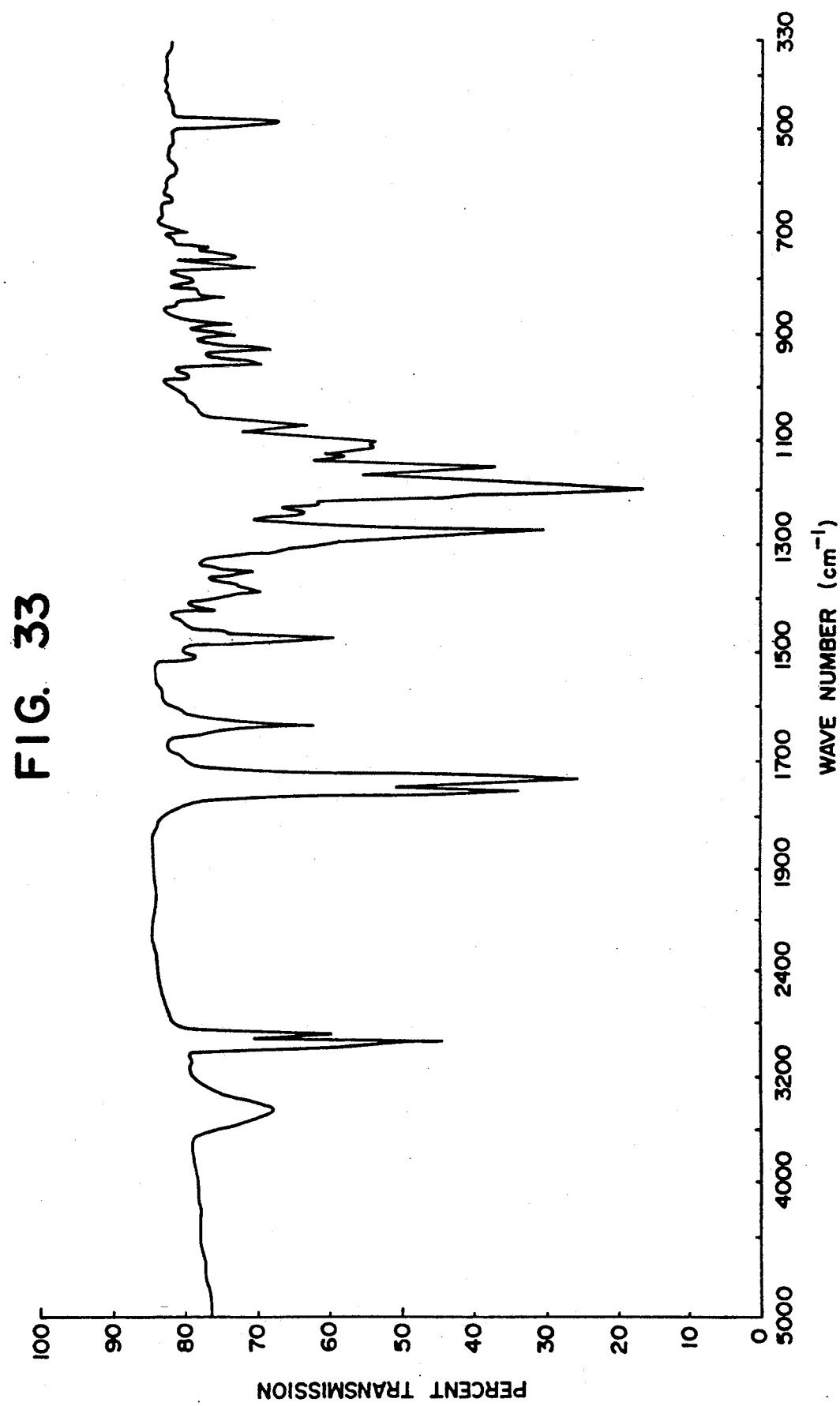

The product had phase transition temperature (° C.) which were observed under a polarization microscope using a hot stage as follows:

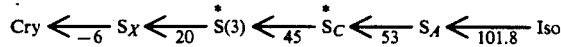

where
S*(3) : tristable state,
$S_X$ : higher but not identified liquid crystal phase.
FIG. 33 is an IR spectrum (KBr) of the compound.

Example 27

(1) Synthesis of
2-n-decyloxycarbonylnaphthalene-6-carboxylic acid chloride

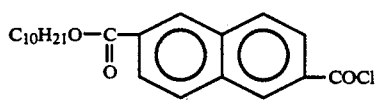

After a solution of n-decyl alcohol (0.5 g), naphthalene-2,6-dicarboxylic acid dichloride (0.6 g), and triethylamine (0.27 g) and a very small amount of dimethylaminopyridine in methylene chloride (50 ml) was stirred at room temperature overnight, the solution was distilled to remove the solvent, until the titled compound (about 0.5 g) was obtained.

(2) Synthesis of
6-(1,1,1-trifluoro-2-octyloxycarbonyl)naphthalene-(2)
6-n-decyloxycarbonylnaphthalene-2-carboxylate

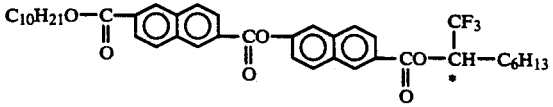

To a solution of the 1,1,1-trifluoro-2-octyl 6-hydroxynaphthalene-2-carboxylate (0.58 g) obtained in Example 25, (1) and triethylamine (0.3 g) in methylene chloride (40 ml) was added drop by drop a solution of the 2-n-decyloxycarbonylnaphthalene-6-carboxylic acid chloride (0.5 g) obtain in (1) above. Then, dimetylaminopyridine (0.02 g) was added to the solution and the solution was stirred at room temperature overnight. After dilute aqueous hydrochloric acid solution was added until the solution was neutral, extraction was made with methylene chloride. The extract was dried over anhydrous magnesium sulfate and distilled to remove the solvent. The residue was purified by silica-gel column chromatography (developer : hexane/acetic acid =20/1) to obtain the titled compound (0.15 g) having specific rotations, $[\alpha]_D^{20} = +41.5°$.

Phase transition temperatures (° C.) which were observed under a polarization microscope using a hot stage were

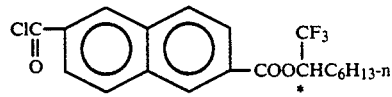

Figure 34:
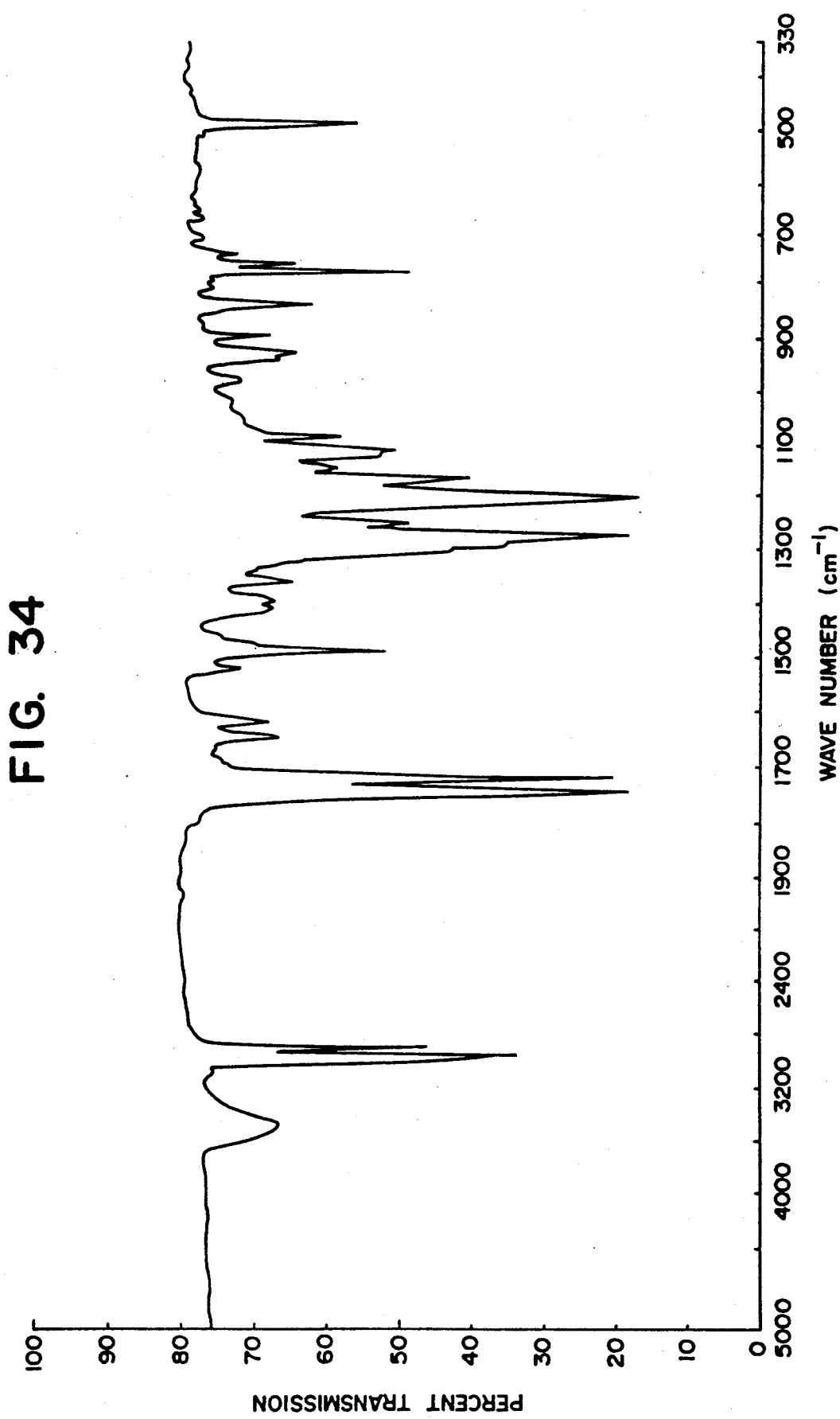

FIG. 34 is an IR spectrum (KBr) of the compound.

Example 28

(1) Synthesis of 6-(1,1,1-trifluoro-2-octyloxycarbonyl)naphthalene-2-carboxychloride

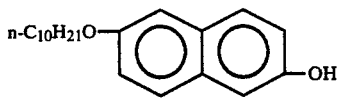

A solution of naphthalene 2,6-dicarboxylic acid dichloride (0.6 g), optically active 1,1,1-trifluoro-2-octyl alcohol (0.44 g), triethylamine (0.27 g) and a very small amount of dimethylaminopyridine in methylene chloride (50 ml) was stirred at room temperature overnight. After the solution was distilled to remove the solvent, the titled compound (about 0.8 g) was obtained.

(2) Synthesis of 2-n-decyloxy-6-hydroxynaphthalene

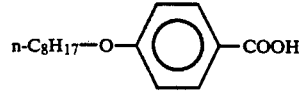

A solution of decylmonobromide (1.5 g), 2,6-dihydroxynaphthalene (1 g) and anhydrous potassium carbonate (0.8 g) in dimethylformamide (50 ml) was stirred at 130° C. for four hours. The solution was poured in water and was made neutral with dilute aqueous hydrochloric acid solution. To the solution was added diethyl ether in order to effect extraction and the extract was distilled to remove the solvent. The residue was washed with hexane and recrystallized from water/ethanol (1/9) to obtain the titled compound (about 1 g).

(3) Synthesis of 6-n-decyloxynaphthalene-(2) 6-(1,1,1-trifluoro-2-octyloxycarbonyl)naphthalene-2-carboxylate

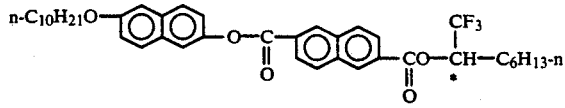

To a solution of the hydroxynaphthalene (0.64 g) obtained in (2) above and triethylamine (0.3 g) in methylene chloride (40 ml) was added drop by drop the 6-(1,1,1-trifluoro-2-octyloxycarbonyl)naphthalene-2-carboxychloride (0.8 g) obtained in (1) above. To the solution was added dimethylaminopyridine (0.02 g) and the mixture was stirred at room temperature overnight. The solution was neutralized with dilute aqueous hydrochloric acid solution and extracted with methylene chloride. The extract was dried over anhydrous magnesium sulfate and distilled to remove the solvent. The residue was purified by silica-gel column chromatography (developer : hexane/ethyl actate =20/1) to obtain the titled compound (0.4 g) having specific rotation, $[\alpha]_D^{20} = +45.5°$.

Phase transition temperatures (° C.) observed under a polarization microscope using a hot stage were

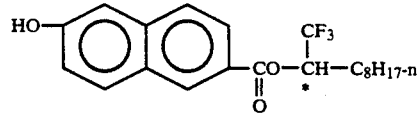

Figure 35:
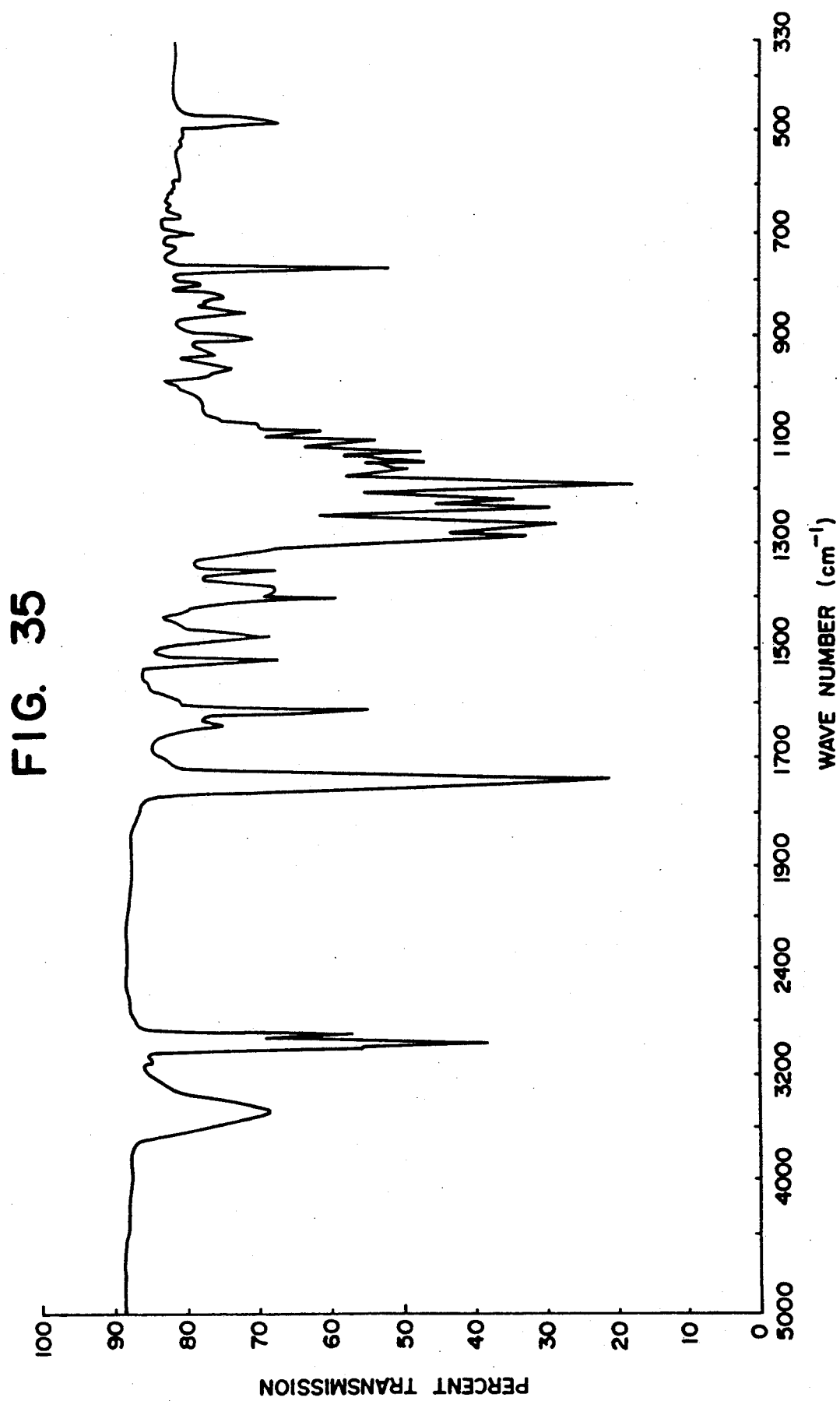

FIG. 35 is an IR spectrum (KBr) of the compound.

Example 29

(1) Synthesis of 1,1,1-trifluoro-2-decyl 6-hydroxynaphthalene-2-carboxylate

To a solution of 2-hydroxy-6-carboxylnaphthalene (1 g) and optically active 1,1,1-trifluoro-2-decyl alcohol (1.1 g) in methylene chloride (50 ml) was added a few drops of conc. sulfuric acid and the mixture was refluxed under stirring for about two days. The product was poured in water and the organic layer was collected. The organic layer was washed with aqueous sodium hydroxide solution and water, in this order. After the solution was dried over anhydrous magnesium sulfate, and distilled to remove the solvent. The residue was purified by silica-gel column chromatography (developer : chloroform) to obtain the titled compound (0.58 g).

(2) Synthesis of 4-n-octyloxybenzoic acid

A solution of octylbromide (4.19 g), 4-hydroxybenzoic acid (3 g) and potassium carbonate (3 g) in dimethylformamide (100 ml) was stirred at 130° C. for two hours. The solution was poured in water and neutralized with dilute aqueous hydrochloric acid solution. Diethylether was added to effect extraction. After the extracted layer was distilled to remove the solvent, the residue was added to a solution of sodium hydroxide (3.3 g), water (10 ml) and ethanol (50 ml). The solution obtained was refluxed for about a day and neutralized with dilute aqueous hydrochloric acid solution. The solution was distilled to remove the solvent and concentrated. The solid obtained was collected and recrystallized from water/ethanol to obtain the titled compound (3.88 g).

(3) Synthesis of 1,1,1-trifluorodecyl 6-(4-n-octyloxyphenylcarbonyloxy)naphthalene-2-carboxylate

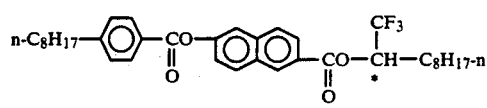

To a solution of the 1,1,1-trifluoro-2-decyl-6-hydroxynaphthalene-2-carboxylate (0.5 g) obtained in (1) above, the 4-n-octyloxybenzoic acid (0.4 g) obtained in (2) above in tetrahydrofuran (40 ml) were added dicyclohexylcarbodiimide (0.45 g) and dimethylaminopyridine (0.05 g). The solution was stirred at room temperature overnight. The solution was distilled to remove the solvent. The residue was dissolved in dichloromethane (50 ml) and the solution was washed with dilute aqueous hydrochloric acid solution and water in this order. The organic layer collected was dried over anhydrous magnesium sulfate, and distilled to remove the solvent. The residue was purified by silica-gel column chromatography (developer : hexane/ethyl acetate =20/1) to obtain the titled compound (0.39 g) having specific rotation, $[\alpha]_D^{20} = +45.79°$.

Phease transition temperatures (° C.) which were observed under a polarization microscope using a hot stage were as follows:

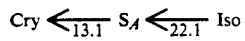

Figure 36:
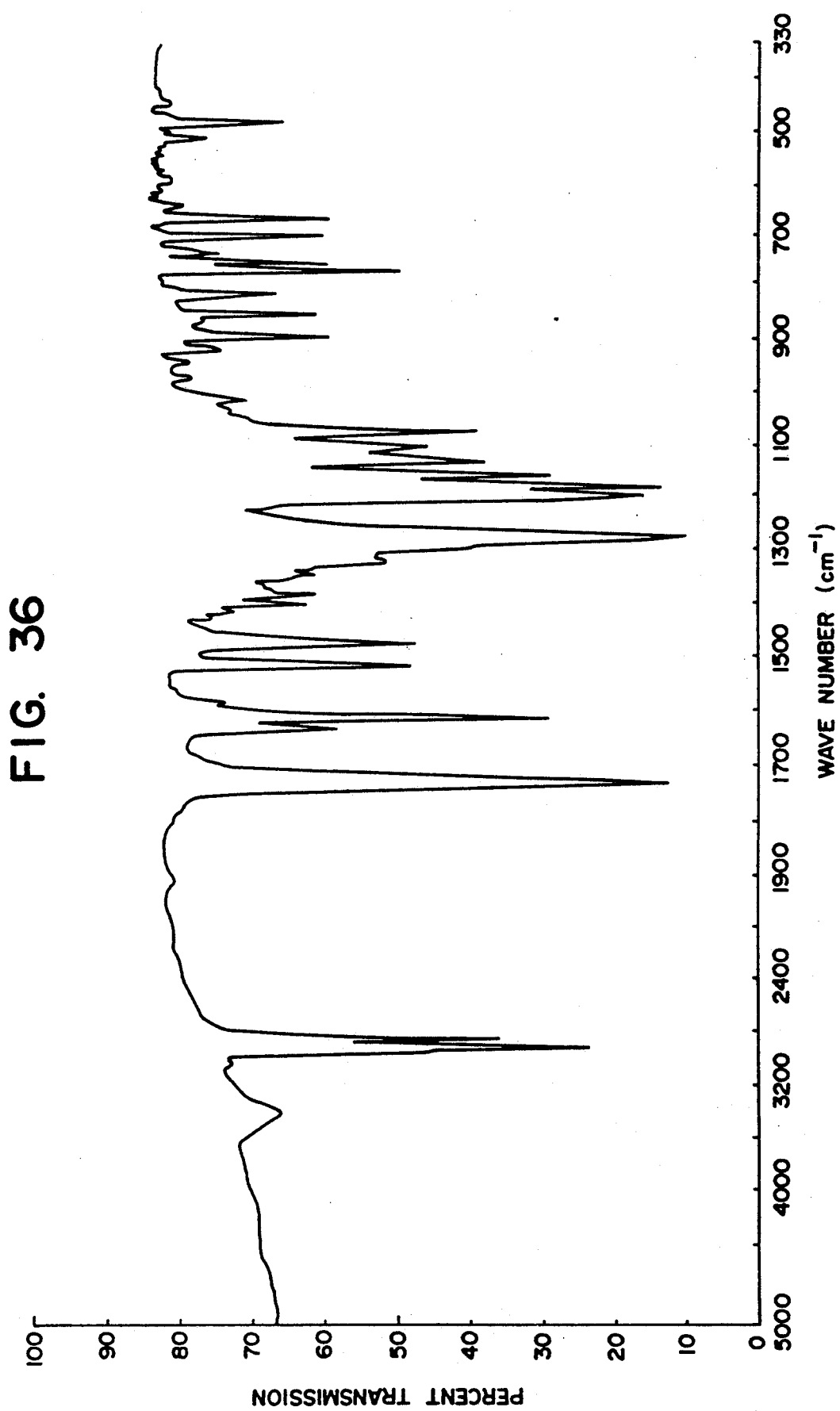

FIG. 36 is an IR spectrum (KBr) of the titled compound.

1 Example 30

(1) Synthesis of 4 n dodecyloxybenzoic acid

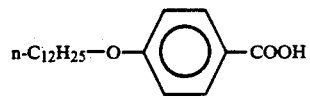

A solution of dodecylbromide (8.2 g, 4-hydroxybenzoic acid (5 g) and potassium carbonate (5 g) in dimethylformamide (100 ml) was stirred at 130° C. for two hours. The solution was poured in water and neutralized with dilute aqueous hydrochloric acid solution. Diethyl ether was added in order to effect extraction and the extracted layer was distilled to remove the solvent. The residue was added to a solution of sodium hydroxide (3 g). water (10 ml) and ethanol(50 ml) and the solution was refluxed for about one day. The solution was neutralized with dilute aqueous hydrochloric acid solution and distilled to remove the solvent and concentrated. Solid collected was recrystallized from water/ethanol to obtain the titled compound (4.9 g).

(2) Synthesis of 1,1,1-trifluoro-2-decyl 6-(4-n-dodecyloxyphenylcarbonyloxy) naphthalene-2-carboxylate

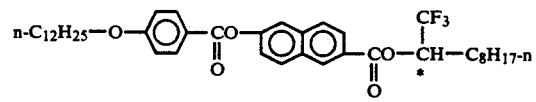

To a solution of the 4-n-dodecyloxybenzoic acid (0.52 g) obtained in (1) above and the 1,1,1-trifluoro-2-decyl 6-hydroxynaphthalene-2-carboxylate (0.47 g) obtained in Example 29, (1) in tetrahydrofuran (40 ml) were added dicyclohexylcarbodiimide (0.45 g) and dimethylaminopyridine (0.05 g). The solution was stirred at room temperature overnight and distilled to remove the solvent. The residue was dissolved in dichloromethane (50 ml) and washed with dilute aqueous hydrochloric acid solution and water, in this order. The organic layer collected was dried over anhydrone magnesium sulfate and distilled to remove the solvent. The residue was purified by silica-gel column chromatography (developer : hexane/ethyl acetate =20/1) to obtain the titled compound (0.42 g) having specific rotation, $[\alpha]_D^{20} = +43.46°$.

Phase transition temperatures (° C.) which were observed under a polarization microscope using a hot stage were

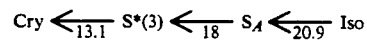

where
S*(3) =tristable state.

Figure 37:
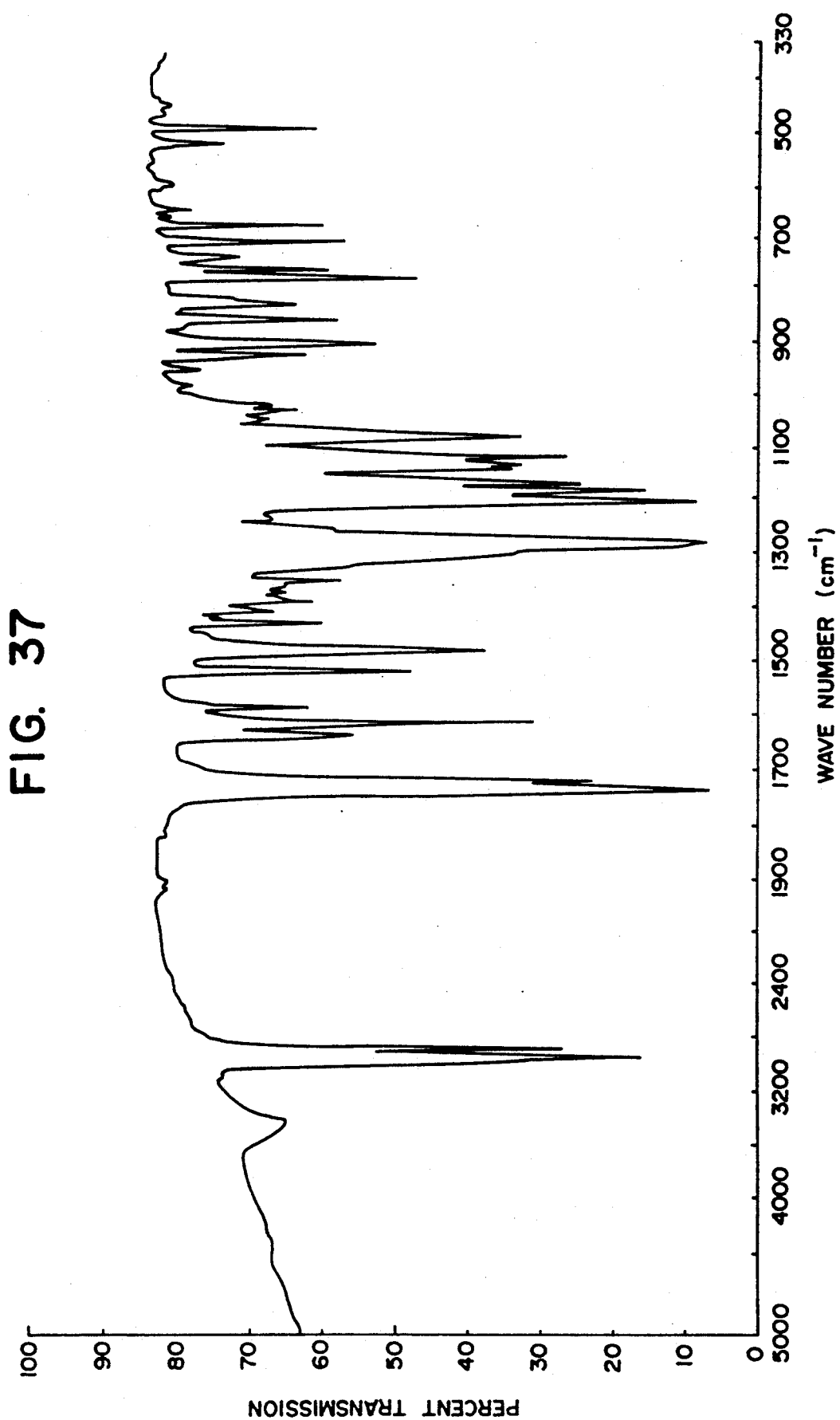

FIG. 37 is an IR spectrum (KBr) of the titled compound.

Example 31

(1) Synthesis of 1,1,1-trifluoro-2-octyl 6-hydroxynaphthalene-2-carboxylate

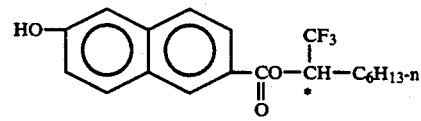

To a solution of 2-hydroxy-6-carboxynaphthalene (2 g) and optically active 1,1,1-trifluoro-2-octyl alcohol (2.2 g) in ethylene chloride (50 ml) was added a few drops of conc. sulfuric acid, and the solution was refluxed under stirring for about two days. The solution obtained was poured in water in order to collect the organic layer. The layer was washed with aqueous sodium hydroxide solution and water, in this order, and dried over anhydrous magnesium sulfate. The solution was distilled to remove the solvent. The residue was purified by silica-gel column chromatography (developer : chloroform) to obtain the titled compound (1.2 g).

(2) Synthesis of 4-n-nonylcarbonyloxybenzoic acid

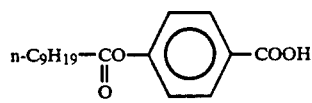

A solution of 4-hydroxybenzoic acid (3 g), decanoic acid chloride (4.3 g), triethylamine (2.4 g) and dimethylaminopyridine (0.2 g) in methylene chloride (50 ml) was stirred at room temperature for 24 hours, and then poured in water. The solution was neutralized with dilute aqueous hydrochloric acid solution and extracted with dimethyl ether. The extracted product was dried over anhydrous magnesium sulfate and distilled to remove the solvent. The residue was washed enough with hexane to obtain the titled compound (2.7 g).

(3) Synthesis of 1,1,1-trifluoro-2-octyl 6-(4-n-nonylcarbonyloxyphenylcarbonyloxy) naphthalene-2-carboxylate

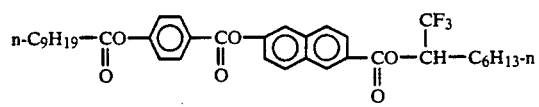

To a solution of the 1,1,1-trifluoro-2-octyl 6-hydroxynaphthalene-2-carboxylate (0.6 g) obtained in (1) above and the 4-n-nonylcarbonyloxybenzoic acid (0.45 g) obtained in (2) above in tetrahydrofuran (40 ml) were added dicyclohexylcarbodiimide (0.45 g) and dimethylaminopyridine (0.05 g). The solution was stirred overnight and distilled to remove the solvent. The residue was dissolved in dichloromethane (40 ml) and washed with dilute aqueous hydrochloric acid solution and water, in this order. The solution was dried over anhydrous magnesium sulfate and distilled to remove the solvent. The residue was purified by silica-gel column chromatography (developer : hexane/ethyl acetate =20/1) to obtain the titled compound (0.05 g) having specific rotation, $[\alpha]_D^{20}= +42.86°$.

Figure 38:
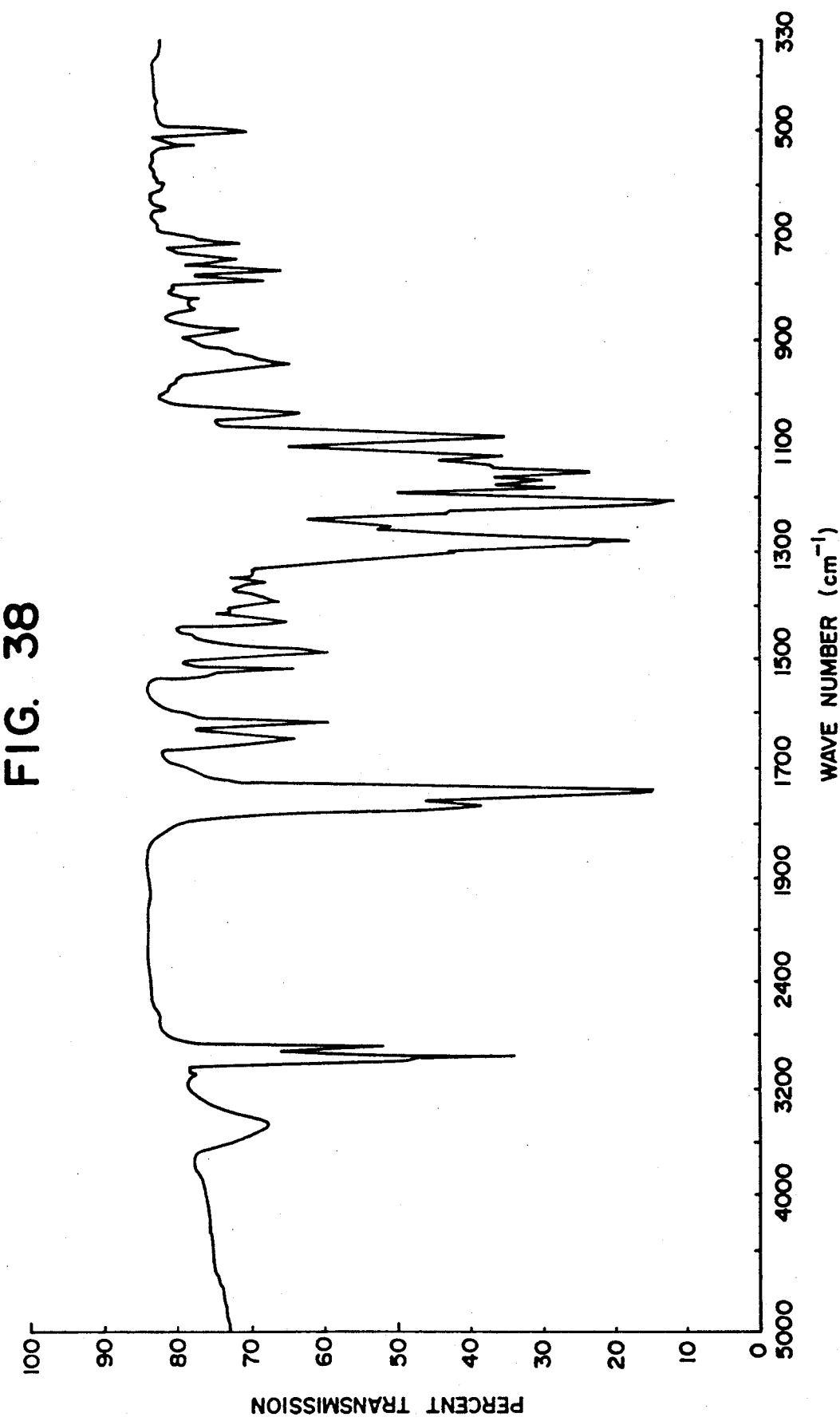

Phase transition temperatures (° C.) which were observed under a polarization microscope using a hot stage were $$Cry \underset{22.7}{\longleftrightarrow} S^*(3) \underset{32.8}{\longleftrightarrow} S_A \underset{42.1}{\longleftrightarrow} Iso$$

where
S*(3) : tristable state.
FIG. 38 is an IR spectrum (KBr) of the titled compound.

Example 32

(1) Synthesis of 1,1,1-trifluoro-2-decyl-4-benzyloxybenzoate

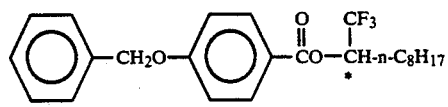

To a solution of 4-benzyloxybenzoic acid chloride (1.23 g) in methylene chloride (10 ml) was slowly added under ice cooling a solution of optically active 1,1,1-trifluoro-2-decanol (0.96 g), dimethylaminopyridine (0.55 g) and triethylamine (0.48 g) in methylene chloride (20 ml). The solution was left to stand until it reached room temperature and further left to stand overnight in order to allow a reaction to proceed. The product was poured in ice water and methylene chloride was added thereto to effect extraction. The extracted layer was washed with dilute aqueous hydrochloric acid solution, water, 1N aqueous sodium carbonate solution and water, in this order, and dried over anhydrone magnesium sulfate. The solution was distilled to remove the solvent until a crude product was obtained. The product was further purified by silica-gel column chromatography and recrystallized from ethanol to obtain the titled compound (1.84 g).

Synthesis of 1,1,1-trifluoro-2-decyl-4-hydroxybenzoate

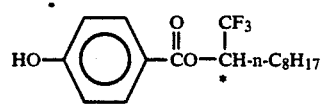

A solution of the compound obtained in (1) above in ethanol (15 ml) was hydrogenated in the presence of 10% Pd carried on carbon (0.36 g) under a hydrogen atmosphere to obtain the titled compound (1.43 g).

(3) Synthesis of 2-fluoro-4-n-decanoyloxybenzoic acid

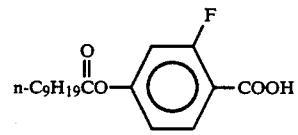

To a solution of 2-fluoro-4-hydroxybenzoic acid (2 g) and triethylamine (1.4 g) in dichloromethane (40 ml) were added decanoylchloride (2.7 g) and dimethylaminopyridine (0.2 g). The solution was stirred at room temperature for about 20 hours. To the solution was added dilute aqueous hydrochloric acid solution and the organic layer was separated by a funnel. The layer was distilled to remove the solvent. The residue was washed with n-hexane and dried to obtain the titled compound (about 2.8 g).

(4) Synthesis of 4-(1,1,1-trifluoro-2-nonylcarbonyloxy)phenyl-2-fluoro-4-n-decanoyloxybenzoate

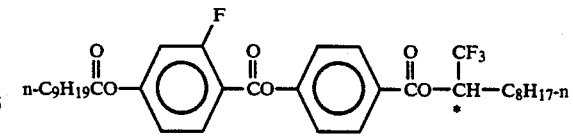

To a solution of the 2-fluoro-4-n-nonylcarbonyloxybenzoic acid (0.3 g) obtained in (3) above and the 1,1,1-trifluoro-2-decyl 4-hydroxybenzoate (0.3 g) obtained in (2) above in tetrahydrofuran (about 30 ml) were added dicyclohexylcarbodiimide (0.25 g) and dimethylaminopyridine (0.02 g). The solution was stirred at room temperature for about 20 hours. The solution was distilled to remove the solvent. The residue was dissolved in dichloromethane and washed with water. The organic layer was dried over anhydrone magnesium sulfate and distilled to remove the solvent.

The residue was purified by silica-gel column chromatography (developer : hexane/ethyl acetate =20/1) to obtain the titled compound (0.21 g).

Phase transition temperatures (° C.) were observed under a polarization microscope with a hot stage.

Figure 39:
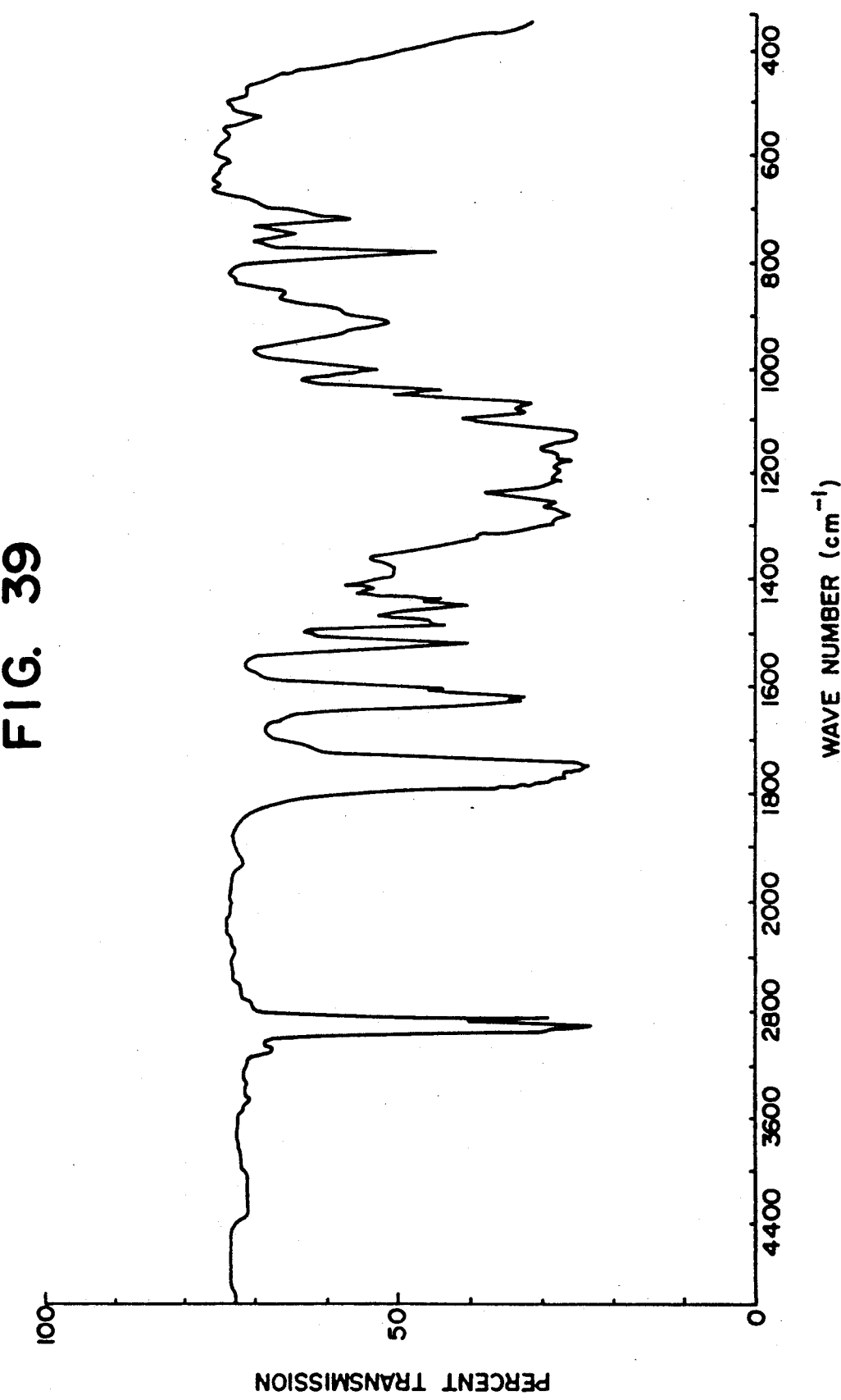

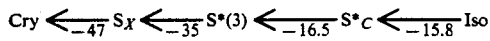

where
S*(3) : tristable state,
S$_X$ : higher state having field response.
FIG. 39 is an IR spectrum of the titled compound.

Example 33

(1) Synthesis of 2-fluoro-4-n-tridecanoyloxybenzoic acid

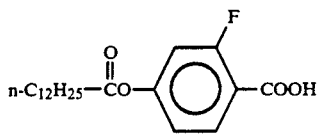

To a solution of 2-fluoro-4-hydroxybenzoic acid (1.4 g) and triethylamine (1.0 g) in dichloromethane (40 ml) were added tridecanoyl chloride (2.0 g) and dimethylaminopyridine (0.2 g). The solution was stirred at room temperature for about 20 hours and thereto was added dilute aqueous hydrochloric acid solution. The organic layer was separated by a funnel and distilled to remove the solvent. The residue was washed with n-hexane and dried to obtain the titled compound (about 1.8 g).

(2) Synthesis of
4-(1,1,1-trifluoro-2-decyloxycarbonyl)phenyl
2-fluoro-4-n-15 tridecanoyloxybenzoate

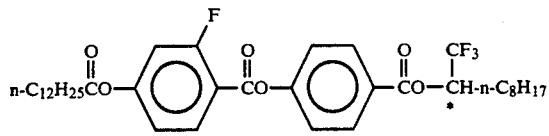

To a solution of the 2-fluoro-4-n-tridecanoyloxybenzoic acid (0.37 g) obtained in (1) above and the 1,1,1-trifluoro-2-decyl 4-hydroxybenzoate (0.3 g) obtained in Example 31, (2) in tetrahydrofuran (about 30 ml) were added dicyclohexylcarbodiimide (0.25 g) and dimethylaminopyridine (0.02 g). The solution was stirred at room temperature for about 20 hours, and distilled to remove the solvent. The residue was dissolved in dichloromethane and washed with water. The organic layer was dried over anhydrous magnesium sulfate and distilled to remove the solvent. The residue was purified by silica-gel column chromatography (developer : hexane/ethyl acetate =20/1) to obtain the titled compound (0.18 g).

Phase transition temperatures (° C) were observed under a polarization microscope using a hot stage.

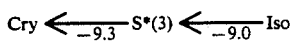

where
S*(3) : tristable state.

Figure 40:
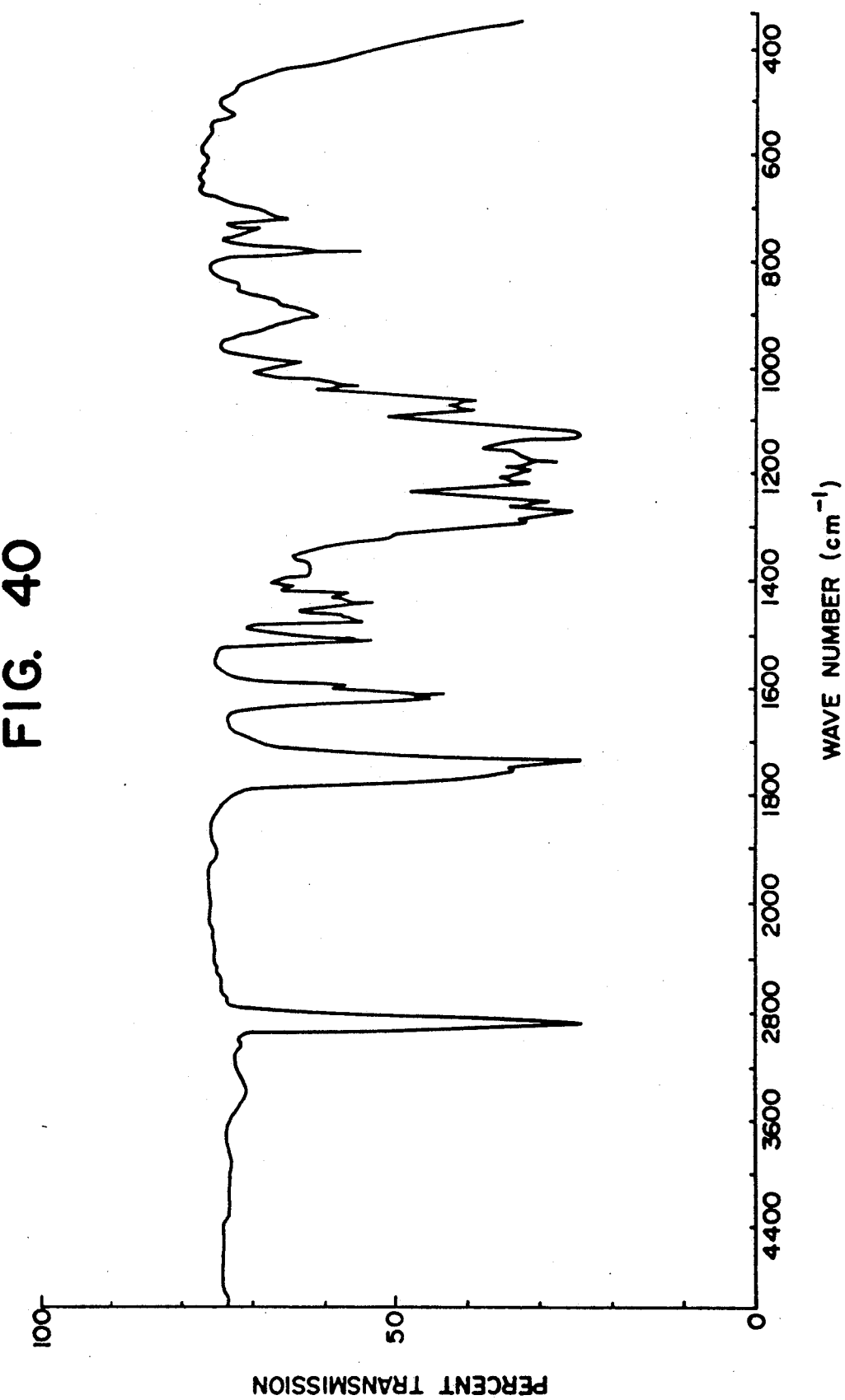

FIG. 40 is an IR spectrum of the titled compound.

Example 34

Synthesis of
3-fluoro-4-(1,1,1-trifluoro-2-decyloxycarbonyl)phenyl
3-fluoro-4-decyloxybiphenyl-4'-carboxylate

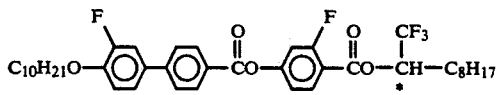

Example 18 was repeated except 1,1,1-trifluro-2-decanol was used in place of the optically active 1,1,1-trifluoro-2-octanol to obtain the titled The compound showed liquid crystal property. Phase transition temperature (° C.) observed under a polalization microscope using a hot stage were

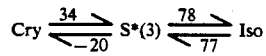

Example 35

In liquid crystal cells wherein the polyimide alignment films which had been subjected to rubbing treatments were placed on ITO electrode substrates, were filled the liquid crystal compounds of isotropic phases obtained by the examples until liquid crystal thin film cells were prepared, as shown in Table 1.

Figure 9:
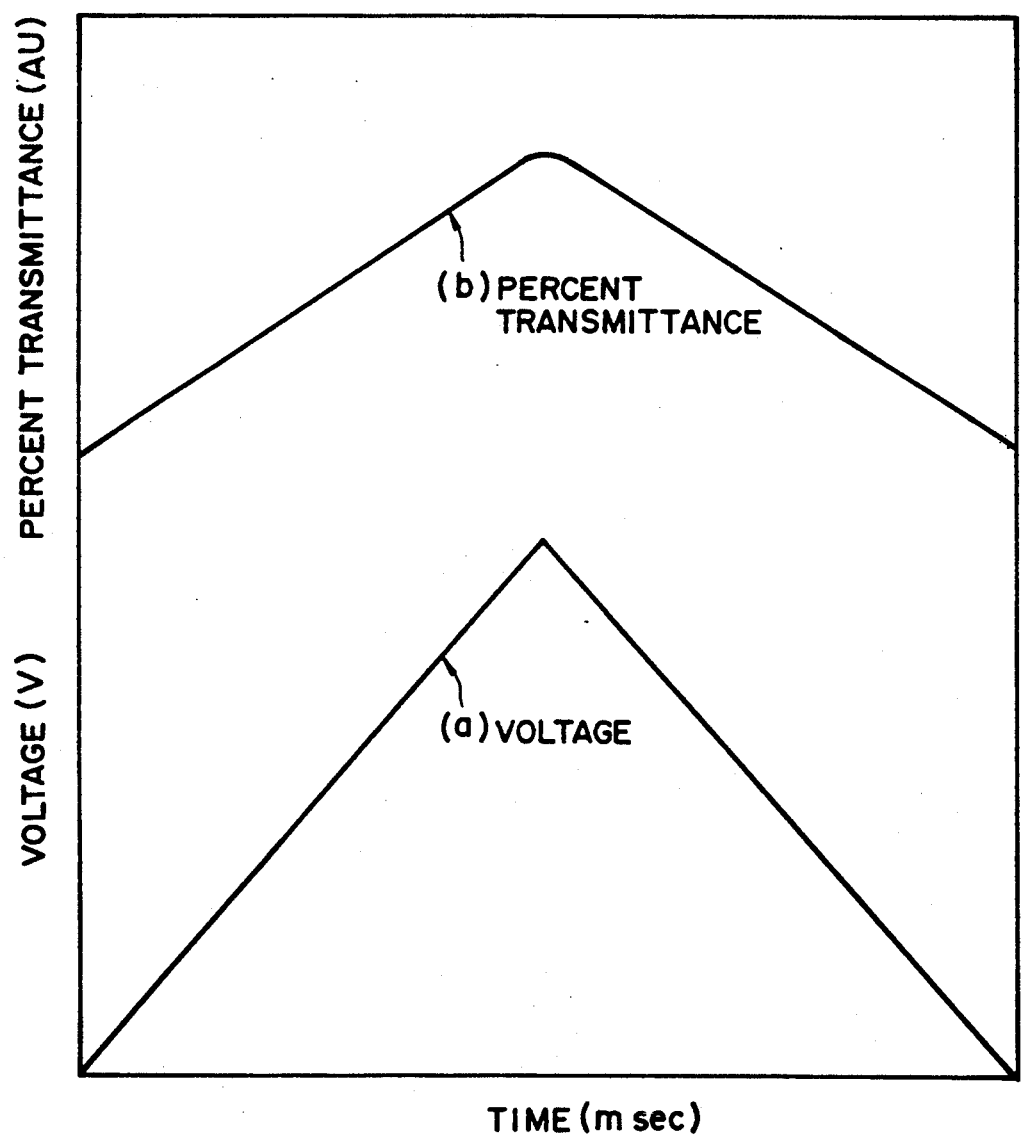
Figure 41:
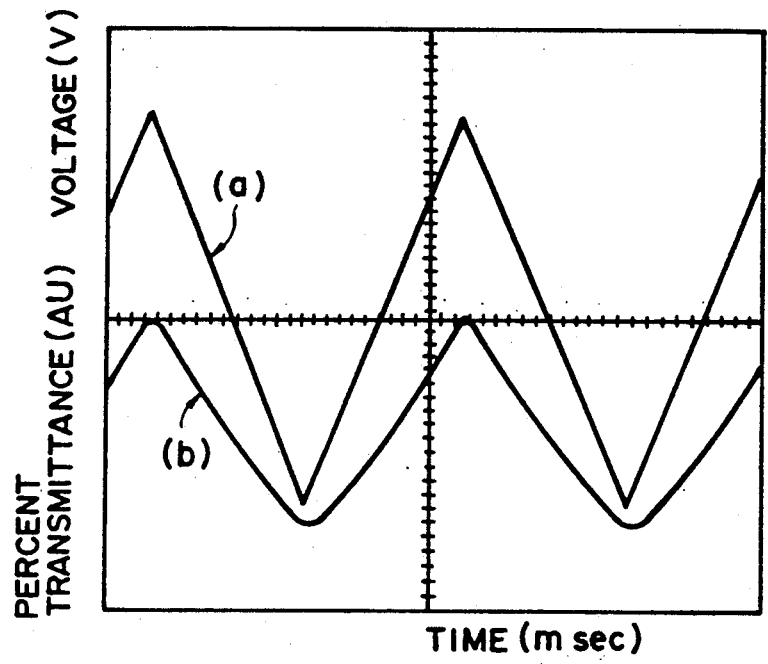

The thin film cells were slowly cooled under temperature gradient of 0.1°-1.0° C./min in order to align the S$_A$ phases. Electric voltages having triangular waves shown in Table 1 were impressed and electro-optical responses were observed under a polarization microscope with a photomultiplier. Electroclinic effects (b) were observed which optically respond to applied electric fields (a) at S$_A$ phases (FIG. 9 and 41). The same effects were observed with respect to all compounds shown in Table 1.

Example 36

Synthesis of
3-fluoro-4-(1-trifluoromethylheptyl-oxycarbonyl)phenyl 3-fluoro-4-nonyloxybiphenyl-4'-carboxylate

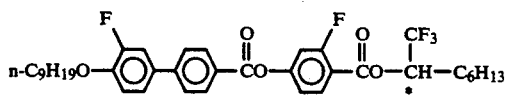

Example 1 was repeated except that 3-fluoro-4-nonyloxybiphenyl-4'-carboxylic acid chloride was used in place of the 4-n-octyloxybiphenyl 4'-carboxylic acid chloride to obtain the titled compound.

Phase transition temperatures (° C.) were

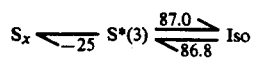

where S$_X$ : unidentified higher state smectic phase.

Example 37

Synthesis of 3-fluoro-4-(1-trifluoromethylnonyl-oxycarbonyl)phenyl 3-fluoro-4-nonyloxybiphenyl-4'-carboxylate

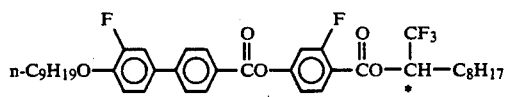

Example 35 was repeated except that 1-trifluoromethyl nonanol was used in place of the optically active 1-trifluoromethyl heptanol to obtain the titled compound.

Phase transition temperatures (° C.) were

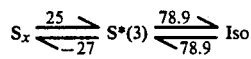

$S_x$: Higher state smectic phase.

Example 38

Synthesis of 3-chloro-4-(1-trifluoromethylheptyloxycarbonyl)phenyl 4-octyloxy-4'-biphenyl carboxylate

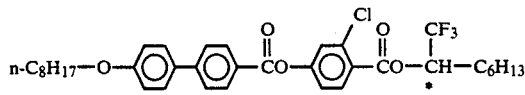

Example 1 was repeated except that 2-chloro-4-benzyloxybenzoic acid chloride was used in place of the benzyloxybenzoic acid chloride in (1) therein, to obtain the titled compound.

The compound was liquid crystal compound and phase transition temperatures (° C.) by means of differential thermal analysis and phase identification by polarizing microscope with a hot-stage were

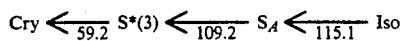

Example 39

Synthesis of 3-trifluoromethyl-4-(1-trifluoromethylheptyloxycarbonyl)phenyl 4-octyloxy-4'-biphenylcarboxylate

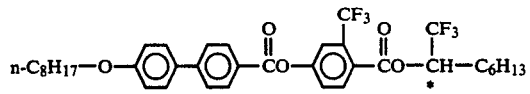

Example 1 was repeated except that 2-trifluoromethyl-4-benzyloxybenzoic acid chloride was used in place of the 4-benzyloxybenzoic acid chloride in (1) therein to obtain the titled compound.

The crystal was liquid crystal compound and phase transition temperatures (° C.) by means of differential thermal analysis and phase identification by a polarizing microscope with a hot-stage were

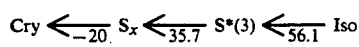

where $S_x$: High state smectic phase

Example 40

Synthesis of 3-methyl 4-(1-trifluoromethylheptyloxycarbonyl)phenyl 4-octyloxy-4'-biphenylcarboxylate

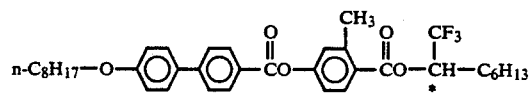

Example 1 was repeated except that 2-methyl-4-benzyloxybenzoic acid chloride was used in place of the 4-benzyloxybenzoic acid chloride to obtain the titled compound.

The compound was liquid crystal compound and phase transition temperature (° C) by means of differential thermal analysis and phase identification by a polarizing microscope with a hot-stage were

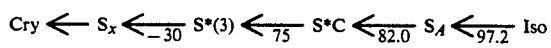

Example 41

Synthesis of 3-bromo-4-(1-trifluoromethylheptyloxycarbonyl)phenyl 4-octyloxy-4'-biphenylcarboxylate

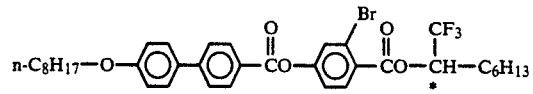

Example 1 was repeated except that 2-bromo-4-benzyloxybenzoic acid chloride was used in place of the 4-benzyloxybenzoic acid chloride in (1) therein to obtain the titled compound.

The compound was liquid crystal compound and phase transition temperatures (° C.) by means of differential thermal analysis and phase identification by a polarizing microscope with a hot stage were

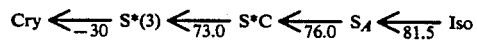

Example 42

3-Fluoro-4-(1-trifluoromethylheptyloxycarbonyl)phenyl 4-octyloxybiphenyl-3'-fluoro-4'-carboxylate

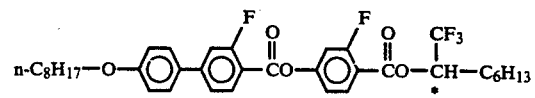

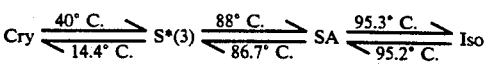

Example 43

2-Fluoro-4-(1-trifluoromethylheptyloxycarbonyl)phenyl 4-octyloxybiphenyl-3'-fluoro-4'carboxylate

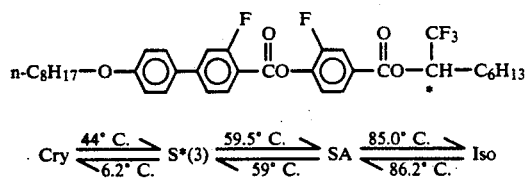

Example 44

4-(1-Trifluoromethylheptyloxycarbonyl)phenyl 4-octyloxybiphenyl-3'-fluoro-4'-carboxylate

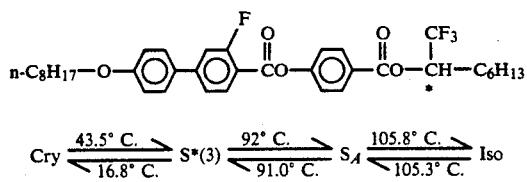

Example 45

4-(1-Trifluoromethylheptyloxycarbonyl)phenyl 4-octyloxybiphenyl-2'-fluoro-4'-carboxylate

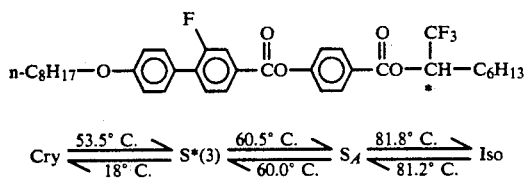

Example 46

4-(1-Trifluoromethylheptyloxycarbonyl)phenyl 4-heptylbiphenyl-2'-fluoro-4'-carboxylate

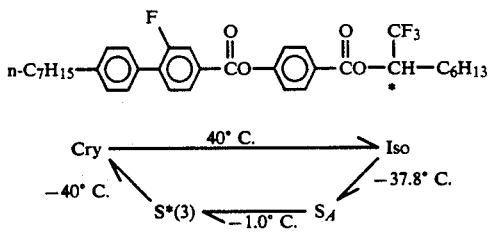

Example 47

3,5-Difluoro-4-(1-trifluoromethylheptyloxycarbonyl)phenyl 4-octyloxybiphenyl 4'-carboxylate

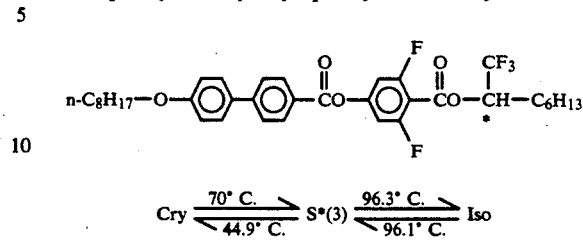

Example 48

2-Fluoro-4-(1-trifluoromethylheptyloxycarbonyl)phenyl 4-octyloxybiphenyl-4'-carboxylate

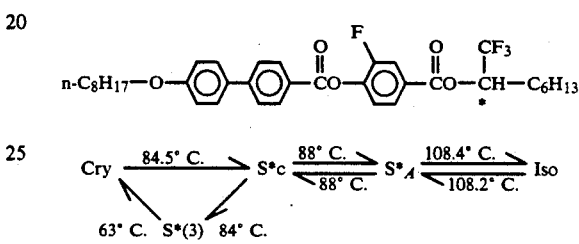

Example 49

In polarization microscopes with photomultipliers wherein two polarizing plates were crossed with a right angle, were placed liquid crystal cells prepared in the same manner as in Example 35 so that long axes of molecules turned parallel to polarizers when minus voltages were applied. The liquid crystal cells were slowly cooled with temperature gradient of 0.1°–1.0° C./min. to S*(3) phases. After further cooling was made, triangular wave voltages (a) was applied at the temperature range as shown in Table 1 (FIGS. 5, 10, 11, 13 and 42). Light transmittance changed in three states (c), i.e., darkness when applied voltages were minus, intermediate when the voltages were zero and brightness when the voltages were plus, and the corresponding switching current peaks (b) appeared accordingly. Presence of three stable alignment of liquid crystals were identified.

So far as the compound in Example 10 was concerned, it showed switching of the electroclinic effect at the $S_A$ phase (FIG. 6) when triangular wave voltages (a) of ±15 V, 10 Hz were applied at the same temperature range (FIG. 7). There were three states in percent transmission even if frequency was made twice (FIG. 7). Presence of three stable alignments in liquid crystal molecules was confirmed.

TABLE 1

Figure 10:
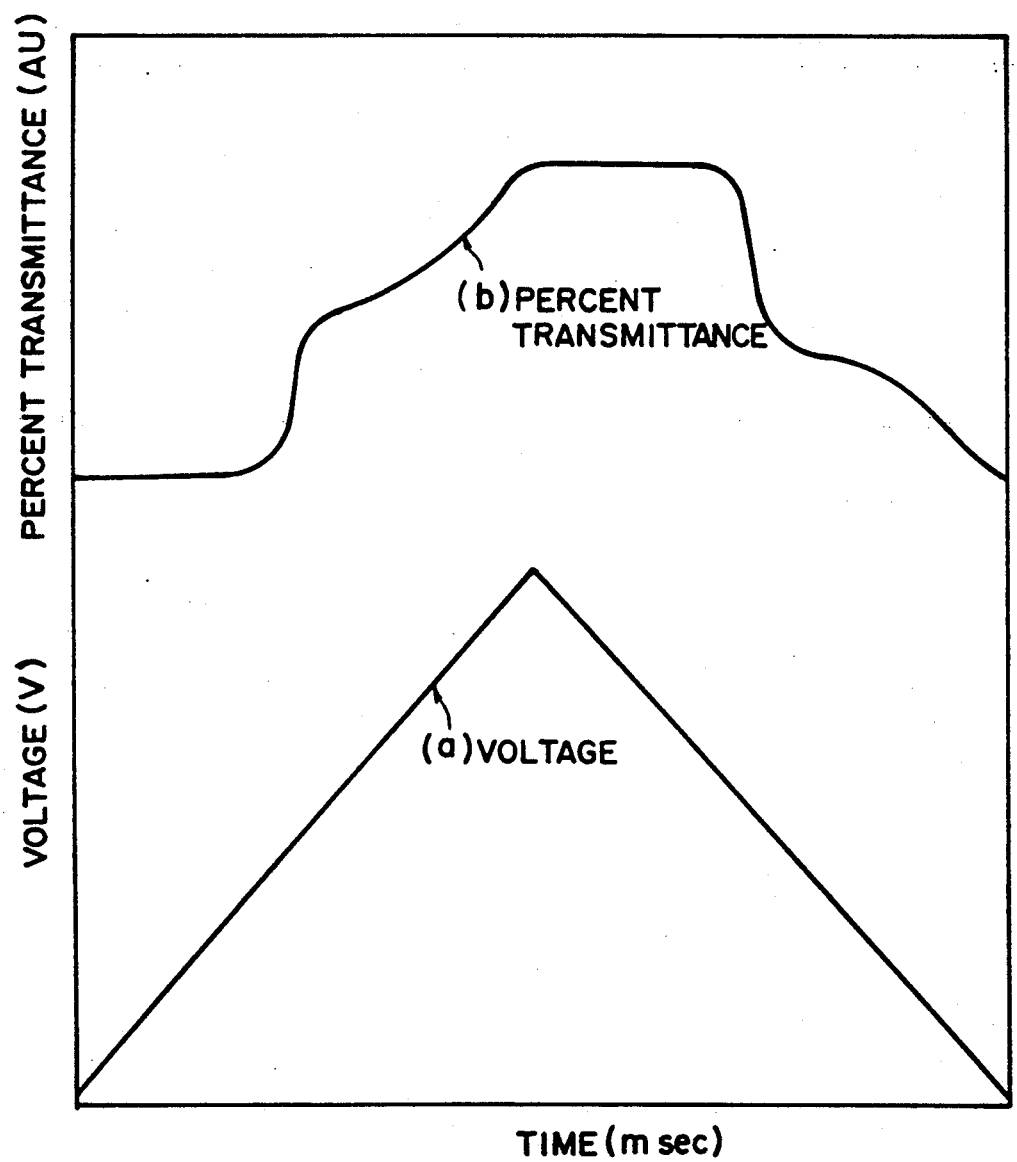
Figure 13:
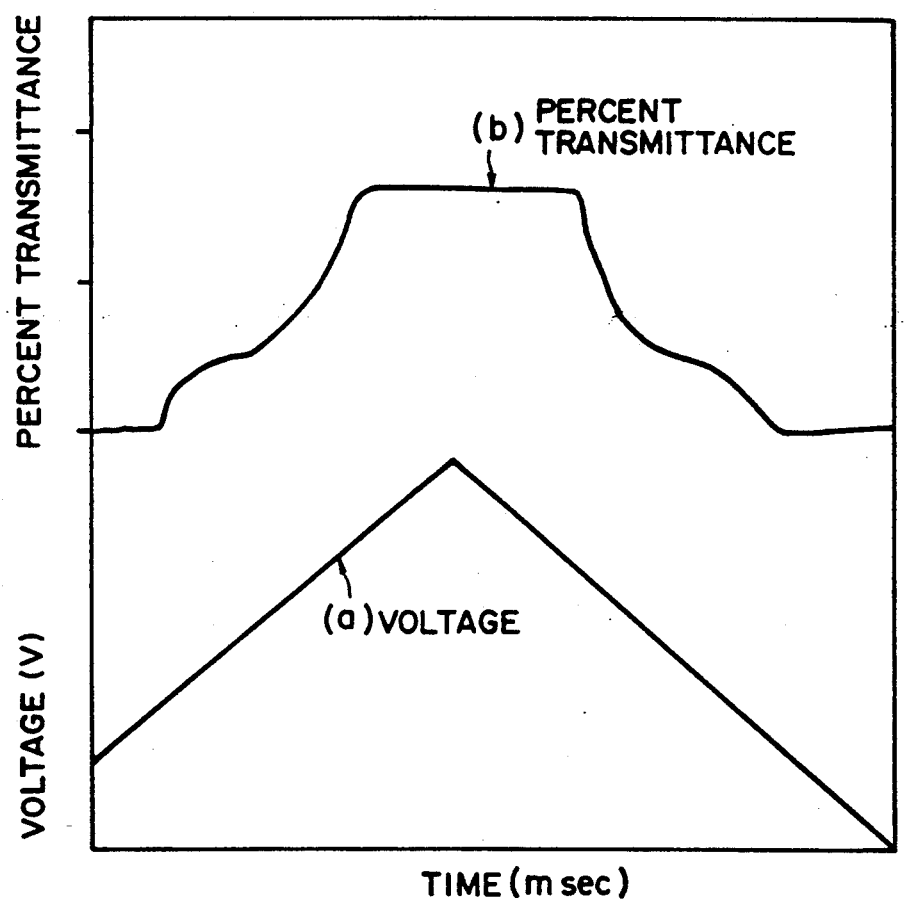
Figure 42:
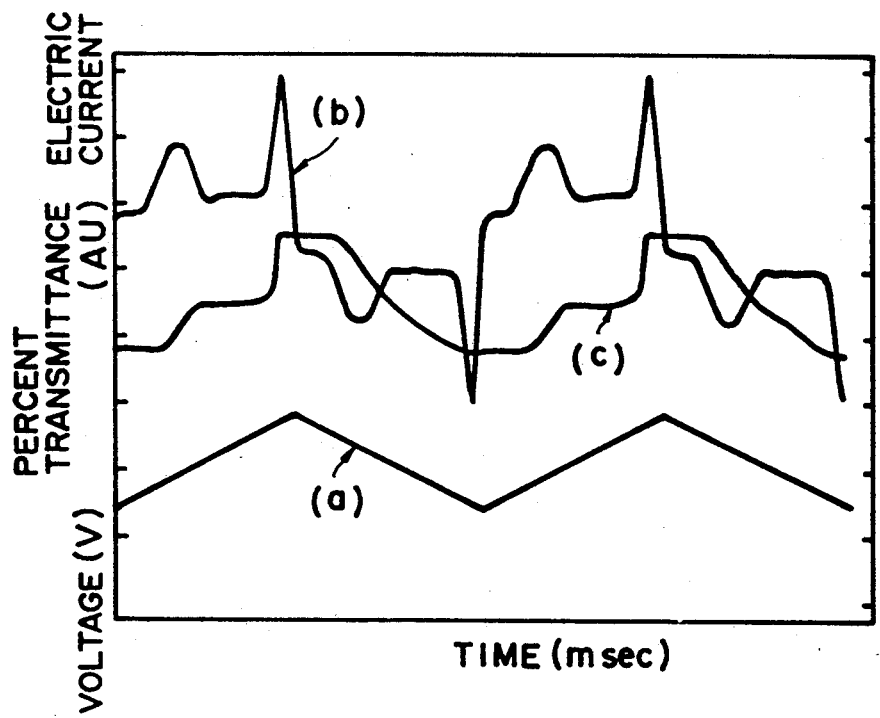

| Group of liquid crystal | Example No. from which the liquid crystals obtained | Cell thickness of liquid crystal cell μm | Example 35 | | Example 36 | | |
|---|---|---|---|---|---|---|---|
| | | | Electric voltage applied | Response to the electric field | Temperature °C. | Electric voltage applied | Response to the electric field |
| 1 | 1–5, 9, 10 | 2.5 | ±15 V, 10 Hz | FIG. 6 | 76–39 | ±30 V, 10 Hz | FIG. 5 |
| 2 | 12, 13, 14 | 2.1 | — | — | −5——13 | ±30 V, 10 Hz | FIG. 13 |
| 3 | 15–24 | 2.8 | ±15 V, 10 Hz | FIG. 41 | 110——2 | ±30 V, 10 Hz | FIG. 42 |
| 4 | 25–28 | 2.1 | ±30 V, 10 Hz | FIG. 9 | 20–45 | ±40 V, 10 Hz | FIG. 10 |
| 5 | 29–31 | 2.1 | ±30 V, 10 Hz | FIG. 9 | 22.7–32.8 | ±30 V, 10 Hz | FIG. 10 |

TABLE 1-continued

Figure 11:
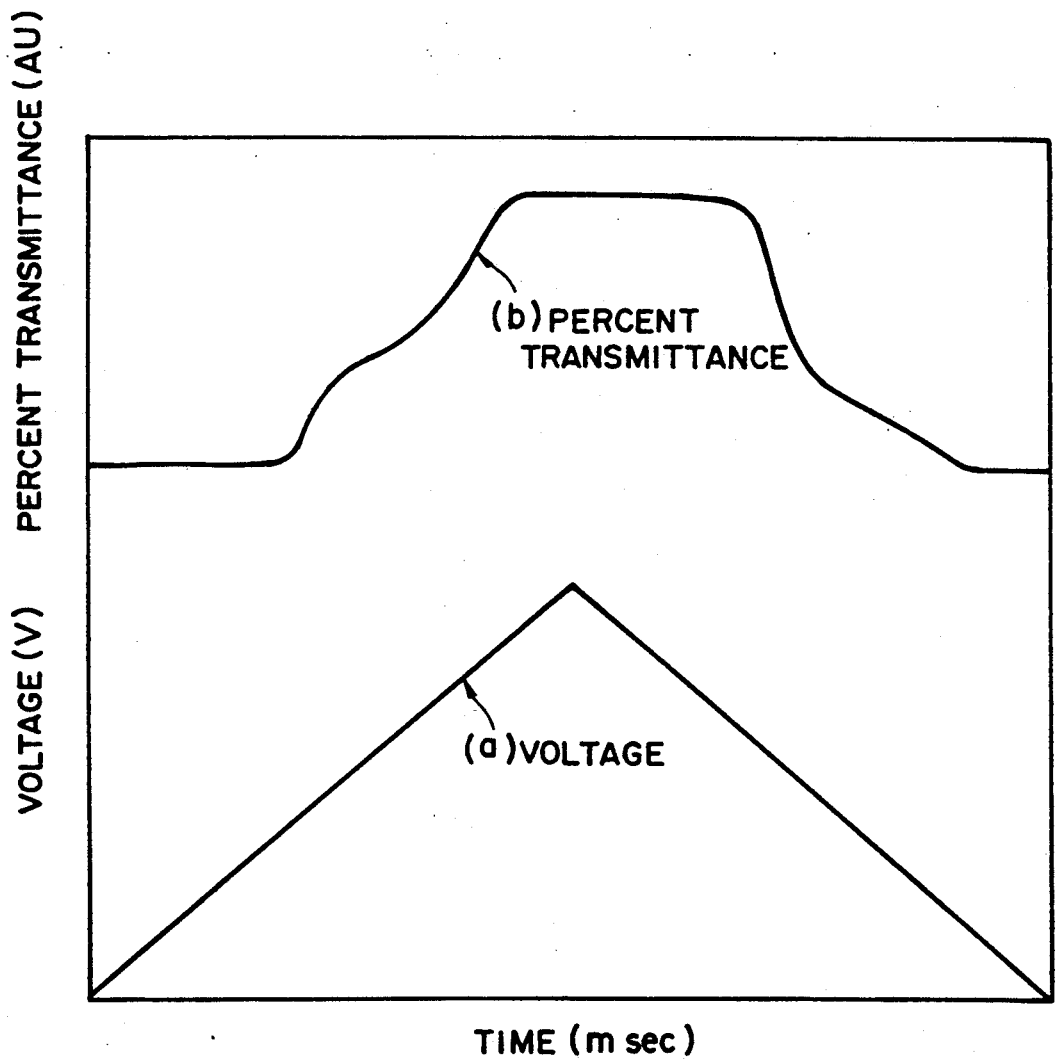
Figure 12A:
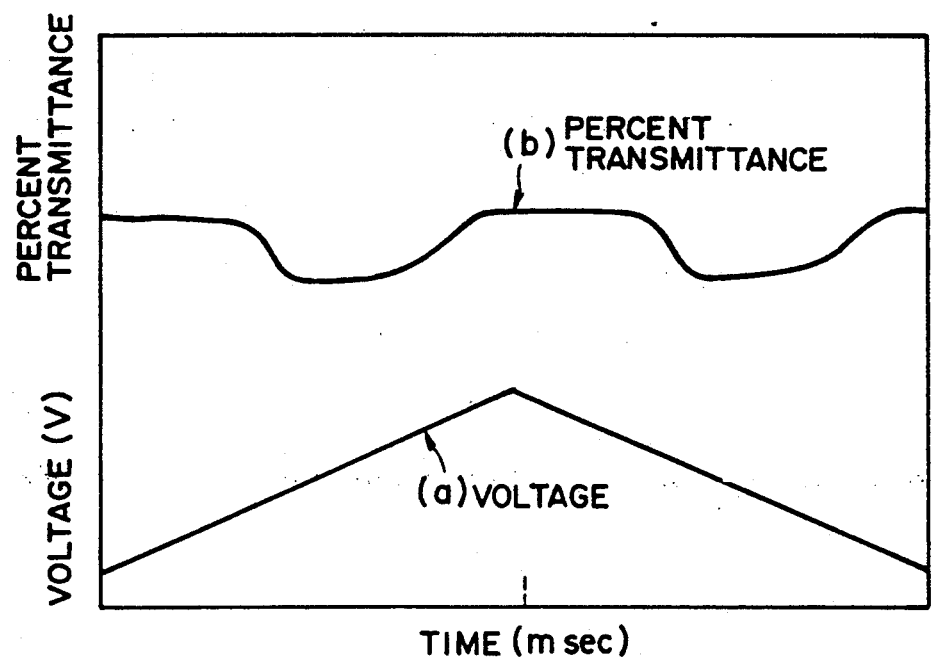
Figure 12B:
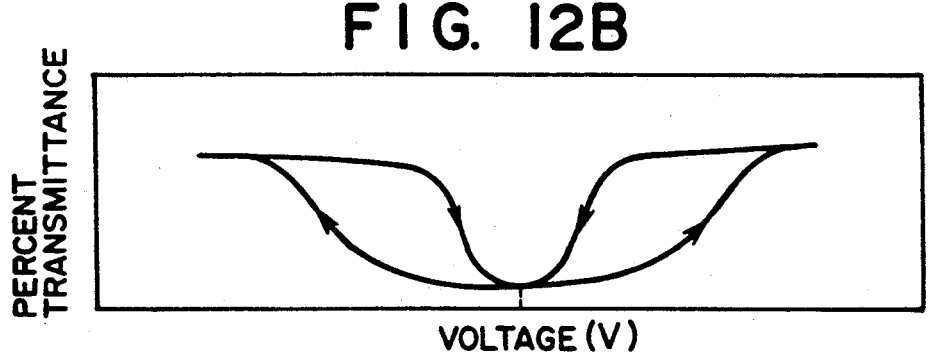

| Group of liquid crystal | Example No. from which the liquid crystals obtained | Cell thickness of liquid crystal cell μm | Example 35 | | Example 36 | | |
|---|---|---|---|---|---|---|---|
| | | | Electric voltage applied | Response to the electric field | Temperature °C. | Electric voltage applied | Response to the electric field |
| 6 | 32, 33 | 2.1 | — | — | −16.5--35 | ±30 V, 10 Hz | FIG. 11 |

Example 50

In a liquid crystal cell (cell thickness =2.5 μm) having polyimide alignment film which had been subjected to a rubbing treatment on a ITO electrode substrate, was filled with the liquid crystal compound obtained in Example 16 in an isotropic phase in order to prepare a liquid crystal thin film cell.

Figure 8:
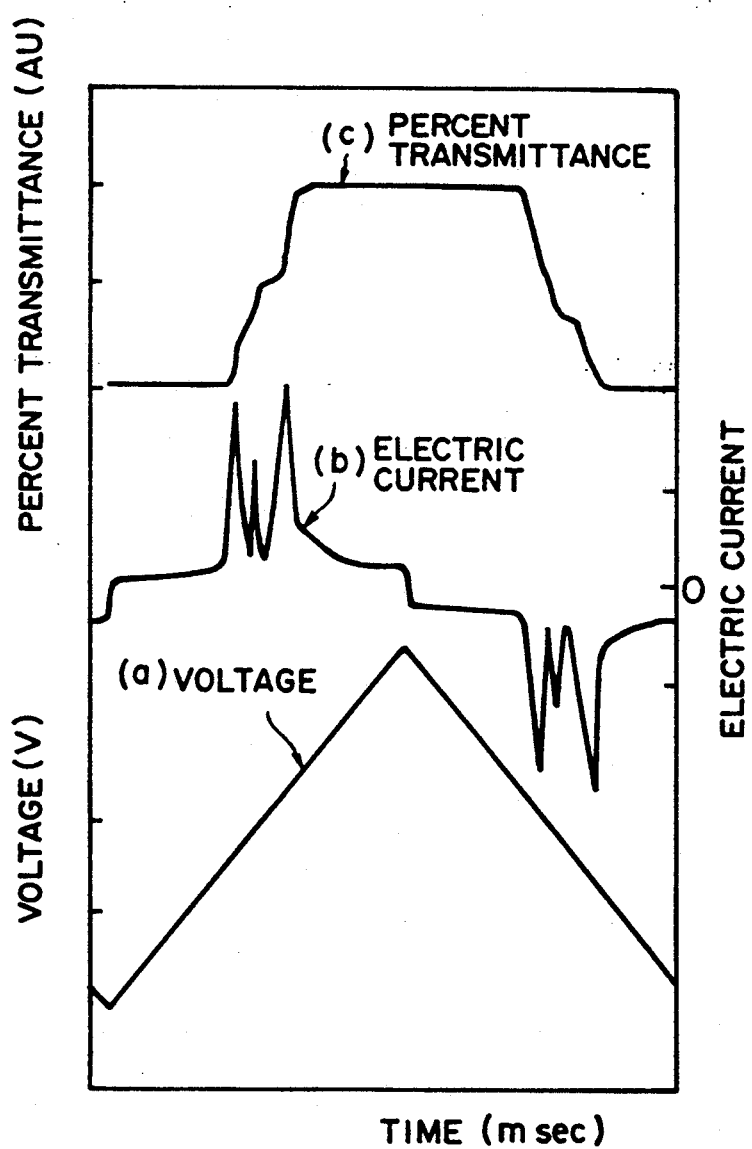

The cell was slowly cooled with temperature gradient of 0.1°–1.0° C./min. until an Sc* phase was aligned. Further cooling was made. Triangular wave voltage (a) of ±30 V, 10 Hz was applied at a temperature range of 98.5–97° C. (FIG. 8).

Transmitted light intensity changed in four states, i.e., darkness - intermediate (1) - intermediate (2) - brightness. Three switching current peaks appeared corresponding to different state. Presence of four stable alignments in a liquid crystal molecule was identified.

Example 51

In a polarizing microscope with a photomultiplier where two polarizing plates were crossed with a right angle, was placed in the same manner as in Example 36 a liquid crystal cell of 2.5 μm thick where the compound prepared in Example 16 was filled so that a long axes of a molecule and a polarizer were in the same direction when no voltage was applied.

Figure 43:
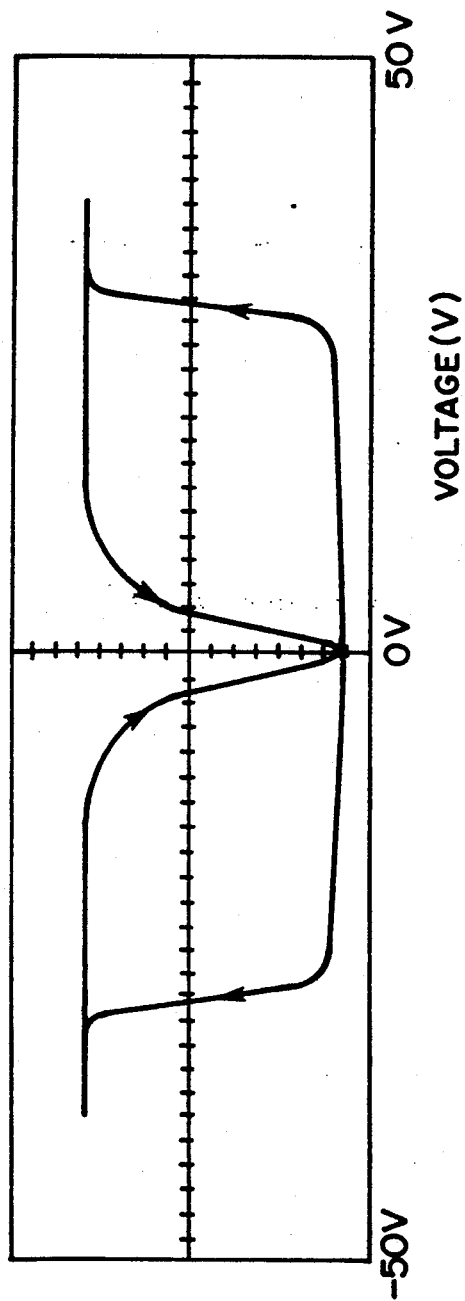
FIG. 43 is a hysteresis of a liquid crystal showing a tetrastable state.

The liquid crystal thin film cell was slowly cooled with temperature gradient of 0.1°–1.0 ° C./min. until as S*(3) phase was aligned. Further cooling was made. Relation of voltage applied to transmitted light intensity 30 when a triangular wave voltage (a) of ±30 V, 10 Hz was applied at a temperature range of 75° C. (FIG. 43). Clear direct current threshold and hysteresis of transmitted light intensity against applied electric field were observed.

We claim:

1. Liquid crystal compound having the formula (I):

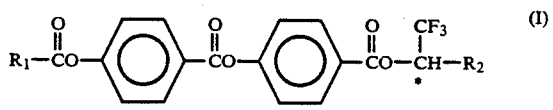

wherein $R_1$ is a $C_{8-18}$ alkyl group and $R_2$ is a $C_{6-16}$ alkyl group, which has S*(3) phase showing tristable states.

2. Liquid crystal compound according to claim 1, which is in the S*(3) phase showing tristable states.

3. Liquid crystal compound having the formula (XII):

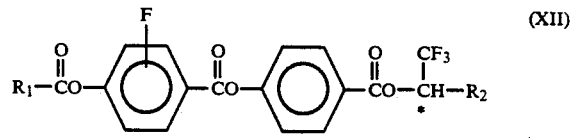

wherein $R_1$ is a $C_{8-18}$ alkyl group and $R_2$ is a $C_{6-16}$ alkyl group, which has S* (3) phase showing tristable states.

* * * * *